(12) United States Patent
Ricchetti et al.

(10) Patent No.: US 11,679,149 B2
(45) Date of Patent: Jun. 20, 2023

(54) IMMUNOGENIC COMPOSITIONS

(71) Applicant: GLAXOSMITHKLINE BIOLOGICALS, S.A., Rixensart (BE)

(72) Inventors: Beatrice Ricchetti, Siena (IT); Isabel Delany, Siena (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 16/311,792

(22) PCT Filed: Jun. 29, 2017

(86) PCT No.: PCT/EP2017/066213
§ 371 (c)(1),
(2) Date: Dec. 20, 2018

(87) PCT Pub. No.: WO2018/002270
PCT Pub. Date: Jan. 4, 2018

(65) Prior Publication Data
US 2020/0023051 A1    Jan. 23, 2020

(30) Foreign Application Priority Data

Jun. 29, 2016   (EP) .................................... 16177013

(51) Int. Cl.
| | | |
|---|---|---|
| *A61K 39/095* | (2006.01) | |
| *C12N 9/14* | (2006.01) | |
| *A61K 39/00* | (2006.01) | |

(52) U.S. Cl.
CPC ............. *A61K 39/095* (2013.01); *C12N 9/14* (2013.01); *C12Y 306/03001* (2013.01); *A61K 2039/55555* (2013.01)

(58) Field of Classification Search
None
See application file for complete search history.

(56) References Cited

U.S. PATENT DOCUMENTS

| | | |
|---|---|---|
| 5,681,736 A | 10/1997 | Pace et al. |
| 5,997,881 A | 12/1999 | Powell et al. |
| 2020/0023051 A1 | 1/2020 | Ricchetti et al. |

FOREIGN PATENT DOCUMENTS

| | | |
|---|---|---|
| AU | 2012211495 B2 * | 8/2014 |
| EP | 2279747 B1 | 6/2014 |
| WO | 1999/57280 A3 | 11/1999 |
| WO | 2000/26384 A1 | 5/2000 |
| WO | 2000/66741 A2 | 11/2000 |
| WO | 2002062378 A2 | 8/2002 |
| WO | 2003/010194 A2 | 2/2003 |
| WO | 2003/063766 A2 | 8/2003 |
| WO | 2004/048404 A2 | 6/2004 |
| WO | 2005/107798 A1 | 11/2005 |
| WO | 2006/046143 A2 | 5/2006 |
| WO | 2006046143 A2 | 5/2006 |
| WO | 2009158142 A1 | 12/2009 |
| WO | 2011/036562 A1 | 3/2011 |
| WO | 2011/036564 A2 | 3/2011 |
| WO | 2011036564 A2 | 3/2011 |
| WO | 2014/174043 A1 | 10/2014 |

OTHER PUBLICATIONS

Hooda et al. Nat Microbiol Apr. 2016 vol. 1, pp. 1-9.*
PIR_80 database accession #G81213 Jul. 9, 2004.*
Uniprot Accession # Q9K165 Oct. 1, 2000.*
GenEmbl database accession # AE002098 Jan. 31, 2014.*
EMBL-EBI database ID#AAF40758 May 15, 2014.*
Eckford, et al., "The reconstituted *Escherichia coli* MsbA protein displays lipid flippase activity", Biochemical Journal, vol. 333, No. 1, Jul. 1, 2010 (Jul. 1, 2010), pp. 621-203, XP055321368.
Hooda, Yogesh, et al., "Slam is an outer membrane protein that is required for the surface display of lipidated Virulence factors in Neisseria", Nature Microbiology, vol. 1. No. 4, Feb. 29, 2016 (Feb. 29, 2016), pp. 1-9, article No. 16009, XP009500105.
Kovacs-Simon, A., R.W. Titball, and S.L. Michell, Lipoproteins of bacterial pathogens. Infect Immun, 2011. 79(2): p. 548-61).
Bos, M.P., V. Robert, and J. Tommassen, Biogenesis of the gram-negative bacterial outer membrane. Annu Rev Microbiol, 2007. 61: p. 191-214).
Yogesh Hooda, C.C.-L.L., Andrew Judd, Carolyn M. Buckwalter, Hyejin Esther Shin, Scott D. Gray-Owen and Trevor F. Moraes, Slam is an outer membrane protein that is required for the surface display of lipidated virulence factors in Neisseria. Nature microbiology, 2016. 1).
Sambrook J, F.E., Maniatis T, Molecular cloning: a laboratory manual. Cold Spring Harbor Laboratory, 1989. 2nd ed.
Ieva, R., et al., CrgA is an inducible LysR-type regulator of Neisseria meningitidis, acting both as a repressor and as an activator of gene transcription. J Bacteriol, 2005. 187(10): p. 3421-30).
Oriente, F., V. Scarlato, and I. Delany, Expression of factor H binding protein of meningococcus responds to oxygen imitation through a dedicated FNR-regulated promoter. J Bacteriol, 2010. 192(3): p. 691-701.
Koeberling et al ., J Infect Dis, 198 ( 2008 ), pp. 262-270 ).
Adu-Bobie et al., Infect Immun, 72 (2004), pp. 1914-1919).
Beemink et al. ( Clin Vaccine Immunol, 17 ( 2010 ), pp. 1074-1078.
A. Kulp, M.J. Kuehn Biological functions and biogenesis of secreted bacterial outer membrane vesicles Annual Review of Microbiology, 64 (2010), pp. 163-184.

(Continued)

*Primary Examiner* — Oluwatosin A Ogunbiyi
(74) *Attorney, Agent, or Firm* — Loza & Loza, LLP; Julio Loza

(57) ABSTRACT

The present invention relates to the field of native outer membrane vesicles (nOMVs), particularly nOMVs having increased levels of lipoproteins on their surface and use of same in immunogenic compositions.

17 Claims, 37 Drawing Sheets
(24 of 37 Drawing Sheet(s) Filed in Color)
Specification includes a Sequence Listing.

(56) References Cited

OTHER PUBLICATIONS

S.F. Berianda, A.M. Colucci, L. Maggiore, S. Sanzone, O. Rossi, I. Ferlenghi, et al. High yield production process for Shigella outer membrane particles, PLoS One, 7 (2012), p. e35616.

Murray CJ, Vos T, Lozano R, Naghavi M, Flaxman AD, Michaud C, et al. Disability-adjusted life years (DALYs) for 291 diseases and injuries in 21 regions, 1990-2010: a systematic analysis for the Global Burden of Disease Study 2010. Lancet 2012;380:2197-2223.

Lozano R, Naghavi M, Foreman K, Lim S, Shibuya K, Aboyans V, et al. Global and regional mortality from 235 causes of death for 20 age groups in 1990 and 2010: a systematic analysis for the Global Burden of Disease Study 2010. Lancet 2012;380:2095-2128.

Kotloff KL, Nataro JP, Blackwelder WC, Nasrin D, Farag TH, Panchalingam S, et al. Burden and aetiology of diarrhoeal disease in infants and young children in developing countries (the Global Enteric Multicenter Study, GEMS): a prospective, case-control study Lancet. 2013;382: 209-222.

Livio S, Strockbine NA, Panchalingam S, Tennant SM, Barry EM, Marohn ME, et al. Shigella isolates from the global enteric multicenter study inform vaccine development. Clin Infect Dis. 2014;59: 933-941.

Levine MM, Kotloff KL, Barry EM, Pasetti MF, Sztein MB. Clinical trials of Shigella vaccines: two steps forward and one step back on a long, hard road. Nat Rev Microbiol. 2007;5: 540-553.

Chang Z, Lu S, Chen L, Jin Q, Yang J. Causative species and serotypes of shigellosis in mainland China: systematic review and meta-analysis. PLoS One. 2012;7: e52515.

Minh H, Nhu NTK, Nga TVT, Duy PT, Campbell JI, Hoang NVM, et al. A changing picture of shigellosis in southern Vietnam: shifting species dominance, antimicrobial susceptibility and clinical presentation. BMC Infect Dis. 2009;9: 204.

Kweon, 2008 CurrOpin Infect Dis. 21(3):313-8.

Cohen D, Ashkenazi S, Green MS, Gdalevich M, Robin G, Slepon R, et al. Double-blind vaccine-controlled randomised efficacy trial of an investigational Shigella sonnei conjugate vaccine in young adults. Lancet. 1997;349: 155-159.

Passwell JH, Ashkenzi S, Banet-Levi Y, Ramon-Saraf R, Farzam N, Lemer-Geva L, et al. Age-related efficacy of Shigella O-specific polysaccharide conjugates in 1-4-year-old Israeli children. Vaccine. 2010;28: 2231-2235.

Susanna Esposito, Roman Prymula, Gian Vincenzo Zuccotti, Fang Xie, Michelangelo Barone, Peter M Dull, Daniela Toneatto, A phase II randomized controlled trial of a multicomponent meningococcal serogroup B vaccine, 4CMenB, in infants (II). Human Vaccines & Immunotherapeutics vol. 10, Iss 7, 2014.

Erlandson and Mackey (1958) J Bacteriol 75(3): 253-7.

Uyttendaele et al. (2001) International journal of food microbiology 70(3):255-65.

Formal SB, Kent TH, May HC, Palmer A, Falkow S, LaBrec EH. Protection of monkeys against experimental shigellosis with a living attenuated oral polyvalent dysentery vaccine. J Bacteriol. 1966;92: 17-22.

Makino S, Sasakawa C, Kamata K, Kurata T, Yoshikawa M. A genetic determinant required for continuous reinfection of adjacent cells on large plasmid in S. flexneri 2a. Cell. 1986;46: 551-555.

Berianda Scorza F, Colucci AM, Maggiore L, Sanzone S, Rossi O, Ferlenghi I, et al. High yield production process for Shigella outer membrane particles. PLoS One. 2012;7: e35616.

Prunier A-L, Schuch R, Fernandez RE, Mumy KL, Kohler H, McCormick BA, et al. nadA and nadB of Shigella flexneri 5a are antivirulence loci responsible for the synthesis of quinolinate, a small molecule inhibitor of Shigella pathogenicity. Microbiology. 2007;153: 2363-2372.

Clementz T, Bednarski JJ, Raetz CR. Function of the htrB high temperature requirement gene of *Escherchia coli* in the acylation of lipid A. J Biol Chem. 1996;271: 12095-12102.

Rossi O, Pesce I, Giannelli C, Aprea S, Caboni M, Citiulo F, et al. Modulation of Endotoxicity of Shigella Generalized Modules for Membrane Antigens (GMMA) by Genetic Lipid A Modifications: Relative Activation of TLR4 and TLR2 Pathways in Different Mutants. J Biol Chem. 2014;289: 24922-24935.

Micoli F, Rondini S, Gavini M, Pisoni I, Lanzilao L, Colucci AM, et al. A scalable method for O-antigen purification applied to various *Salmonella serovars*. Anal Biochem. 2013;434: 136-145.

Robbins JB, Kubler-Kielb J, Vinogradov E, Mocca C, Pozsgay V, Shiloach J, et al. Synthesis, characterization, and mmunogenicity in mice of Shigella sonnei O-specific oligosaccharide-core-protein conjugates. Proc Natl Acad Sci U S A. 2009;106: 7974-7978.

Westphal O, Jann K. Bacterial lipopolysaccharides: extraction with phenol-water and further application of the procedure. 1965;5: 83-91.

Stoddard MB, Pinto V, Keiser PB, Zollinger W. Evaluation of a whole-blood cytokine release assay for use in measuring endotoxin activity of group B Neisseria meningitidis vaccines made from lipid A acylation mutants. Clin Vaccine Immunol. 2010; 17: 98-107.

Pyrogens. In: European Pharmacopoeia. 8th ed. Strasbourg, Cedex: Directorate for the Quality of Medicines & Healthcare of the Council of Europe (EDQM). 2013. chapter 2.6.8.

Moscardo E, Maurin A, Dorigatti R, Champeroux P, Richard S. An optimised methodology for the neurobehavioural assessment in rodents. J Pharmacol Toxicol Methods. 2007;56:239-255.

Jiang Y, Yang F, Zhang X, Yang J, Chen L, Yan Y, et al. The complete sequence and analysis of the large virulence plasmid pSS of Shigella sonnei. Plasmid. 2005;54: 149-159.

Rossi O, Maggiore L, Necchi F, Koebeding 0, MacLennan CA, Saul A, et al. Comparison of Colorimetric Assays with Quantitative Amino Acid Analysis for Protein Quantification of Generalized Modules for Membrane Antigens (GMMA). Mol Biotechnol. 2014;in press.

Tettelin et al. (2000) Science 287:1809-1815.

Comanducci et al. (2002) J. Exp. Med. 195:1445-1454.

Masignani et al. (2003) J Exp Med 197:789-799.

Welsch et al. (2004) J Immunol 172:5605-15.

Hou et al. (2005) J Infect Dis 192(4):580-90.

Fletcher et al. (2004) Infect Immun 72:2088-2100.

Zhu et al. (2005) Infect Immun 73(10):6838-45.

Cantini et al. (2006) J. Biol. Chem. 281 7220-7227.

Madico et al. (2006) J Immunol 177:501-10.

Espevik and Niessen, 1986, J. Immunol. Methods 95: 99-105.

Ziegler-Heitbrock et al., 1988, Int. J. Cancer 41: 456-461.

Schwechheimer, C. and M.J. Kuehn, Outer-membrane vesicles from Gram-negative bacteria: biogenesis and functions. Nat Rev Microbiol, 2015. 13(10): p. 605-19.

Fantappie, L., et al., Antibody-mediated immunity induced by engineered *Escherichia coli* OMVs carrying heterologous antigens in their lumen. J Extracell Vesicles, 2014. 3.

* cited by examiner

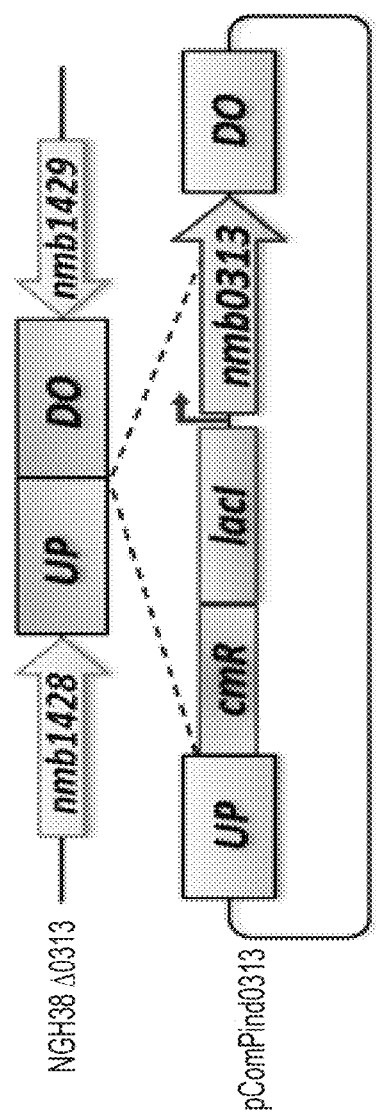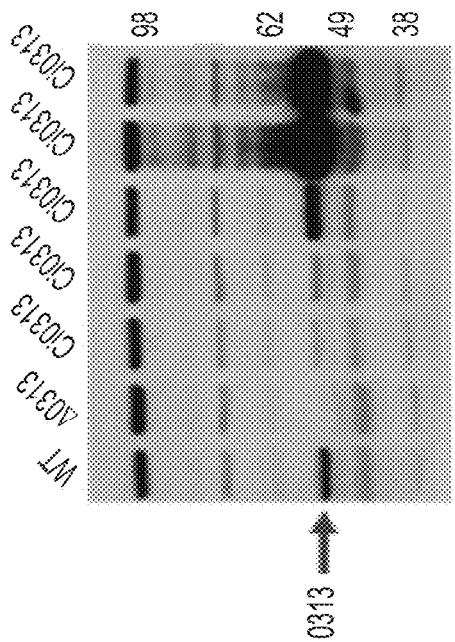
FIG. 4A
FIG. 4B

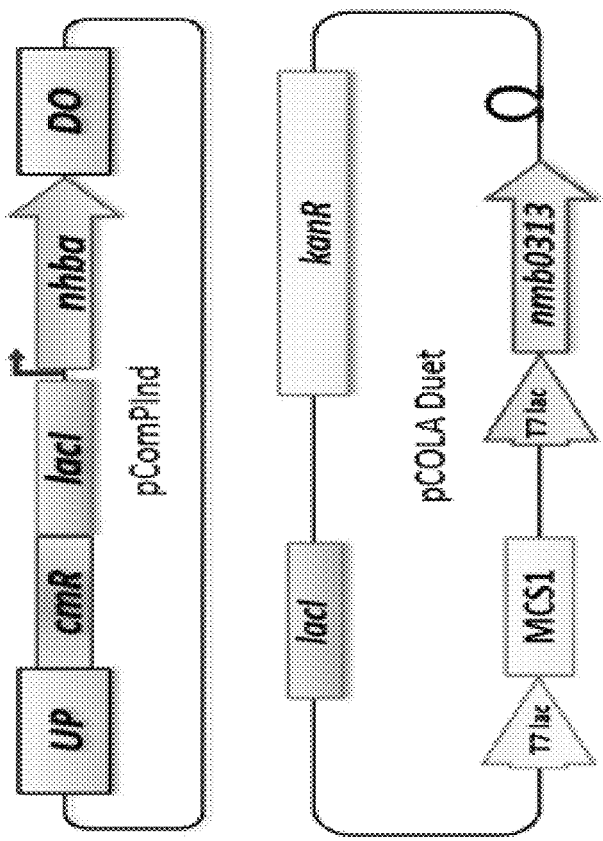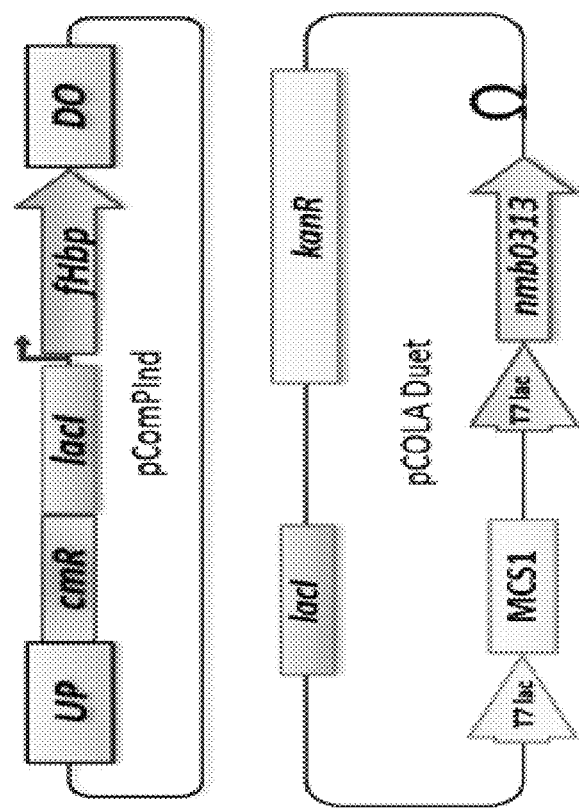
FIG. 6A

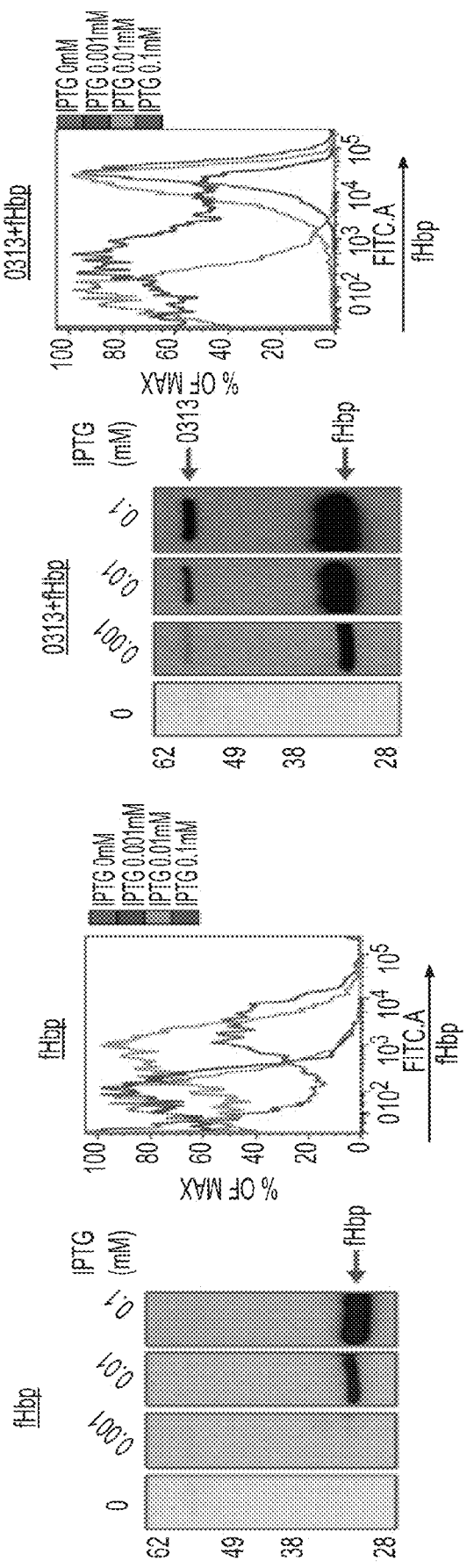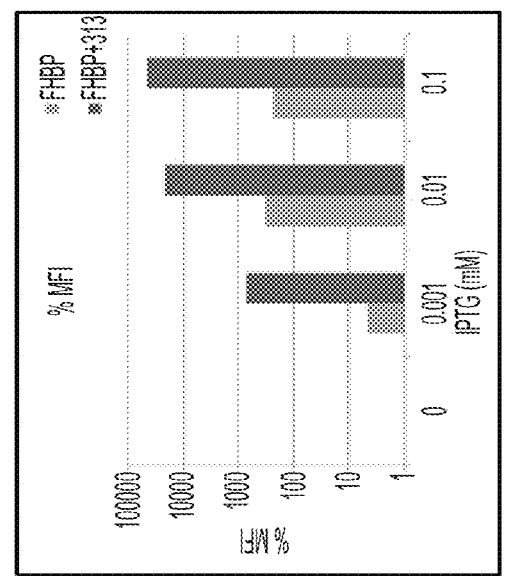
FIG. 6B
FIG. 6C

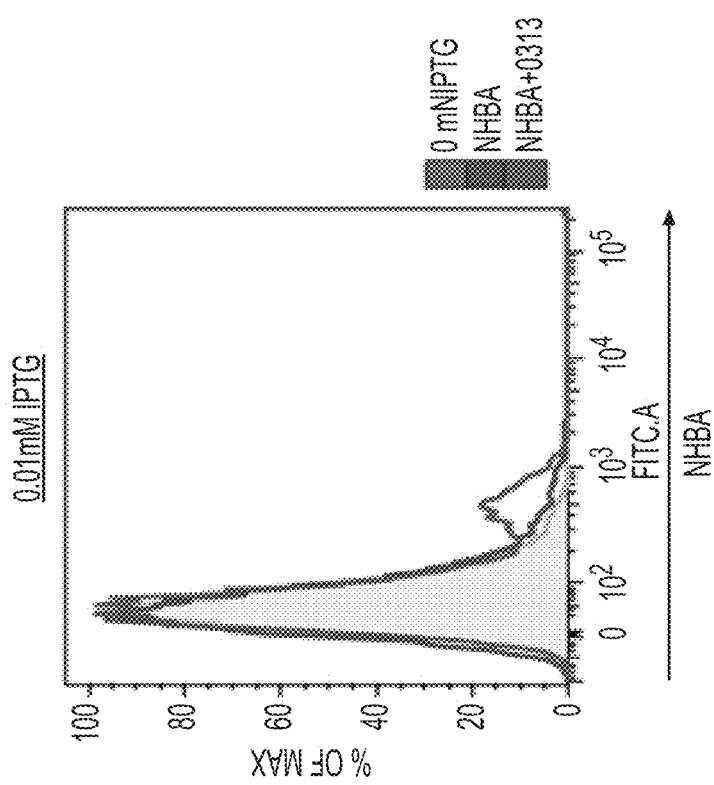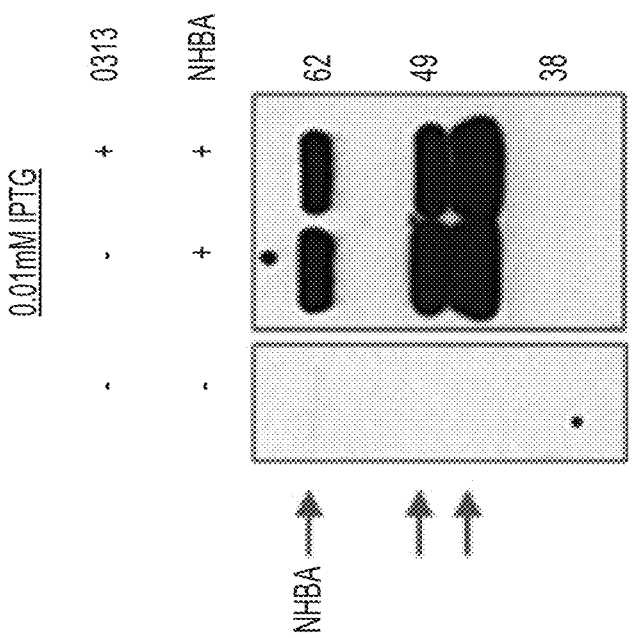
FIG. 6D

| Groups | #mice | Antigen | Adjuvant | Doses (µg) |
|---|---|---|---|---|
| 1 | 8 | Ec OMVs Empty | 3mg/ml Al(OH)$_3$ | 2 |
| 2 | 8 | Ec OMVs NMB0313 | 3mg/ml Al(OH)$_3$ | 2 |
| 3 | 8 | Ec OMVs fHbp | 3mg/ml Al(OH)$_3$ | 2 |
| 4 | 8 | Ec OMVs fHbp | 3mg/ml Al(OH)$_3$ | 0.2 |
| 5 | 8 | Ec OMVs fHbp+NMB0313 | 3mg/ml Al(OH)$_3$ | 2 |
| 6 | 8 | Ec OMVs fHbp+NMB0313 | 3mg/ml Al(OH)$_3$ | 0.2 |
| 7 | 8 | rfHbpv1.1 | 3mg/ml Al(OH)$_3$ | 1 |
| 8 | 5 | Ec OMVs NHBA | 3mg/ml Al(OH)$_3$ | 2 |
| 9 | 5 | Ec OMVs NHBA+NMB0313 | 3mg/ml Al(OH)$_3$ | 2 |
| 10 | 8 | rNHBA p 2 | 3mg/ml Al(OH)$_3$ | 1 |

*FIG. 11*

| Antigen Dose | OMV(E.coli)fhbP-NMB0313- 2ug Alum OH 3 mg/ml | OMV(E.coli)fhbP-NMB0313+ 2ug Alum OH 3 mg/ml | OMV(E.coli)fhbP + 2ug Alum OH 3 mg/ml | OMV(E.coli)fhbP + 0.2ug Alum OH 3 mg/ml | OMV(E.coli)fhbP +NMB0313+ 2ug Alum OH 3 mg/ml | OMV(E.coli)fhbP +NMB0313+ 0.2ug Alum OH 3 mg/ml | fhbPvar1.1 1ug Alum OH 3 mg/ml |
|---|---|---|---|---|---|---|---|
| *topi* | *Gr. 1* | *Gr. 2* | *Gr. 3* | *Gr. 4* | *Gr. 5* | *Gr. 6* | *Gr. 7* |
| 1 | 1 | 6 | 1702 | 240 | 8629 | 7288 | 1649 |
| 2 | 1 | 7 | 118 | 10 | 7547 | 155 | 1933 |
| 3 | 1 | 9 | 1478 | 8 | 373 | 6739 | 1301 |
| 4 | 1 | 8 | 1448 | 46 | 114 | 3754 | 1721 |
| 5 | 1 | 7 | 799 | 2 | 8477 | 4136 | 1595 |
| 6 | 1 | 7 | 1404 | 26 | 4991 | 12128 | 186 |
| 7 | 1 | 3 | 916 | 73 | 4587 | 5529 | 1273 |
| 8 | 1 | 2 | 1647 | 1 | 3558 | 2 | 2163 |
| GMT | 1 | 6 | 961 | 16 | 2572 | 1413 | 1247 |
| C.V. | 0 | 39 | 45 | 158 | 70 | 80 | 41 |

*FIG. 12B*

| Experimental Group | Treatment 1 | | rSBA pool rabbit complement lot 6352 |
| --- | --- | --- | --- |
| | ID | Quantity (ug) | H44/76 |
| 1 | OMV Ecoli fHbp-NMB0313- | 2 | <16 |
| 2 | OMV Ecoli NMB0313+ | 2 | <16 |
| 3 | OMV Ecoli fHbp+ | 2 | 65536 |
| 4 | OMV Ecoli fHbp+ | 0.2 | 8192 |
| 5 | OMV Ecoli fHbp+NMB0313+ | 2 | 524288 |
| 6 | OMV Ecoli fHbp+NMB0313+ | 0.2 | 524288 |
| 7 | fHbpv1.1 | 1 | 16384 |

*FIG. 13B*

| Experimental Group | Treatment 1 | | Animal | rSBA pool rabbit complement lot 6352 |
|---|---|---|---|---|
| | ID | Quantity (ug) | | H44/76 |
| 3 | OMV Ecoli fHbp+ | 2 | 17 | 131072 |
| 3 | OMV Ecoli fHbp+ | 2 | 18 | 8192 |
| 3 | OMV Ecoli fHbp+ | 2 | 19 | 131072 |
| 3 | OMV Ecoli fHbp+ | 2 | 20 | 262144 |
| 3 | OMV Ecoli fHbp+ | 2 | 21 | 262144 |
| 3 | OMV Ecoli fHbp+ | 2 | 22 | >262144 |
| 3 | OMV Ecoli fHbp+ | 2 | 23 | >262144 |
| 3 | OMV Ecoli fHbp+ | 2 | 24 | 262144 |
| 4 | OMV Ecoli fHbp+ | 0.2 | 25 | 16384 |
| 4 | OMV Ecoli fHbp+ | 0.2 | 26 | 4096 |
| 4 | OMV Ecoli fHbp+ | 0.2 | 27 | 128 |
| 4 | OMV Ecoli fHbp+ | 0.2 | 28 | 128 |
| 4 | OMV Ecoli fHbp+ | 0.2 | 29 | <128 |
| 4 | OMV Ecoli fHbp+ | 0.2 | 30 | 8192 |
| 4 | OMV Ecoli fHbp+ | 0.2 | 31 | 4096 |
| 4 | OMV Ecoli fHbp+ | 0.2 | 32 | <128 |
| 5 | OMV Ecoli fHbp+NMB0313+ | 2 | 33 | >524288 |
| 5 | OMV Ecoli fHbp+NMB0313+ | 2 | 34 | >524288 |
| 5 | OMV Ecoli fHbp+NMB0313+ | 2 | 35 | 32768 |
| 5 | OMV Ecoli fHbp+NMB0313+ | 2 | 36 | 16384 |
| 5 | OMV Ecoli fHbp+NMB0313+ | 2 | 37 | >524288 |
| 5 | OMV Ecoli fHbp+NMB0313+ | 2 | 38 | >524288 |
| 5 | OMV Ecoli fHbp+NMB0313+ | 2 | 39 | >524288 |
| 5 | OMV Ecoli fHbp+NMB0313+ | 2 | 40 | >524288 |
| 6 | OMV Ecoli fHbp+NMB0313+ | 0.2 | 41 | >524288 |
| 6 | OMV Ecoli fHbp+NMB0313+ | 0.2 | 42 | 16384 |
| 6 | OMV Ecoli fHbp+NMB0313+ | 0.2 | 43 | >524288 |
| 6 | OMV Ecoli fHbp+NMB0313+ | 0.2 | 44 | >524288 |
| 6 | OMV Ecoli fHbp+NMB0313+ | 0.2 | 45 | >524288 |
| 6 | OMV Ecoli fHbp+NMB0313+ | 0.2 | 46 | >524288 |
| 6 | OMV Ecoli fHbp+NMB0313+ | 0.2 | 47 | >524288 |
| 6 | OMV Ecoli fHbp+NMB0313+ | 0.2 | 48 | 16384 |
| 7 | fHbpv1.1 | 1 | 49 | 8192 |
| 7 | fHbpv1.1 | 1 | 50 | 8192 |
| 7 | fHbpv1.1 | 1 | 51 | <128 |
| 7 | fHbpv1.1 | 1 | 52 | 4096 |
| 7 | fHbpv1.1 | 1 | 53 | 32768 |
| 7 | fHbpv1.1 | 1 | 54 | 16384 |
| 7 | fHbpv1.1 | 1 | 55 | 8192 |
| 7 | fHbpv1.1 | 1 | 56 | 2048 |

*FIG. 14B*

| Antigen Dose | OMV(E.coli)fhbP-NMB0313- 2ug Alum OH 3 mg/ml | OMV(E.coli)fhbP-NMB0313+ 2ug Alum OH 3 mg/ml | OMV(E.coli)NHB A+ 2ug Alum OH 3 mg/ml | OMV(E.coli)NHB A+NMB0313+ 2ug Alum OH 3 mg/ml | NHBP Ap2 1ug Alum OH 3 mg/ml |
|---|---|---|---|---|---|
| topi | Gr. 1 | Gr. 2 | Gr. 8 | Gr. 9 | Gr. 10 |
| 1 | 4 | 4 | 124 | 634 | 134 |
| 2 | 5 | 4 | 79 | 275 | 114 |
| 3 | 2 | 5 | 16 | 288 | 18 |
| 4 | 4 | 5 | 6 | 237 | 193 |
| 5 | 2 | 5 | 7 | 165 | 39 |
| 6 | 2 | 5 | | | 12 |
| 7 | 4 | 1 | | | 110 |
| 8 | 4 | 1 | | | 140 |
| GMT | 3 | 3 | 23 | 287 | 67 |
| C.V. | 35 | 47 | 114 | 57 | 57 |

*FIG. 15B*

| Experimental Group | Treatment 1 | | Animal | rSBA pool rabbit complement lot 6352 |
|---|---|---|---|---|
| | ID | Quantity (ug) | | H44/76 |
| 8 | OMV Ecoli NHBA+ | 2 | 57 | <16 |
| 8 | OMV Ecoli NHBA+ | 2 | 58 | 128 |
| 8 | OMV Ecoli NHBA+ | 2 | 59 | <16 |
| 8 | OMV Ecoli NHBA+ | 2 | 60 | <16 |
| 8 | OMV Ecoli NHBA+ | 2 | 61 | <16 |
| 9 | OMV Ecoli NHBA+NMB0313 | 2 | 62 | 16384 |
| 9 | OMV Ecoli NHBA+NMB0313 | 2 | 63 | 2048 |
| 9 | OMV Ecoli NHBA+NMB0313 | 2 | 64 | 1024 |
| 9 | OMV Ecoli NHBA+NMB0313 | 2 | 65 | 2048 |
| 9 | OMV Ecoli NHBA+NMB0313 | 2 | 66 | 256 |
| 10 | NHBA p 2 | 1 | 67 | 256 |
| 10 | NHBA p 2 | 1 | 68 | 128 |
| 10 | NHBA p 2 | 1 | 69 | <16 |
| 10 | NHBA p 2 | 1 | 70 | 1024 |
| 10 | NHBA p 2 | 1 | 71 | contaminated |
| 10 | NHBA p 2 | 1 | 72 | contaminated |
| 10 | NHBA p 2 | 1 | 73 | contaminated |
| 10 | NHBA p 2 | 1 | 74 | 256 |

FIG. 17B

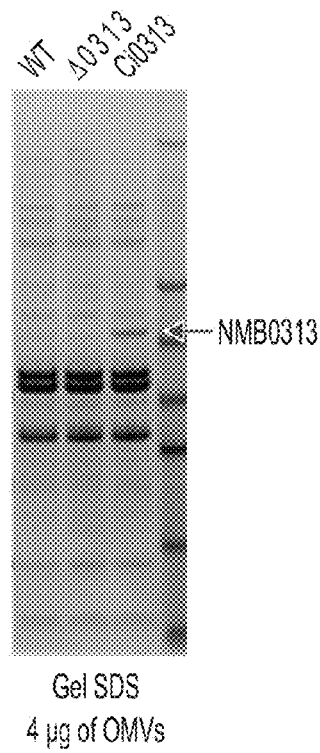
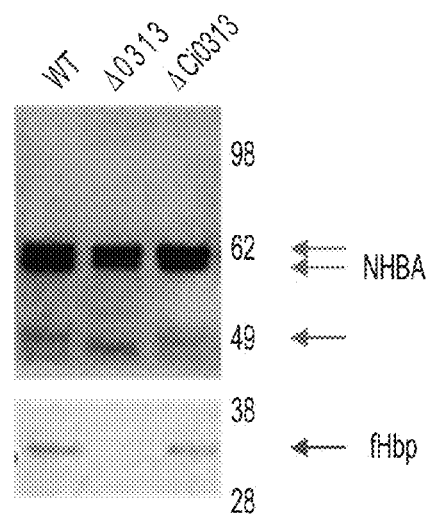
FIG. 19A  FIG. 19B
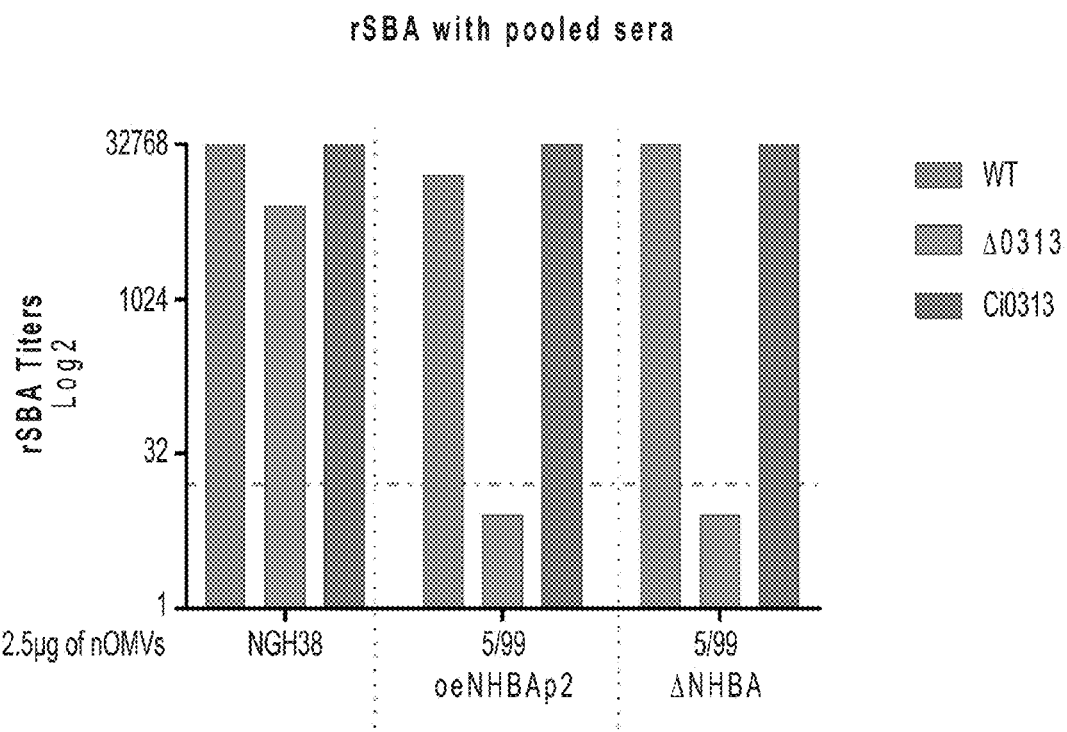
FIG. 20

| EXPERIMENTAL GROUP | TEST FORMULATION | TREATMENT 1 ID | QUANTITY (ug) | ADJUVANT 1 ID | QUANTITY | FINAL VOLUME | STORAGE CONDITIONS | rSBA POOL RABBIT COMPLEMENT LOT 6352 | | | | |
|---|---|---|---|---|---|---|---|---|---|---|---|---|
| | | | | | | | | H44776 | 5/99oeNHBAp2 | NGH38 | M4407 | 5/99AA ANIMAL GROUP |
| 1 | A | OMV Ecoli fHbp-NMB0313- | | 2Al(OH)3 | 3mg/ml | 200 µl | +5° | <16 | <16 | <16 | <16 | 8 |
| 2 | B | OMV Ecoli NMB0313+ | | 2Al(OH)3 | 3mg/ml | 200 µl | +5° | <16 | <16 | <16 | <16 | 8 |
| 3 | C | OMV Ecoli fHbp+ | | 2Al(OH)3 | 3mg/ml | 200 µl | +5° | 65536 | ND | ND | ND | 8 |
| 4 | D | OMV Ecoli fHbp+ | | 0.2Al(OH)3 | 3mg/ml | 200 µl | +5° | 8192 | ND | ND | ND | 8 |
| 5 | E | OMV Ecoli fHbp+NMB0313+ | | 2Al(OH)3 | 3mg/ml | 200 µl | +5° | 524288 | ND | ND | ND | 8 |
| 6 | F | OMV Ecoli fHbp+NMB0313+ | | 0.2Al(OH)3 | 3mg/ml | 200 µl | +5° | 524288 | ND | ND | ND | 8 |
| 7 | G | fHbpv1.1 | | 1Al(OH)3 | 3mg/ml | 200 µl | +5° | 16384 | ND | ND | ND | 5 |
| 8 | H | OMV Ecoli NHBA+ | | 2Al(OH)3 | 3mg/ml | 200 µl | +5° | ND | <16 | <16 | <16 | 5 |
| 9 | I | OMV Ecoli NHBA+NMB0313 | | 2Al(OH)3 | 3mg/ml | 200 µl | +5° | ND | 8192 | 4096* | 2048 | 5 |
| 10 | J | NHBA p 2 | | 1Al(OH)3 | 3mg/ml | 200 µl | +5° | ND | 256 | 512 | 256 | 8 |
| 11 | K | NHBA p 2 | | 20Al(OH)3 | 3mg/ml | 200 µl | +5° | ND | 8192 | 8192 | 8192 | 8 |

| EXPERIMENTAL GROUP | TEST FORMULATION | TREATMENT 1 ID | QUANTITY (ug) | rSBA POOL RABBIT COMPLEMENT LOT 6352 | |
|---|---|---|---|---|---|
| | | | | 5/99oeNHBAp2 | 5/99AA |
| 1 | A | OMV Ecoli fHBP-NMB0313- | 2 | <16 | <16 |
| 2 | B | OMV Ecoli NMB0313+ | 2 | <16 | <16 |
| 8 | H | OMV Ecoli NHBA+ | 2 | <16 | <16 |
| 9 | I | OMV Ecoli NHBA+NMB0313 | 2 | 8192 | <16 |
| 10 | J | NHBA p 2 | 1 | 256 | <16 |
| 11 | K | NHBA p 2 | 20 | 8192 | <16 |

FIG. 21A

| EXPERIMENTAL GROUP | TEST FORMULATION | TREATMENT 1 ID | QUANTITY (μg) | ADJUVANT 1 ID | FINAL VOLUME | rSBA POOL RABBIT COMPLEMENT LOT 6352 | | | | | | | | | |
|---|---|---|---|---|---|---|---|---|---|---|---|---|---|---|---|
| | | | | | | NZ | UK104 | UK414 | UK320 | NGH38 | M4407 | 5/99αα NHBp2 | 5/99AA | D8221 | DE11422 | DE11264 |
| 1 | A | OMVNZ_OE0460L_3KO | | 2.5Al(OH)3 | 200 μl | 2048 | 8192 | 1024* | 8192 | 8192 | ND | <16 | ND | ND | ND | ND |
| 2 | B | OMVNZ_OE0460L_3KO | | 0.5Al(OH)3 | 200 μl | 512 | 4096 | <16 | 512 | 4096 | ND | <16 | ND | ND | ND | ND |
| 3 | C | OMVNZ_OE0460L_OENMB0313_3KO | | 2.5Al(OH)3 | 200 μl | 2048 | 8192 | <16 | 1024 | 2048* | ND | 128* | ND | ND | ND | ND |
| 4 | D | OMVNZ_OE0460L_OENMB0313_3KO | | 0.5Al(OH)3 | 200 μl | 1024 | 16 | <16 | <16 | 1024* | ND | <16 | ND | ND | ND | ND |
| 5 | E | OMVNZ_OE0460L_2KO | | 2.5Al(OH)3 | 200 μl | 2048 | 2048 | <16 | 2048 | 4096* | ND | 256* | ND | ND | ND | ND |
| 6 | F | OMVNZ_OE0460L_2KO | | 0.5Al(OH)3 | 200 μl | 1024 | 4096 | <16 | 4096 | 2048 | ND | <16 | ND | ND | ND | ND |
| 7 | G | OMVNZ_OE0460_deltaNMB0313_2KO | | 2.5Al(OH)3 | 200 μl | 512 | 4096 | <16 | 4096 | 8192* | ND | 256* | ND | ND | ND | ND |
| 8 | H | OMVNZ_OE0460_deltaNMB0313_2KO | | 0.5Al(OH)3 | 200 μl | 512 | 1024 | <16 | 2048 | 4096* | ND | <16 | ND | ND | ND | ND |

| | | | | | | | | | |
|---|---|---|---|---|---|---|---|---|---|
| 9 | I | OMVNZ_3KO | 2.5Al(OH)3 | 200 μl | 8192 | >8192 | 512 | 4096 | 4096* <1 | <16 | NON TESTABILE MUORE IL <16 CEPPO |
| 10 | J | OMVNGH38 | 2.5Al(OH)3 | 200 μl | <16 | ND | ND | ND | 6 | 1024 | 16384 | <16 | NON TESTABILE MUORE IL <16 CEPPO |
| 11 | K | OMVNGH38_deltaNMB0313 | 2.5Al(OH)3 | 200 μl | 16 | ND | ND | ND | 262144 | <16 | | 32768 | <16 | NON TESTABILE MUORE IL 16 CEPPO |
| | | | 2.5Al(OH)3 | 200 μl | <16 | ND | ND | ND | 8192 | <16 | <16 | <16 | 16 | NON TESTABILE MUORE IL 16 CEPPO |
| 12 | L | OMVNGH38_CNMB0313 | 2.5Al(OH)3 | 200 μl | <16 | ND | ND | ND | 262144 | <16 | 32768 | 65536 | <16 | 16 CEPPO |
| sch624-1 | | GMMA3KO | 2.5Al(OH)3 | 200 μl | | | | | <16 | <16 | <16 | <16 | <16 | |

*FROM FIG. 21B*

FIG. 21C

| STUDY ID | ARM | ARMCD TREATMENT 1 | | DOSE ADJUVANT 1 | | SUBJID | LBTEST | | |
|---|---|---|---|---|---|---|---|---|---|
| EXPERIMENTAL ANIMAL | TEST FORMULATION | AG | QUANTITY (ug) | ID | QUANTITY | FINAL VOLUME | ELISA 936-741 | ELISA 287-953 |
| 1 | A | OMV Ecoli fHbp-NMB0313- | 2 | Al(OH)3 | 3mg/ml | 8 200 μl | 1 | 4 |
| 2 | A | OMV Ecoli fHbp-NMB0313- | 2 | Al(OH)3 | 3mg/ml | 8 200 μl | 1 | 5 |
| 3 | A | OMV Ecoli fHbp-NMB0313- | 2 | Al(OH)3 | 3mg/ml | 8 200 μl | 1 | 2 |
| 4 | A | OMV Ecoli fHbp-NMB0313- | 2 | Al(OH)3 | 3mg/ml | 8 200 μl | 1 | 4 |
| 5 | A | OMV Ecoli fHbp-NMB0313- | 2 | Al(OH)3 | 3mg/ml | 8 200 μl | 1 | 2 |
| 6 | A | OMV Ecoli fHbp-NMB0313- | 2 | Al(OH)3 | 3mg/ml | 8 200 μl | 1 | 2 |
| 7 | A | OMV Ecoli fHbp-NMB0313- | 2 | Al(OH)3 | 3mg/ml | 8 200 μl | 1 | 4 |
| 8 | A | OMV Ecoli fHbp-NMB0313- | 2 | Al(OH)3 | 3mg/ml | 8 200 μl | 1 | 4 |
|   |   |   |   |   |   | GMT | 1 | 3 |
| 9 | B | OMV Ecoli NMB0313+ | 2 | Al(OH)3 | 3mg/ml | 8 200 μl | 6 | 4 |
| 10 | B | OMV Ecoli NMB0313+ | 2 | Al(OH)3 | 3mg/ml | 200 μl | 7 | 4 |
| 11 | B | OMV Ecoli NMB0313+ | 2 | Al(OH)3 | 3mg/ml | 200 μl | 9 | 5 |
| 12 | B | OMV Ecoli NMB0313+ | 2 | Al(OH)3 | 3mg/ml | 200 μl | 8 | 5 |
| 13 | B | OMV Ecoli NMB0313+ | 2 | Al(OH)3 | 3mg/ml | 200 μl | 7 | 5 |
| 14 | B | OMV Ecoli NMB0313+ | 2 | Al(OH)3 | 3mg/ml | 200 μl | 7 | 5 |
| 15 | B | OMV Ecoli NMB0313+ | 2 | Al(OH)3 | 3mg/ml | 200 μl | 3 | 1 |
| 16 | B | OMV Ecoli NMB0313+ | 2 | Al(OH)3 | 3mg/ml | 200 μl | 2 | 1 |
|   |   |   |   |   |   | GMT | 6 | 3 |
| 17 | C | OMV Ecoli fHbp+ | 2 | Al(OH)3 | 3mg/ml | 200 μl | 1702 | ND |
| 18 | C | OMV Ecoli fHbp+ | 2 | Al(OH)3 | 3mg/ml | 200 μl | 118 | ND |
| 19 | C | OMV Ecoli fHbp+ | 2 | Al(OH)3 | 3mg/ml | 200 μl | 1478 | ND |
| 20 | C | OMV Ecoli fHbp+ | 2 | Al(OH)3 | 3mg/ml | 200 μl | 1448 | ND |
| 21 | C | OMV Ecoli fHbp+ | 2 | Al(OH)3 | 3mg/ml | 200 μl | 799 | ND |
| 22 | C | OMV Ecoli fHbp+ | 2 | Al(OH)3 | 3mg/ml | 200 μl | 1404 | ND |
| 23 | C | OMV Ecoli fHbp+ | 2 | Al(OH)3 | 3mg/ml | 200 μl | 916 | ND |
| 24 | C | OMV Ecoli fHbp+ | 2 | Al(OH)3 | 3mg/ml | 200 μl | 1647 | ND |
|   |   |   |   |   |   | GMT | 961 | ND |
| 25 | D | OMV Ecoli fHbp+ | 0.2 | Al(OH)3 | 3mg/ml | 200 μl | 240 | ND |
| 26 | D | OMV Ecoli fHbp+ | 0.2 | Al(OH)3 | 3mg/ml | 200 μl | 10 | ND |
| 27 | D | OMV Ecoli fHbp+ | 0.2 | Al(OH)3 | 3mg/ml | 200 μl | 8 | ND |
| 28 | D | OMV Ecoli fHbp+ | 0.2 | Al(OH)3 | 3mg/ml | 200 μl | 46 | ND |

↓ FROM FIG. 21D

| | | | | | |
|---|---|---|---|---|---|
| 29 | D | OMV Ecoli fHbp+ | 0.2 Al(OH)3 | 3mg/ml | 200 µl | 2 | ND |
| 30 | D | OMV Ecoli fHbp+ | 0.2 Al(OH)3 | 3mg/ml | 200 µl | 26 | ND |
| 31 | D | OMV Ecoli fHbp+ | 0.2 Al(OH)3 | 3mg/ml | 200 µl | 73 | ND |
| 32 | D | OMV Ecoli fHbp+ | 0.2 Al(OH)3 | 3mg/ml | 200 µl | 1 | ND |
| | | | | | GMT | 16 | |
| 33 | E | OMV Ecoli fHbp+NMB0313+ | 2 Al(OH)3 | 3mg/ml | 200 µl | 8629 | ND |
| 34 | E | OMV Ecoli fHbp+NMB0313+ | 2 Al(OH)3 | 3mg/ml | 200 µl | 7547 | ND |
| 35 | E | OMV Ecoli fHbp+NMB0313+ | 2 Al(OH)3 | 3mg/ml | 200 µl | 373 | ND |
| 36 | E | OMV Ecoli fHbp+NMB0313+ | 2 Al(OH)3 | 3mg/ml | 200 µl | 114 | ND |
| 37 | E | OMV Ecoli fHbp+NMB0313+ | 2 Al(OH)3 | 3mg/ml | 200 µl | 8477 | ND |
| 38 | E | OMV Ecoli fHbp+NMB0313+ | 2 Al(OH)3 | 3mg/ml | 200 µl | 4991 | ND |
| 39 | E | OMV Ecoli fHbp+NMB0313+ | 2 Al(OH)3 | 3mg/ml | 200 µl | 4587 | ND |
| 40 | E | OMV Ecoli fHbp+NMB0313+ | 2 Al(OH)3 | 3mg/ml | 200 µl | 3558 | ND |
| | | | | | GMT | 2572 | |
| 41 | F | OMV Ecoli fHbp+NMB0313+ | 0.2 Al(OH)3 | 3mg/ml | 200 µl | 7288 | ND |
| 42 | F | OMV Ecoli fHbp+NMB0313+ | 0.2 Al(OH)3 | 3mg/ml | 200 µl | 155 | ND |
| 43 | F | OMV Ecoli fHbp+NMB0313+ | 0.2 Al(OH)3 | 3mg/ml | 200 µl | 6739 | ND |
| 44 | F | OMV Ecoli fHbp+NMB0313+ | 0.2 Al(OH)3 | 3mg/ml | 200 µl | 3754 | ND |
| 45 | F | OMV Ecoli fHbp+NMB0313+ | 0.2 Al(OH)3 | 3mg/ml | 200 µl | 4136 | ND |
| 46 | F | OMV Ecoli fHbp+NMB0313+ | 0.2 Al(OH)3 | 3mg/ml | 200 µl | 12128 | ND |
| 47 | F | OMV Ecoli fHbp+NMB0313+ | 0.2 Al(OH)3 | 3mg/ml | 200 µl | 5529 | ND |
| 48 | F | OMV Ecoli fHbp+NMB0313+ | 0.2 Al(OH)3 | 3mg/ml | 200 µl | 2 | ND |
| | | | | | GMT | 1413 | |
| 49 | G | fHbpv1.1 | 1 Al(OH)3 | 3mg/ml | 200 µl | 1649 | ND |
| 50 | G | fHbpv1.1 | 1 Al(OH)3 | 3mg/ml | 200 µl | 1933 | ND |
| 51 | G | fHbpv1.1 | 1 Al(OH)3 | 3mg/ml | 200 µl | 1301 | ND |
| 52 | G | fHbpv1.1 | 1 Al(OH)3 | 3mg/ml | 200 µl | 1721 | ND |
| 53 | G | fHbpv1.1 | 1 Al(OH)3 | 3mg/ml | 200 µl | 1595 | ND |
| 54 | G | fHbpv1.1 | 1 Al(OH)3 | 3mg/ml | 200 µl | 186 | ND |
| 55 | G | fHbpv1.1 | 1 Al(OH)3 | 3mg/ml | 200 µl | 1273 | ND |
| 56 | G | fHbpv1.1 | 1 Al(OH)3 | 3mg/ml | 200 µl | 2163 | ND |
| | | | | | GMT | 1247 | |

FROM FIG. 21E

| | | | | | |
|---|---|---|---|---|---|
| 57 | H | OMV Ecoli NHBA+ | 2 Al(OH)3 | 3mg/ml | 200 µl | 124 |
| 58 | H | OMV Ecoli NHBA+ | 2 Al(OH)3 | 3mg/ml | 200 µl | 79 |
| 59 | H | OMV Ecoli NHBA+ | 2 Al(OH)3 | 3mg/ml | 200 µl | 16 |
| 60 | H | OMV Ecoli NHBA+ | 2 Al(OH)3 | 3mg/ml | 200 µl | 6 |
| 61 | H | OMV Ecoli NHBA+ | 2 Al(OH)3 | 3mg/ml | 200 µl | 7 |
| | | | | | GMT | 23 |
| 62 | I | OMV Ecoli NHBA+NMB0313 | 2 Al(OH)3 | 3mg/ml | 200 µl | ND | 634 |
| 63 | I | OMV Ecoli NHBA+NMB0313 | 2 Al(OH)3 | 3mg/ml | 200 µl | ND | 275 |
| 64 | I | OMV Ecoli NHBA+NMB0313 | 2 Al(OH)3 | 3mg/ml | 200 µl | ND | 288 |
| 65 | I | OMV Ecoli NHBA+NMB0313 | 2 Al(OH)3 | 3mg/ml | 200 µl | ND | 237 |
| 66 | I | OMV Ecoli NHBA+NMB0313 | 2 Al(OH)3 | 3mg/ml | 200 µl | ND | 165 |
| | | | | | GMT | 287 |
| 67 | J | NHBA p 2 | 1 Al(OH)3 | 3mg/ml | 200 µl | ND | 134 |
| 68 | J | NHBA p 2 | 1 Al(OH)3 | 3mg/ml | 200 µl | ND | 114 |
| 69 | J | NHBA p 2 | 1 Al(OH)3 | 3mg/ml | 200 µl | ND | 18 |
| 70 | J | NHBA p 2 | 1 Al(OH)3 | 3mg/ml | 200 µl | ND | 193 |
| 71 | J | NHBA p 2 | 1 Al(OH)3 | 3mg/ml | 200 µl | ND | 39 |
| 72 | J | NHBA p 2 | 1 Al(OH)3 | 3mg/ml | 200 µl | ND | 12 |
| 73 | J | NHBA p 2 | 1 Al(OH)3 | 3mg/ml | 200 µl | ND | 110 |
| 74 | J | NHBA p 2 | 1 Al(OH)3 | 3mg/ml | 200 µl | ND | 140 |
| | | | | | GMT | 67 |
| 75 | K | NHBA p 2 | 20 Al(OH)3 | 3mg/ml | 200 µl | ND | 1186 |
| 76 | K | NHBA p 2 | 20 Al(OH)3 | 3mg/ml | 200 µl | ND | 270 |
| 77 | K | NHBA p 2 | 20 Al(OH)3 | 3mg/ml | 200 µl | ND | 692 |
| 78 | K | NHBA p 2 | 20 Al(OH)3 | 3mg/ml | 200 µl | ND | 963 |
| 79 | K | NHBA p 2 | 20 Al(OH)3 | 3mg/ml | 200 µl | ND | 249 |
| 80 | K | NHBA p 2 | 20 Al(OH)3 | 3mg/ml | 200 µl | ND | 595 |
| 81 | K | NHBA p 2 | 20 Al(OH)3 | 3mg/ml | 200 µl | ND | 66 |
| 82 | K | NHBA p 2 | 20 Al(OH)3 | 3mg/ml | 200 µl | ND | 984 |
| | | | | | | | 461 |

ND= TO BE TESTED AS POOL

| | | | | | | | |
|---|---|---|---|---|---|---|---|
| 74 | J | OMVNGH38 | 2.5 Al(OH)3 | 200 μl | 1 | 1 | ND |
| 75 | J | OMVNGH38 | 2.5 Al(OH)3 | 200 μl | 1 | 1 | ND |
| 76 | J | OMVNGH38 | 2.5 Al(OH)3 | 200 μl | 1 | 1 | ND |
| 77 | J | OMVNGH38 | 2.5 Al(OH)3 | 200 μl | 1 | 1 | ND |
| 78 | J | OMVNGH38 | 2.5 Al(OH)3 | 200 μl | 1 | 1 | ND |
| 79 | J | OMVNGH38 | 2.5 Al(OH)3 | 200 μl | 1 | 1 | ND |
| 80 | J | OMVNGH38 | 2.5 Al(OH)3 | 200 μl | 1 | 1 | ND |
| | | | | GMT | 1 | 1 | |
| 81 | K | OMVNGH38_deltaNMB0313 | 2.5 Al(OH)3 | 200 μl | 1 | 1 | ND |
| 82 | K | OMVNGH38_deltaNMB0313 | 2.5 Al(OH)3 | 200 μl | 1 | 1 | ND |
| 83 | K | OMVNGH38_deltaNMB0313 | 2.5 Al(OH)3 | 200 μl | 1 | 1 | ND |
| 84 | K | OMVNGH38_deltaNMB0313 | 2.5 Al(OH)3 | 200 μl | 1 | 1 | ND |
| 85 | K | OMVNGH38_deltaNMB0313 | 2.5 Al(OH)3 | 200 μl | 1 | 1 | ND |
| 86 | K | OMVNGH38_deltaNMB0313 | 2.5 Al(OH)3 | 200 μl | 1 | 1 | ND |
| 87 | K | OMVNGH38_deltaNMB0313 | 2.5 Al(OH)3 | 200 μl | 1 | 1 | ND |
| 88 | K | OMVNGH38_deltaNMB0313 | 2.5 Al(OH)3 | 200 μl | 1 | 1 | ND |
| | | | | GMT | 1 | 1 | |
| 89 | L | OMVNGH38_CiNMB0313 | 2.5 Al(OH)3 | 200 μl | 1 | 1 | ND |
| 90 | L | OMVNGH38_CiNMB0313 | 2.5 Al(OH)3 | 200 μl | 1 | 1 | ND |
| 91 | L | OMVNGH38_CiNMB0313 | 2.5 Al(OH)3 | 200 μl | 1 | 1 | ND |
| 92 | L | OMVNGH38_CiNMB0313 | 2.5 Al(OH)3 | 200 μl | 1 | 1 | ND |
| 93 | L | OMVNGH38_CiNMB0313 | 2.5 Al(OH)3 | 200 μl | 1 | 1 | ND |
| 94 | L | OMVNGH38_CiNMB0313 | 2.5 Al(OH)3 | 200 μl | 1 | 1 | ND |
| 95 | L | OMVNGH38_CiNMB0313 | 2.5 Al(OH)3 | 200 μl | 1 | 1 | ND |
| 96 | L | OMVNGH38_CiNMB0313 | 2.5 Al(OH)3 | 200 μl | 1 | 1 | ND |
| | | | | GMT | 1 | 1 | |

*FIG. 21G*

| EXPERIMENTAL GROUP | TEST FORMULATION | TREATMENT 1 ID | QUANTITY (μg) | ADJUVANT 1 ID | QUANTITY | FINAL VOLUME | STORAGE CONDITIONS | ANIMAL | rSBA POOL RABBIT COMPLEMENT LOT 6352 H4476 | NGH38 | 5/99eNHBAp2 |
|---|---|---|---|---|---|---|---|---|---|---|---|
| 3 | C | OMV Ecoli fHbp+ | 2 | Al(OH)3 | 3mg/ml | 200 μl | +5° | 17 | 131072 | | |
| 3 | C | OMV Ecoli fHbp+ | 2 | Al(OH)3 | 3mg/ml | 200 μl | +5° | 18 | 8192 | | |
| 3 | C | OMV Ecoli fHbp+ | 2 | Al(OH)3 | 3mg/ml | 200 μl | +5° | 19 | 131072 | | |
| 3 | C | OMV Ecoli fHbp+ | 2 | Al(OH)3 | 3mg/ml | 200 μl | +5° | 20 | 262144 | | |
| 3 | C | OMV Ecoli fHbp+ | 2 | Al(OH)3 | 3mg/ml | 200 μl | +5° | 21 | 262144 | | |
| 3 | C | OMV Ecoli fHbp+ | 2 | Al(OH)3 | 3mg/ml | 200 μl | +5° | 22 | >262144 | | |
| 3 | C | OMV Ecoli fHbp+ | 2 | Al(OH)3 | 3mg/ml | 200 μl | +5° | 23 | >262144 | | |
| 3 | C | OMV Ecoli fHbp+ | 2 | Al(OH)3 | 3mg/ml | 200 μl | +5° | 24 | 262144 | | |
| 3 | | | | | | | | MEDIAN POOL | 262144 65536 | | |
| 4 | D | OMV Ecoli fHbp+ | 0.2 | Al(OH)3 | 3mg/ml | 200 μl | +5° | 25 | 16384 | | |
| 4 | D | OMV Ecoli fHbp+ | 0.2 | Al(OH)3 | 3mg/ml | 200 μl | +5° | 26 | 4096 | | |
| 4 | D | OMV Ecoli fHbp+ | 0.2 | Al(OH)3 | 3mg/ml | 200 μl | +5° | 27 | 128 | | |
| 4 | D | OMV Ecoli fHbp+ | 0.2 | Al(OH)3 | 3mg/ml | 200 μl | +5° | 28 | 128 | | |
| 4 | D | OMV Ecoli fHbp+ | 0.2 | Al(OH)3 | 3mg/ml | 200 μl | +5° | 29 | <128 | | |
| 4 | D | OMV Ecoli fHbp+ | 0.2 | Al(OH)3 | 3mg/ml | 200 μl | +5° | 30 | 8192 | | |
| 4 | D | OMV Ecoli fHbp+ | 0.2 | Al(OH)3 | 3mg/ml | 200 μl | +5° | 31 | 4096 | | |
| 4 | D | OMV Ecoli fHbp+ | 0.2 | Al(OH)3 | 3mg/ml | 200 μl | +5° | 32 | <128 | | |
| 4 | | | | | | | | MEDIAN POOL | 2176 8192 | | |
| 5 | E | OMV Ecoli fHbp+NMB0313+ | 2 | Al(OH)3 | 3mg/ml | 200 μl | +5° | 33 | >524288 | | |
| 5 | E | OMV Ecoli fHbp+NMB0313+ | 2 | Al(OH)3 | 3mg/ml | 200 μl | +5° | 34 | >524288 | | |
| 5 | E | OMV Ecoli fHbp+NMB0313+ | 2 | Al(OH)3 | 3mg/ml | 200 μl | +5° | 35 | 32768 | | |
| 5 | E | OMV Ecoli fHbp+NMB0313+ | 2 | Al(OH)3 | 3mg/ml | 200 μl | +5° | 36 | 16384 | | |
| 5 | E | OMV Ecoli fHbp+NMB0313+ | 2 | Al(OH)3 | 3mg/ml | 200 μl | +5° | 37 | >524288 | | |
| 5 | E | OMV Ecoli fHbp+NMB0313+ | 2 | Al(OH)3 | 3mg/ml | 200 μl | +5° | 38 | >524288 | | |
| 5 | E | OMV Ecoli fHbp+NMB0313+ | 2 | Al(OH)3 | 3mg/ml | 200 μl | +5° | 39 | >524288 | | |
| 5 | E | OMV Ecoli fHbp+NMB0313+ | 2 | Al(OH)3 | 3mg/ml | 200 μl | +5° | 40 | >524288 | | |
| 5 | | | | | | | | MEDIAN POOL | 1048576 524288 | | |
| 6 | F | OMV Ecoli fHbp+NMB0313+ | 0.2 | Al(OH)3 | 3mg/ml | 200 μl | +5° | 41 | >524288 | | |
| 6 | F | OMV Ecoli fHbp+NMB0313+ | 0.2 | Al(OH)3 | 3mg/ml | 200 μl | +5° | 42 | 16384 | | |
| 6 | F | OMV Ecoli fHbp+NMB0313+ | 0.2 | Al(OH)3 | 3mg/ml | 200 μl | +5° | 43 | >524288 | | |
| 6 | F | OMV Ecoli fHbp+NMB0313+ | 0.2 | Al(OH)3 | 3mg/ml | 200 μl | +5° | 44 | >524288 | | |
| 6 | F | OMV Ecoli fHbp+NMB0313+ | 0.2 | Al(OH)3 | 3mg/ml | 200 μl | +5° | 45 | >524288 | | |
| 6 | F | OMV Ecoli fHbp+NMB0313+ | 0.2 | Al(OH)3 | 3mg/ml | 200 μl | +5° | 46 | >524288 | | |
| 6 | F | OMV Ecoli fHbp+NMB0313+ | 0.2 | Al(OH)3 | 3mg/ml | 200 μl | +5° | 47 | >524288 | | |
| 6 | F | OMV Ecoli fHbp+NMB0313+ | 0.2 | Al(OH)3 | 3mg/ml | 200 μl | +5° | 48 | 16384 | | |

← FROM FIG. 21H

| Group | Antigen | Conc | Vol | Temp | Pool | Col A | Col B | Col C |
|---|---|---|---|---|---|---|---|---|
| 7 | fHbpv1.1 | 3mg/ml | 200 μl | +5° | 49 | 1048576 | | |
| 7 | fHbpv1.1 | 3mg/ml | 200 μl | +5° | 50 | 524288 | | |
| 7 | fHbpv1.1 | 3mg/ml | 200 μl | +5° | 51 | 8192 | | |
| 7 | fHbpv1.1 | 3mg/ml | 200 μl | +5° | 52 | 8192 | | |
| 7 | fHbpv1.1 | 3mg/ml | 200 μl | +5° | 53 | <128 | | |
| 7 | fHbpv1.1 | 3mg/ml | 200 μl | +5° | 54 | 4096 | | |
| 7 | fHbpv1.1 | 3mg/ml | 200 μl | +5° | 55 | 32768 | | |
| 7 | fHbpv1.1 | 3mg/ml | 200 μl | +5° | 56 | 16384 | | |
| | | | | | MEDIAN POOL | 8192 | | |
| 8 | OMV Ecoli NHBA+ | 3mg/ml | 200 μl | +5° | 57 | 2048 | <16 | <16 |
| 8 | OMV Ecoli NHBA+ | 3mg/ml | 200 μl | +5° | 58 | 8192 | <16 | 128 |
| 8 | OMV Ecoli NHBA+ | 3mg/ml | 200 μl | +5° | 59 | 16384 | <16 | <16 |
| 8 | OMV Ecoli NHBA+ | 3mg/ml | 200 μl | +5° | 60 | | <16 | <16 |
| 8 | OMV Ecoli NHBA | 3mg/ml | 200 μl | +5° | 61 | | <16 | <16 |
| | | | | | MEDIAN POOL | | <16 | <16 |
| 9 | OMV Ecoli NHBA+NMB0313 | 3mg/ml | 200 μl | +5° | 62 | | 4096 | 16384 |
| 9 | OMV Ecoli NHBA+NMB0313 | 3mg/ml | 200 μl | +5° | 63 | | <16 | 2048 |
| 9 | OMV Ecoli NHBA+NMB0313 | 3mg/ml | 200 μl | +5° | 64 | | <16 | 1027 |
| 9 | OMV Ecoli NHBA+NMB0313 | 3mg/ml | 200 μl | +5° | 65 | | <16 | 2048 |
| 9 | OMV Ecoli NHBA+NMB0313 | 3mg/ml | 200 μl | +5° | 66 | | 8 | 256 |
| | | | | | MEDIAN POOL | | 4096 | 2048 |
| 10 | NHBA p.2 | 3mg/ml | 200 μl | +5° | 67 | | 256 | 8192 |
| 10 | NHBA p.2 | 3mg/ml | 200 μl | +5° | 68 | | 64 | 256 |
| 10 | NHBA p.2 | 3mg/ml | 200 μl | +5° | 69 | | 64 | 128 |
| 10 | NHBA p.2 | 3mg/ml | 200 μl | +5° | 70 | | 1024* | <16 |
| 10 | NHBA p.2 | 3mg/ml | 200 μl | +5° | 71 | | 1024* | 1024 |
| 10 | NHBA p.2 | 3mg/ml | 200 μl | +5° | 72 | | <16 | CONTAMINATED |
| 10 | NHBA p.2 | 3mg/ml | 200 μl | +5° | 73 | | <16 | CONTAMINATED |
| 10 | NHBA p.2 | 3mg/ml | 200 μl | +5° | 74 | | 256 | CONTAMINATED |
| | | | | | MEDIAN POOL | | 160 | 256 |
| | | | | | | | 512 | 256 |
| | | | | | | | | 256 |

→ TO FIG. 21J

| EXPERIMENTAL GROUP | TEST FORMULATION | TREATMENT 1 ID | QUANTITY (ug) | ANIMAL | rSBA POOL RABBIT COMPLEMENT LOT 6352 H44/75 |
|---|---|---|---|---|---|
| 3 | C | OMV Ecoli fHbp+ | 2 | 17 | 131072 |
| 3 | C | OMV Ecoli fHbp+ | 2 | 18 | 8192 |
| 3 | C | OMV Ecoli fHbp+ | 2 | 19 | 131072 |
| 3 | C | OMV Ecoli fHbp+ | 2 | 20 | 262144 |
| 3 | C | OMV Ecoli fHbp+ | 2 | 21 | 262144 |
| 3 | C | OMV Ecoli fHbp+ | 2 | 22 | >262144 |
| 3 | C | OMV Ecoli fHbp+ | 2 | 23 | >262144 |
| 3 | C | OMV Ecoli fHbp+ | 2 | 24 | 262144 |
| 4 | D | OMV Ecoli fHbp+ | 0.2 | 25 | 161384 |
| 4 | D | OMV Ecoli fHbp+ | 0.2 | 26 | 4096 |
| 4 | D | OMV Ecoli fHbp+ | 0.2 | 27 | 128 |
| 4 | D | OMV Ecoli fHbp+ | 0.2 | 28 | 128 |
| 4 | D | OMV Ecoli fHbp+ | 0.2 | 29 | <128 |
| 4 | D | OMV Ecoli fHbp+ | 0.2 | 30 | 8192 |
| 4 | D | OMV Ecoli fHbp+ | 0.2 | 31 | 4096 |
| 4 | D | OMV Ecoli fHbp+ | 0.2 | 32 | <128 |
| 5 | E | OMV Ecoli fHbp+NMB0313+ | 2 | 33 | >524288 |
| 5 | E | OMV Ecoli fHbp+NMB0313+ | 2 | 34 | >524288 |
| 5 | E | OMV Ecoli fHbp+NMB0313+ | 2 | 35 | 32768 |
| 5 | E | OMV Ecoli fHbp+NMB0313+ | 2 | 36 | 16384 |
| 5 | E | OMV Ecoli fHbp+NMB0313+ | 2 | 37 | >524288 |
| 5 | E | OMV Ecoli fHbp+NMB0313+ | 2 | 38 | >=524288 |
| 5 | E | OMV Ecoli fHbp+NMB0313+ | 2 | 39 | >524288 |
| 5 | E | OMV Ecoli fHbp+NMB0313+ | 2 | 40 | >524288 |
| 6 | F | OMV Ecoli fHbp+NMB0313+ | 0.2 | 41 | >524288 |
| 6 | F | OMV Ecoli fHbp+NMB0313+ | 0.2 | 42 | 16384 |
| 6 | F | OMV Ecoli fHbp+NMB0313+ | 0.2 | 43 | >524288 |
| 6 | F | OMV Ecoli fHbp+NMB0313+ | 0.2 | 44 | >524288 |
| 6 | F | OMV Ecoli fHbp+NMB0313+ | 0.2 | 45 | >524288 |
| 6 | F | OMV Ecoli fHbp+NMB0313+ | 0.2 | 46 | >524288 |
| 6 | F | OMV Ecoli fHbp+NMB0313+ | 0.2 | 47 | >524288 |
| 6 | F | OMV Ecoli fHbp+NMB0313+ | 0.2 | 48 | 16384 |
| 7 | G | fHbpv1.1 | 1 | 49 | 8192 |
| 7 | G | fHbpv1.1 | 1 | 50 | 8192 |
| 7 | G | fHbpv1.1 | 1 | 51 | <128 |
| 7 | G | fHbpv1.1 | 1 | 52 | 4096 |
| 7 | G | fHbpv1.1 | 1 | 53 | 32769 |
| 7 | G | fHbpv1.1 | 1 | 54 | 16384 |
| 7 | G | fHbpv1.1 | 1 | 55 | 8192 |
| 7 | G | fHbpv1.1 | 1 | 56 | 2048 |

*FIG. 21K*

| EXPERIMENTAL GROUP | TEST FORMULATION | TREATMENT 1 ID | ADJUVANT 1 QUANTITY (ug) | ID | FINAL VOLUME | ANIMAL | rSBA POOL RABBIT COMPLEMENT LOT 6352 NGH38 |
|---|---|---|---|---|---|---|---|
| 10 | J | OMVNGH38 | 2.5 | Al(OH)3 | 200 μl | 73 | >262144 |
| 10 | J | OMVNGH38 | 2.5 | Al(OH)3 | 200 μl | 74 | >262144 |
| 10 | J | OMVNGH38 | 2.5 | Al(OH)3 | 200 μl | 75 | 16382 |
| 10 | J | OMVNGH38 | 2.5 | Al(OH)3 | 200 μl | 76 | 65563 |
| 10 | J | OMVNGH38 | 2.5 | Al(OH)3 | 200 μl | 77 | 65536 |
| 10 | J | OMVNGH38 | 2.5 | Al(OH)3 | 200 μl | 78 | 262144 |
| 10 | J | OMVNGH38 | 2.5 | Al(OH)3 | 200 μl | 79 | 262144 |
| 10 | J | OMVNGH38 | 2.5 | Al(OH)3 | 200 μl | 80 | >262144 |
| | | | | | | MEDIAN | 262144 |
| | | | | | | POOL | 262144 |
| 11 | K | OMVNGH38_deltaNMB0313 | 2.5 | Al(OH)3 | 200 μl | 81 | 65536 |
| 11 | K | OMVNGH38_deltaNMB0313 | 2.5 | Al(OH)3 | 200 μl | 82 | 32768 |
| 11 | K | OMVNGH38_deltaNMB0313 | 2.5 | Al(OH)3 | 200 μl | 83 | 65536 |
| 11 | K | OMVNGH38_deltaNMB0313 | 2.5 | Al(OH)3 | 200 μl | 84 | 65536 |
| 11 | K | OMVNGH38_deltaNMB0313 | 2.5 | Al(OH)3 | 200 μl | 85 | 16364 |
| 11 | K | OMVNGH38_deltaNMB0313 | 2.5 | Al(OH)3 | 200 μl | 86 | 8192 |
| 11 | K | OMVNGH38_deltaNMB0313 | 2.5 | Al(OH)3 | 200 μl | 87 | 131072 |
| 11 | K | OMVNGH38_deltaNMB0313 | 2.5 | Al(OH)3 | 200 μl | 88 | 65536 |
| | | | | | | MEDIAN | 65536 |
| | | | | | | POOL | 8192 |
| 12 | L | OMVNGH38_CiNMB0313 | 2.5 | Al(OH)3 | 200 μl | 89 | >262144 |
| 12 | L | OMVNGH38_CiNMB0313 | 2.5 | Al(OH)3 | 200 μl | 90 | ND |
| 12 | L | OMVNGH38_CiNMB0313 | 2.5 | Al(OH)3 | 200 μl | 91 | 32768 |
| 12 | L | OMVNGH38_CiNMB0313 | 2.5 | Al(OH)3 | 200 μl | 92 | 32768 |
| 12 | L | OMVNGH38_CiNMB0313 | 2.5 | Al(OH)3 | 200 μl | 93 | >262144 |
| 12 | L | OMVNGH38_CiNMB0313 | 2.5 | Al(OH)3 | 200 μl | 94 | 32768 |
| 12 | L | OMVNGH38_CiNMB0313 | 2.5 | Al(OH)3 | 200 μl | 95 | 8192 |
| 12 | L | OMVNGH38_CiNMB0313 | 2.5 | Al(OH)3 | 200 μl | 96 | 131072 |
| | | | | | | MEDIAN | 32768 |
| | | | | | | POOL | 262144 |

SEQUENCE LISTING

<160> NUMBER OF SEQ ID NOS: 20

<210> SEQ ID NO 1
<211> LENGTH: 1467
<212> TYPE: DNA
<213> ORGANISM: Neisseria meningitidis

<400> SEQUENCE: 1

| | | |
|---|---|---|
| atggttattt tttatttttg tgggaagaca tttatgcctg cacgaaacag atggatgctg | 60 |
| ctgctgcctt tattggcaag cgcggcatat gccgaagaaa caccgcgcga accggatttg | 120 |
| agaagccgtc ccgagttcag gcttcatgaa gcggaggtca aaccgatcga cagggagaag | 180 |
| gtgccgggc aggtgcggga aaaggaaaa gttttgcaga ttgacggcga aaccctgctg | 240 |
| aaaaatcccg aattgttgtc ccgcgcgatg tattccgcag tggtctcaaa caatattgcc | 300 |
| ggtatccgcg ttattttgcc gatttaccta caacaggcgc agcaggataa gatgttggca | 360 |
| ctttatgcac aagggatttt ggcgcaggca gacggtaggg tgaaggaggc gatttcccat | 420 |
| taccgggaat tgattgccgc ccaacccgac gcgcccgccg tccgtatgcg tttggcggca | 480 |
| gcattgtttg aaaacaggca gaacgaggcg gcggcagacc agttcgaccg cctgaaggcg | 540 |
| gaaaacctgc cgccgcagct gatggagcag gtcgagctgt accgcaaggc attgcgcgaa | 600 |
| cgcgatgcgt ggaaggtaaa tggcggcttc agcgtcaccc gcaacacaa tatcaaccaa | 660 |
| gccccgaaac ggcagcagta cggcaaatgg actttcccga acaggtgga cggcacggcg | 720 |
| gtcaattacc ggctcggcgc ggagaaaaaa tggtcgctga aaaacggctg gtacacgacg | 780 |
| gcgggcggcg acgtgtccgg cagggtttat ccggggaata gaaattcaa cgatatgacg | 840 |
| gcaggcgttt ccggcggcat cggttttgcc gaccggcgca aagatgccgg gctggcagtg | 900 |
| ttccacgaac gccgcaccta cggcaacgac gcttattctt acaccaacgg cgcacgcctt | 960 |
| tatttcaacc gttggcaaac cccgaaatgg caaacgttgt cttcggcgga gtggggggcgt | 1020 |
| tgaagaata cgcgccgggc gcgttccgac aatacccatt gcaaatttc caattcgctg | 1080 |
| gtgttttacc ggaatgcgcg ccaatattgg atgggcggtt tggattttta ccgcagcgc | 1140 |
| aaccccgccg accggggcga caatttcaac cgttacggcc tgcgctttgc ctgggggcag | 1200 |
| gaatggggcg gcagcggcct gtcttcgctg ttgcgcctcg gcgcggcgaa acggcattat | 1260 |
| gaaaaacccg gctttttcag cggttttaaa ggggaaggc gcaggataa agaattgaac | 1320 |
| acatccttga gcctttggca ccgggcattg catttcaaag gcatcacgcc gcgcctgacg | 1380 |
| ttgtcgcacc gcgaaacgcg gagtaacgat gtgttcaacg aatacgagaa aaatcgggcg | 1440 |
| tttgtcgagt ttaataaaac gttctga | 1467 |

<210> SEQ ID NO 2
<211> LENGTH: 488
<212> TYPE: PRT
<213> ORGANISM: Neisseria meningitidis

<400> SEQUENCE: 2

Met Val Ile Phe Tyr Phe Cys Gly Lys Thr Phe Met Pro Ala Arg Asn
1               5                   10                  15

Arg Trp Met Leu Leu Pro Leu Leu Ala Ser Ala Ala Tyr Ala Glu
        20                  25                  30

Glu Thr Pro Arg Glu Pro Asp Leu Arg Ser Arg Pro Glu Phe Arg Leu
            35                  40                  45

His Glu Ala Glu Val Lys Pro Ile Asp Arg Glu Lys Val Pro Gly Gln
    50                  55                  60

```
Val Arg Glu Lys Gly Lys Val Leu Gln Ile Asp Gly Glu Thr Leu Leu
 65                  70                  75                  80

Lys Asn Pro Glu Leu Leu Ser Arg Ala Met Tyr Ser Ala Val Val Ser
                 85                  90                  95

Asn Asn Ile Ala Gly Ile Arg Val Ile Leu Pro Ile Tyr Leu Gln Gln
            100                 105                 110

Ala Gln Gln Asp Lys Met Leu Ala Leu Tyr Ala Gln Gly Ile Leu Ala
        115                 120                 125

Gln Ala Asp Gly Arg Val Lys Glu Ala Ile Ser His Tyr Arg Glu Leu
    130                 135                 140

Ile Ala Ala Gln Pro Asp Ala Pro Ala Val Arg Met Arg Leu Ala Ala
145                 150                 155                 160

Ala Leu Phe Glu Asn Arg Gln Asn Glu Ala Ala Asp Gln Phe Asp
                165                 170                 175

Arg Leu Lys Ala Glu Asn Leu Pro Pro Gln Leu Met Glu Gln Val Glu
            180                 185                 190

Leu Tyr Arg Lys Ala Leu Arg Glu Arg Asp Ala Trp Lys Val Asn Gly
        195                 200                 205

Gly Phe Ser Val Thr Arg Glu His Asn Ile Asn Gln Ala Pro Lys Arg
210                 215                 220

Gln Gln Tyr Gly Lys Trp Thr Phe Pro Lys Gln Val Asp Gly Thr Ala
225                 230                 235                 240

Val Asn Tyr Arg Leu Gly Ala Glu Lys Lys Trp Ser Leu Lys Asn Gly
                245                 250                 255

Trp Tyr Thr Thr Ala Gly Gly Asp Val Ser Gly Arg Val Tyr Pro Gly
            260                 265                 270

Asn Lys Lys Phe Asn Asp Met Thr Ala Gly Val Ser Gly Ile Gly
        275                 280                 285

Phe Ala Asp Arg Arg Lys Asp Ala Gly Leu Ala Val Phe His Glu Arg
    290                 295                 300

Arg Thr Tyr Gly Asn Asp Ala Tyr Ser Tyr Thr Asn Gly Ala Arg Leu
305                 310                 315                 320

Tyr Phe Asn Arg Trp Gln Thr Pro Lys Trp Gln Thr Leu Ser Ser Ala
                325                 330                 335

Glu Trp Gly Arg Leu Lys Asn Thr Arg Arg Ala Arg Ser Asp Asn Thr
            340                 345                 350

His Leu Gln Ile Ser Asn Ser Leu Val Phe Tyr Arg Asn Ala Arg Gln
        355                 360                 365

Tyr Trp Met Gly Gly Leu Asp Phe Tyr Arg Glu Arg Asn Pro Ala Asp
    370                 375                 380

Arg Gly Asp Asn Phe Asn Arg Tyr Gly Leu Arg Phe Ala Trp Gly Gln
385                 390                 395                 400

Glu Trp Gly Gly Ser Gly Leu Ser Ser Leu Arg Leu Gly Ala Ala
                405                 410                 415

Lys Arg His Tyr Glu Lys Pro Gly Phe Phe Ser Gly Phe Lys Gly Glu
            420                 425                 430

Arg Arg Arg Asp Lys Glu Leu Asn Thr Ser Leu Ser Leu Trp His Arg
        435                 440                 445

Ala Leu His Phe Lys Gly Ile Thr Pro Arg Leu Thr Leu Ser His Arg
    450                 455                 460

Glu Thr Arg Ser Asn Asp Val Phe Asn Glu Tyr Glu Lys Asn Arg Ala
465                 470                 475                 480
```

```
Phe Val Glu Phe Asn Lys Thr Phe
                485

<210> SEQ ID NO 3
<211> LENGTH: 505
<212> TYPE: PRT
<213> ORGANISM: N. meningitidis

<400> SEQUENCE: 3

Met Leu Tyr Phe Arg Tyr Gly Phe Leu Val Val Trp Cys Ala Ala Gly
1               5                   10                  15

Val Ser Ala Ala Tyr Gly Ala Asp Ala Pro Ala Ile Leu Asp Asp Lys
            20                  25                  30

Ala Leu Leu Gln Val Gln Arg Ser Val Ser Asp Lys Trp Ala Glu Ser
        35                  40                  45

Asp Trp Lys Val Glu Asn Asp Ala Pro Arg Val Val Asp Gly Asp Phe
    50                  55                  60

Leu Leu Ala His Pro Lys Met Leu Glu His Ser Leu Arg Asp Ala Leu
65                  70                  75                  80

Asn Gly Asn Gln Ala Asp Leu Ile Ala Ser Leu Ala Asp Leu Tyr Ala
                85                  90                  95

Lys Leu Pro Asp Tyr Asp Ala Val Leu Tyr Gly Arg Ala Arg Ala Leu
            100                 105                 110

Leu Ala Lys Leu Ala Gly Arg Pro Ala Glu Ala Val Ala Arg Tyr Arg
        115                 120                 125

Glu Leu His Gly Glu Asn Ala Ala Asp Glu Arg Ile Leu Leu Asp Leu
    130                 135                 140

Ala Ala Ala Glu Phe Asp Asp Phe Arg Leu Lys Ser Ala Glu Arg His
145                 150                 155                 160

Phe Ala Glu Ala Ala Lys Leu Asp Leu Pro Ala Pro Val Leu Glu Asn
                165                 170                 175

Val Gly Arg Phe Arg Lys Lys Thr Glu Gly Leu Thr Gly Trp Arg Phe
            180                 185                 190

Ser Gly Gly Ile Ser Pro Ala Val Asn Arg Asn Ala Asn Asn Ala Ala
        195                 200                 205

Pro Gln Tyr Cys Arg Gln Asn Gly Gly Arg Gln Ile Cys Ser Val Ser
    210                 215                 220

Arg Ala Glu Arg Ala Ala Gly Leu Asn Tyr Glu Ile Glu Ala Glu Lys
225                 230                 235                 240

Leu Thr Pro Leu Ala Asp Asn His Tyr Leu Leu Phe Arg Ser Asn Ile
                245                 250                 255

Gly Gly Thr Ser Tyr Tyr Phe Ser Lys Lys Ser Ala Tyr Asp Asp Gly
            260                 265                 270

Phe Gly Arg Ala Tyr Leu Gly Trp Gln Tyr Lys Asn Ala Arg Gln Thr
        275                 280                 285

Ala Gly Ile Leu Pro Phe Tyr Gln Val Gln Leu Ser Gly Ser Asp Gly
    290                 295                 300

Phe Asp Ala Lys Thr Lys Arg Val Asn Asn Arg Arg Leu Pro Pro Tyr
305                 310                 315                 320

Met Leu Ala His Gly Val Gly Val Gln Leu Ser His Thr Tyr Arg Pro
                325                 330                 335

Asn Pro Gly Trp Gln Phe Ser Val Ala Leu Glu His Tyr Arg Gln Arg
            340                 345                 350

Tyr Arg Glu Gln Asp Arg Ala Glu Tyr Asn Asn Gly Arg Gln Asp Gly
        355                 360                 365
```

```
Phe Tyr Val Ser Ser Ala Lys Arg Leu Gly Glu Ser Ala Thr Val Phe
        370                 375                 380

Gly Gly Trp Gln Phe Val Arg Phe Val Pro Lys Arg Glu Thr Val Gly
385                 390                 395                 400

Gly Ala Val Asn Asn Ala Ala Tyr Arg Arg Asn Gly Val Tyr Ala Gly
                405                 410                 415

Trp Ala Gln Glu Trp Arg Gln Leu Gly Gly Leu Asn Ser Arg Val Ser
                420                 425                 430

Ala Ser Tyr Ala Arg Arg Asn Tyr Lys Gly Ile Ala Ala Phe Ser Thr
            435                 440                 445

Glu Ala Gln Arg Asn Arg Glu Trp Asn Val Ser Leu Ala Leu Ser His
        450                 455                 460

Asp Lys Leu Ser Tyr Lys Gly Ile Val Pro Ala Leu Asn Tyr Arg Phe
465                 470                 475                 480

Gly Arg Thr Glu Ser Asn Val Pro Tyr Ala Lys Arg Arg Asn Ser Glu
                485                 490                 495

Val Phe Val Ser Ala Asp Trp Arg Phe
                500                 505

<210> SEQ ID NO 4
<211> LENGTH: 481
<212> TYPE: PRT
<213> ORGANISM: Streptococcus pneumoniae

<400> SEQUENCE: 4

Met Ser Ile Gln Thr Lys Phe Ile Leu Phe Leu Ser Ser Leu Phe
1               5                   10                  15

Leu Thr Pro Tyr Ser Val Ala Thr Glu Lys Ser Pro Gln Pro His Asp
                20                  25                  30

Gly Arg Leu Asp Glu Gln Leu His Leu Ala Lys Pro Asn Leu Pro Gln
            35                  40                  45

Lys Pro Thr Ala Leu Leu Thr Asn Asn Pro Ser Lys Leu Ser Ile
50                  55                  60

Thr Lys Glu Glu Leu Ala Lys His Pro Asp Leu Ile Ile Arg Gly Leu
65                  70                  75                  80

Ile Pro Ala Val Leu Gln Asn Asn Gly Glu Ala Val Gln Leu Leu Leu
                85                  90                  95

Pro Leu Tyr Gln Pro Leu Pro Lys Lys Asp Pro Phe Leu Leu Glu Trp
            100                 105                 110

Ala Glu Ala Ile Asp Leu Arg Glu Lys Gly His Phe Ser Asp Ser Val
        115                 120                 125

Lys Ala Tyr Arg His Leu Phe Ser Gln Lys Thr Asp Leu Leu Pro Leu
130                 135                 140

Arg Tyr Gln Leu Ala Gln Ala Leu Phe Leu Asn Asn Asp Asn Glu Ala
145                 150                 155                 160

Ala Lys Asp Gln Phe Gln Lys Leu Arg Ala Glu Gln Val Ser Pro Asp
                165                 170                 175

Ser Val Lys Ile Ile Glu Gln Tyr Leu Ser Ala Leu Asn Gln Arg Asp
            180                 185                 190

Gln Trp Lys Ile Gln Gly Gly Phe Ser Phe Leu Asn Glu Ser Asn Ile
        195                 200                 205

Asn Asn Ala Pro Lys Ala Gly Thr Lys Ile Gly Asn Trp Thr Ala Trp
210                 215                 220

Glu Lys Glu Ser Ala Arg Gly Phe Ser Tyr Phe Gly Asn Ala Glu Lys
```

```
                225                 230                 235                 240
Lys Trp Ser Leu Pro His Asn His Phe Thr Lys Leu Ser Leu Glu Gly
                    245                 250                 255
Ser Gly Lys Tyr Tyr Trp Asp Asn Lys Lys Tyr Asn Glu Phe Asn Ala
                    260                 265                 270
Arg Ala Gly Ala Gly Leu Gly Tyr Gln Thr Ala Arg Phe Glu Val Ser
                    275                 280                 285
Leu Met Pro Phe Thr Glu Lys Arg Trp Tyr Val Gly Gly Ser Ser Gly
        290                 295                 300
Gly Asn Ala Met Lys Gln Tyr Ser Lys Asn Ser Gly Ala Arg Leu Asp
305                 310                 315                 320
Leu Ser Asn Trp Leu Asn Glu Lys Trp Gln Ile Ser Thr Ala Leu Glu
                325                 330                 335
Tyr Gly Glu Gln Arg Tyr Glu Thr Arg Lys His Leu Asn Gly Asn Asn
                    340                 345                 350
Tyr Leu Ala Ser Ala Thr Leu Leu Tyr Leu Ala Lys Ser Gly Gln Tyr
                    355                 360                 365
Trp Phe Gly Gly Ala Asp Tyr Asn Arg Glu Asn Thr Arg Asp Leu Asp
        370                 375                 380
Asn Ala Tyr Gln Arg Lys Asn Val Arg Leu Gly Trp Gly Gln Glu Trp
385                 390                 395                 400
Lys Ala Gly Ile Ser Thr Arg Leu Ile Leu Asn Tyr Ala Arg Arg Ala
                    405                 410                 415
Tyr Lys Glu Lys Asp Leu Ile Gly Ile Arg Gln Lys Asn Lys Glu Tyr
                    420                 425                 430
Ala Ser Val Phe Thr Ile Trp His Arg Asn Phe His Ile Trp Gly Ile
                    435                 440                 445
Thr Pro Lys Leu Ser Trp Ser Tyr Gln Lys Val Thr Ser Asn His Pro
            450                 455                 460
Phe Tyr Glu Tyr Asp Lys Asn Arg Ile Tyr Val Glu Ile Ser Lys Thr
465                 470                 475                 480
Phe

<210> SEQ ID NO 5
<211> LENGTH: 481
<212> TYPE: PRT
<213> ORGANISM: Haemophilus Influenzae

<400> SEQUENCE: 5

Met Lys Asn Gly Val Lys Gln Leu Ser Leu Leu Ser Leu Ile Gly Leu
1               5                   10                  15
Ser Leu Thr Asn Val Ala Trp Ala Glu Val Ala Arg Pro Lys Asn Asp
                20                  25                  30
Thr Leu Thr Asn Thr Ile Gln Ser Ala Glu Leu Lys Thr Ser Ser Phe
            35                  40                  45
Ser Ser Met Pro Lys Lys Glu Ile Pro Asn Arg His Ile Ile Ser Leu
        50                  55                  60
Ser Lys Ser Gln Leu Ala His His Pro Arg Leu Val Leu Arg Gly Leu
65                  70                  75                  80
Ile Pro Ala Leu Tyr Gln Asn Asn Thr Gln Ala Val Gln Leu Leu Leu
                85                  90                  95
Pro Leu Tyr Lys Gln Phe Pro Gln Gln Asp Asn Phe Leu Leu Thr Trp
                100                 105                 110
Ala Lys Ala Ile Glu Ala Arg Glu Gln Gly Asp Leu Thr Gln Ser Ile
```

```
                115                 120                 125
Ala Tyr Tyr Arg Glu Leu Phe Ala Arg Asn Ala Ser Leu Leu Pro Leu
130                 135                 140

Arg Tyr Gln Leu Ala Gln Ala Leu Phe Phe Asn Tyr Glu Asn Glu Ala
145                 150                 155                 160

Ala Lys Ile Gln Phe Glu Lys Leu Arg Thr Glu Val Asp Asp Glu Lys
                165                 170                 175

Phe Leu Gly Val Ile Asp Gln Tyr Leu Leu Thr Leu Asn Gln Arg Asn
            180                 185                 190

Gln Trp Ile Trp Gln Val Gly Leu Asn Phe Leu Asn Asp Asp Asn Leu
        195                 200                 205

Asn Asn Ala Pro Lys Ser Gly Thr Lys Ile Gly Ser Trp Thr Ala Trp
210                 215                 220

Glu Lys Glu Ser Gly Gln Gly Val Gly Tyr Ser Leu Ser Val Glu Lys
225                 230                 235                 240

Lys Trp Pro Trp Ala Asp His Phe Phe Ser Lys Thr Met Phe Asn Gly
                245                 250                 255

Asn Gly Lys Tyr Tyr Trp Asp Asn Lys Lys Tyr Asn Glu Ala Thr Val
            260                 265                 270

Arg Ile Gly Gly Gly Leu Gly Tyr Gln Thr Ala Ser Val Glu Val Ser
        275                 280                 285

Leu Phe Pro Phe Gln Glu Lys Arg Trp Tyr Ala Gly Gly Ser Ser Gly
290                 295                 300

Thr Asn Thr Met Lys Gln Tyr Ala Asp Lys Leu Gly Ile Arg Leu Glu
305                 310                 315                 320

Asn Val Asp Trp Leu Ser Lys Thr Trp Gln Ile Ser Thr Ala Leu Glu
                325                 330                 335

Tyr Gly Glu Ser Arg Tyr Lys Ile Arg Lys His Leu Asp Gly Asn Tyr
            340                 345                 350

Tyr Phe Ile Ser Ser Thr Leu Phe Tyr Leu Pro Lys Ser Thr Gln Phe
        355                 360                 365

Trp Phe Val Gly Met Asp Phe His Arg Glu Asn Thr Gln Ala Leu Asp
370                 375                 380

Asn Ala Tyr Gln Gln Lys Thr Leu Arg Leu Gly Trp Gly Gln Asp Trp
385                 390                 395                 400

Ser His Gly Ile Ser Ser Arg Leu Thr Phe Ser Tyr Ala Asn Arg Val
                405                 410                 415

Tyr Arg Glu Lys Asp Leu Ile Gly Ile Gln Gln Lys Asn Arg Glu Tyr
            420                 425                 430

Thr Thr Thr Ile Thr Leu Trp His Arg Asn Ile His Phe Met Gly Leu
        435                 440                 445

Thr Pro Lys Leu Ser Trp Asp Tyr Gln Lys Ser Thr Ser Asn His Ala
450                 455                 460

Phe Tyr Arg Tyr Asp Lys Asn Arg Ile Tyr Leu Glu Ile Gly Lys Ile
465                 470                 475                 480

Phe

<210> SEQ ID NO 6
<211> LENGTH: 654
<212> TYPE: PRT
<213> ORGANISM: N. meningitidis

<400> SEQUENCE: 6

Ala Thr Asn Asp Asp Asp Val Lys Lys Ala Ala Thr Val Ala Ile Ala
```

```
1               5                   10                  15
Ala Ala Tyr Asn Asn Gly Gln Glu Ile Asn Gly Phe Lys Ala Gly Glu
                20                  25                  30

Thr Ile Tyr Asp Ile Asp Glu Asp Gly Thr Ile Thr Lys Lys Asp Ala
                35                  40                  45

Thr Ala Ala Asp Val Glu Ala Asp Asp Phe Lys Gly Leu Gly Leu Lys
            50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
                100                 105                 110

Leu Asp Ala Thr Thr Asn Ala Leu Asn Lys Leu Gly Glu Asn Ile Thr
            115                 120                 125

Thr Phe Ala Glu Glu Thr Lys Thr Asn Ile Val Lys Ile Asp Glu Lys
            130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
            195                 200                 205

Glu Ala Ala Ala Gly Thr Ala Asn Thr Ala Ala Asp Lys Ala Glu Ala
    210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
                245                 250                 255

Glu Ser Asp Ser Lys Phe Val Arg Ile Asp Gly Leu Asn Ala Thr Thr
            260                 265                 270

Glu Lys Leu Asp Thr Arg Leu Ala Ser Ala Glu Lys Ser Ile Ala Asp
            275                 280                 285

His Asp Thr Arg Leu Asn Gly Leu Asp Lys Thr Val Ser Asp Leu Arg
    290                 295                 300

Lys Glu Thr Arg Gln Gly Leu Ala Glu Gln Ala Ala Leu Ser Gly Leu
305                 310                 315                 320

Phe Gln Pro Tyr Asn Val Gly Ala Thr Asn Asp Asp Val Lys Lys
            325                 330                 335

Ala Ala Thr Val Ala Ile Ala Ala Tyr Asn Asn Gly Gln Glu Ile
            340                 345                 350

Asn Gly Phe Lys Ala Gly Glu Thr Ile Tyr Asp Ile Asp Glu Asp Gly
            355                 360                 365

Thr Ile Thr Lys Lys Asp Ala Thr Ala Ala Asp Val Glu Ala Asp Asp
    370                 375                 380

Phe Lys Gly Leu Gly Leu Lys Lys Val Val Thr Asn Leu Thr Lys Thr
385                 390                 395                 400

Val Asn Glu Asn Lys Gln Asn Val Asp Ala Lys Val Lys Ala Ala Glu
                405                 410                 415

Ser Glu Ile Glu Lys Leu Thr Thr Lys Leu Ala Asp Thr Asp Ala Ala
            420                 425                 430
```

```
Leu Ala Asp Thr Asp Ala Ala Leu Asp Ala Thr Thr Asn Ala Leu Asn
            435                 440                 445

Lys Leu Gly Glu Asn Ile Thr Thr Phe Ala Glu Glu Thr Lys Thr Asn
        450                 455                 460

Ile Val Lys Ile Asp Glu Lys Leu Glu Ala Val Ala Asp Thr Val Asp
465                 470                 475                 480

Lys His Ala Glu Ala Phe Asn Asp Ile Ala Asp Ser Leu Asp Glu Thr
                485                 490                 495

Asn Thr Lys Ala Asp Glu Ala Val Lys Thr Ala Asn Glu Ala Lys Gln
            500                 505                 510

Thr Ala Glu Glu Thr Lys Gln Asn Val Asp Ala Lys Val Lys Ala Ala
        515                 520                 525

Glu Thr Ala Ala Gly Lys Ala Glu Ala Ala Gly Thr Ala Asn Thr
        530                 535                 540

Ala Ala Asp Lys Ala Glu Ala Val Ala Ala Lys Val Thr Asp Ile Lys
545                 550                 555                 560

Ala Asp Ile Ala Thr Asn Lys Asp Asn Ile Ala Lys Lys Ala Asn Ser
                565                 570                 575

Ala Asp Val Tyr Thr Arg Glu Glu Ser Asp Ser Lys Phe Val Arg Ile
            580                 585                 590

Asp Gly Leu Asn Ala Thr Thr Glu Lys Leu Asp Thr Arg Leu Ala Ser
        595                 600                 605

Ala Glu Lys Ser Ile Ala Asp His Asp Thr Arg Leu Asn Gly Leu Asp
610                 615                 620

Lys Thr Val Ser Asp Leu Arg Lys Glu Thr Arg Gln Gly Leu Ala Glu
625                 630                 635                 640

Gln Ala Ala Leu Ser Gly Leu Phe Gln Pro Tyr Asn Val Gly
                645                 650

<210> SEQ ID NO 7
<211> LENGTH: 488
<212> TYPE: PRT
<213> ORGANISM: Neisseria meningitidis

<400> SEQUENCE: 7

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
                20                  25                  30

Thr Leu Ser Lys Pro Ala Ala Pro Val Val Ser Glu Lys Glu Thr Glu
        35                  40                  45

Ala Lys Glu Asp Ala Pro Gln Ala Gly Ser Gln Gly Gln Gly Ala Pro
    50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
        115                 120                 125

Asn Gln Ala Thr Asp Ala Gly Glu Ser Ser Gln Pro Ala Asn Gln Pro
    130                 135                 140

Asp Met Ala Asn Ala Ala Asp Gly Met Gln Gly Asp Asp Pro Ser Ala
```

```
                145                 150                 155                 160
Gly Gly Gln Asn Ala Gly Asn Thr Ala Ala Gln Gly Ala Asn Gln Ala
            165                 170                 175
Gly Asn Asn Gln Ala Ala Gly Ser Ser Asp Pro Ile Pro Ala Ser Asn
        180                 185                 190
Pro Ala Pro Ala Asn Gly Gly Ser Asn Phe Gly Arg Val Asp Leu Ala
    195                 200                 205
Asn Gly Val Leu Ile Asp Gly Pro Ser Gln Asn Ile Thr Leu Thr His
210                 215                 220
Cys Lys Gly Asp Ser Cys Ser Gly Asn Asn Phe Leu Asp Glu Glu Val
225                 230                 235                 240
Gln Leu Lys Ser Glu Phe Glu Lys Leu Ser Asp Ala Asp Lys Ile Ser
            245                 250                 255
Asn Tyr Lys Lys Asp Gly Lys Asn Asp Lys Phe Val Gly Leu Val Ala
        260                 265                 270
Asp Ser Val Gln Met Lys Gly Ile Asn Gln Tyr Ile Ile Phe Tyr Lys
    275                 280                 285
Pro Lys Pro Thr Ser Phe Ala Arg Phe Arg Arg Ser Ala Arg Ser Arg
290                 295                 300
Arg Ser Leu Pro Ala Glu Met Pro Leu Ile Pro Val Asn Gln Ala Asp
305                 310                 315                 320
Thr Leu Ile Val Asp Gly Glu Ala Val Ser Leu Thr Gly His Ser Gly
            325                 330                 335
Asn Ile Phe Ala Pro Glu Gly Asn Tyr Arg Tyr Leu Thr Tyr Gly Ala
        340                 345                 350
Glu Lys Leu Pro Gly Gly Ser Tyr Ala Leu Arg Val Gln Gly Glu Pro
    355                 360                 365
Ala Lys Gly Glu Met Leu Ala Gly Ala Ala Val Tyr Asn Gly Glu Val
370                 375                 380
Leu His Phe His Thr Glu Asn Gly Arg Pro Tyr Pro Thr Arg Gly Arg
385                 390                 395                 400
Phe Ala Ala Lys Val Asp Phe Gly Ser Lys Ser Val Asp Gly Ile Ile
            405                 410                 415
Asp Ser Gly Asp Asp Leu His Met Gly Thr Gln Lys Phe Lys Ala Ala
        420                 425                 430
Ile Asp Gly Asn Gly Phe Lys Gly Thr Trp Thr Glu Asn Gly Ser Gly
    435                 440                 445
Asp Val Ser Gly Lys Phe Tyr Gly Pro Ala Gly Glu Glu Val Ala Gly
450                 455                 460
Lys Tyr Ser Tyr Arg Pro Thr Asp Ala Glu Lys Gly Gly Phe Gly Val
465                 470                 475                 480
Phe Ala Gly Lys Lys Glu Gln Asp
            485

<210> SEQ ID NO 8
<211> LENGTH: 320
<212> TYPE: PRT
<213> ORGANISM: Neisseria meningitidis

<400> SEQUENCE: 8

Met Pro Ser Glu Pro Pro Phe Gly Arg His Leu Ile Phe Ala Ser Leu
1               5                   10                  15

Thr Cys Leu Ile Asp Ala Val Cys Lys Lys Arg Tyr His Asn Gln Asn
            20                  25                  30
```

```
Val Tyr Ile Leu Ser Ile Leu Arg Met Thr Arg Ser Lys Pro Val Asn
             35                  40                  45

Arg Thr Ala Phe Cys Cys Leu Ser Leu Thr Thr Ala Leu Ile Leu Thr
 50                  55                  60

Ala Cys Ser Ser Gly Gly Gly Val Ala Ala Asp Ile Gly Ala Gly
 65                  70                  75                  80

Leu Ala Asp Ala Leu Thr Ala Pro Leu Asp His Lys Asp Lys Gly Leu
                 85                  90                  95

Gln Ser Leu Thr Leu Asp Gln Ser Val Arg Lys Asn Glu Lys Leu Lys
                100                 105                 110

Leu Ala Ala Gln Gly Ala Glu Lys Thr Tyr Gly Asn Gly Asp Ser Leu
            115                 120                 125

Asn Thr Gly Lys Leu Lys Asn Asp Lys Val Ser Arg Phe Asp Phe Ile
130                 135                 140

Arg Gln Ile Glu Val Asp Gly Gln Leu Ile Thr Leu Glu Ser Gly Glu
145                 150                 155                 160

Phe Gln Val Tyr Lys Gln Ser His Ser Ala Leu Thr Ala Phe Gln Thr
                165                 170                 175

Glu Gln Ile Gln Asp Ser Glu His Ser Gly Lys Met Val Ala Lys Arg
            180                 185                 190

Gln Phe Arg Ile Gly Asp Ile Ala Gly Glu His Thr Ser Phe Asp Lys
        195                 200                 205

Leu Pro Glu Gly Gly Arg Ala Thr Tyr Arg Gly Thr Ala Phe Gly Ser
    210                 215                 220

Asp Asp Ala Gly Gly Lys Leu Thr Tyr Thr Ile Asp Phe Ala Ala Lys
225                 230                 235                 240

Gln Gly Asn Gly Lys Ile Glu His Leu Lys Ser Pro Glu Leu Asn Val
                245                 250                 255

Asp Leu Ala Ala Ala Asp Ile Lys Pro Asp Gly Lys Arg His Ala Val
            260                 265                 270

Ile Ser Gly Ser Val Leu Tyr Asn Gln Ala Glu Lys Gly Ser Tyr Ser
        275                 280                 285

Leu Gly Ile Phe Gly Gly Lys Ala Gln Glu Val Ala Gly Ser Ala Glu
    290                 295                 300

Val Lys Thr Val Asn Gly Ile Arg His Ile Gly Leu Ala Ala Lys Gln
305                 310                 315                 320

<210> SEQ ID NO 9
<211> LENGTH: 262
<212> TYPE: PRT
<213> ORGANISM: Neisseria meningitidis

<400> SEQUENCE: 9

Cys Ser Ser Gly Gly Gly Ser Gly Gly Gly Val Ala Ala Asp
 1               5                  10                  15

Ile Gly Ala Gly Leu Ala Asp Ala Leu Thr Ala Pro Leu Asp His Lys
                 20                  25                  30

Asp Lys Gly Leu Lys Ser Leu Thr Leu Glu Asp Ser Ile Ser Gln Asn
             35                  40                  45

Gly Thr Leu Thr Leu Ser Ala Gln Gly Ala Glu Arg Thr Phe Lys Ala
         50                  55                  60

Gly Asp Lys Asp Asn Ser Leu Asn Thr Gly Lys Leu Lys Asn Asp Lys
 65                  70                  75                  80

Ile Ser Arg Phe Asp Phe Ile Arg Gln Ile Glu Val Asp Gly Gln Leu
                 85                  90                  95
```

-continued

```
Ile Thr Leu Glu Ser Gly Glu Phe Gln Ile Tyr Lys Gln Asp His Ser
                100                 105                 110

Ala Val Ala Leu Gln Ile Glu Lys Ile Asn Asn Pro Asp Lys Ile
            115                 120                 125

Asp Ser Leu Ile Asn Gln Arg Ser Phe Arg Val Ser Gly Leu Gly Gly
    130                 135                 140

Glu His Thr Ala Phe Asn Gln Leu Pro Asp Gly Lys Ala Glu Tyr His
145                 150                 155                 160

Gly Lys Ala Phe Ser Ser Asp Asp Ala Gly Gly Lys Leu Thr Tyr Thr
                165                 170                 175

Ile Asp Phe Ala Ala Lys Gln Gly His Gly Lys Ile Glu His Leu Lys
            180                 185                 190

Thr Pro Glu Gln Asn Val Glu Leu Ala Ala Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Lys Val His Glu Ile
                245                 250                 255

Gly Ile Ala Gly Lys Gln
            260
```

<210> SEQ ID NO 10
<211> LENGTH: 31
<212> TYPE: DNA
<213> ORGANISM: Artificial
<220> FEATURE:
<223> OTHER INFORMATION: Primer Sequence

<400> SEQUENCE: 10
gagatctaga gccggcattc gggcaaaaac c          31

<210> SEQ ID NO 11
<211> LENGTH: 29
<212> TYPE: DNA
<213> ORGANISM: Artificial
<220> FEATURE:
<223> OTHER INFORMATION: Primer Sequence

<400> SEQUENCE: 11
aacagcaacc cgggtatcaa tcggcggat          29

<210> SEQ ID NO 12
<211> LENGTH: 32
<212> TYPE: DNA
<213> ORGANISM: Artificial
<220> FEATURE:
<223> OTHER INFORMATION: Primer Sequence

<400> SEQUENCE: 12
ccgattgata cccgggttgc tgttcctttt cg          32

<210> SEQ ID NO 13
<211> LENGTH: 32
<212> TYPE: DNA
<213> ORGANISM: Artificial
<220> FEATURE:
<223> OTHER INFORMATION: Primer Sequence

<400> SEQUENCE: 13
gtgtattaat atggttattt tttatttttg tg                                              32

<210> SEQ ID NO 14
<211> LENGTH: 31
<212> TYPE: DNA
<213> ORGANISM: Artificial
<220> FEATURE:
<223> OTHER INFORMATION: Primer Sequence

<400> SEQUENCE: 14
gtgtatgcat tcagaacgtt ttattaaact c                                              31

<210> SEQ ID NO 15
<211> LENGTH: 32
<212> TYPE: DNA
<213> ORGANISM: Artificial
<220> FEATURE:
<223> OTHER INFORMATION: Primer Sequence

<400> SEQUENCE: 15
gtgtattaat atggttattt tttatttttg tg                                              32

<210> SEQ ID NO 16
<211> LENGTH: 31
<212> TYPE: DNA
<213> ORGANISM: Artificial
<220> FEATURE:
<223> OTHER INFORMATION: Primer Sequence

<400> SEQUENCE: 16
gtgtctcgag tcagaacgtt ttattaaact c                                              31

<210> SEQ ID NO 17
<211> LENGTH: 27
<212> TYPE: DNA
<213> ORGANISM: Artificial
<220> FEATURE:
<223> OTHER INFORMATION: Primer Sequence

<400> SEQUENCE: 17
ccccccgggc aggaaagcgc tgcatag                                                   27

<210> SEQ ID NO 18
<211> LENGTH: 27
<212> TYPE: DNA
<213> ORGANISM: Artificial
<220> FEATURE:
<223> OTHER INFORMATION: Primer Sequence

<400> SEQUENCE: 18
cgtctagagg ttcaacggca aatgtgc                                                   27

<210> SEQ ID NO 19
<211> LENGTH: 29
<212> TYPE: DNA
<213> ORGANISM: Artificial
<220> FEATURE:
<223> OTHER INFORMATION: Primer Sequence

<400> SEQUENCE: 19
cggggtaccc gtggaatgtt tctgctcaa                                                 29

<210> SEQ ID NO 20
<211> LENGTH: 28
<212> TYPE: DNA

```
<213> ORGANISM: Artificial
<220> FEATURE:
<223> OTHER INFORMATION: Primer Sequence

<400> SEQUENCE: 20
ggactagtcc attaggccta aatgcctg                                          28
```

IMMUNOGENIC COMPOSITIONS

TECHNICAL FIELD

The present invention relates to the field of native outer membrane vesicles (nOMVs), particularly nOMVs having increased levels of lipoproteins on their surface and use of the same in immunogenic compositions. The invention further relates to novel, genetically modified Gram-negative bacterial strains and their use in the preparation and manufacture of nOMVs.

REFERENCE TO SEQUENCE LISTING SUBMITTED ELECTRONICALLY VIA EFS-WEB

The content of the electronically submitted sequence listing (Name: VB66122_US_seq_1stg.txt; 36, 232 bytes; and Date of Creation: Jun. 29, 2016) was originally submitted in the International Application No. PCT/EP2017/066213 and is incorporated herein by reference in its entirety.

BACKGROUND TO THE INVENTION

Gram-negative bacteria spontaneously release bleb-like particles of outer cell wall membrane referred to as native outer membrane vesicles (nOMV) [1]. Outer membrane vesicles may also be produced artificially, for example, by detergent-extraction (referred to as dOMV). Outer membrane vesicles may also be produced from bacteria genetically engineered to exhibit a hyper-blebbing phenotype wherein, as a consequence of the genetic modification, large quantities of outer membrane bud off thereby providing a practical source of membrane material. Detergent extracted OMVs differ from nOMVs because the detergent required removes components of the membrane such as lipoproteins and increases the cost of production of dOMV relative to nOMV. Whilst nOMV can be isolated from culture medium, generally the amounts produced are too low to be practical for commercial vaccine production.

The expression of complex outer membrane proteins in their native confirmation and correct orientation in nOMVs provides significant potential advantages over recombinant proteins. To induce nOMV formation to provide greater amounts sufficient for commercial vaccine production, the membrane structure is modified by the deletion of genes encoding key structural components, for example, gna33 (*Meningococcus*) or tolR (*Shigella* and *Salmonella*) [2]. Unlike whole bacterial vaccines, nOMVs lack inner membrane and cytoplasmic components which are rarely the targets of protective immunity. Since nOMVs, particularly nOMVs isolated from hyper-blebbing bacteria, are particularly suited for development of vaccines it is an object of the invention to provide methods for producing nOMVs with improved characteristics and qualities.

BRIEF DESCRIPTION OF THE INVENTION

In a First Aspect the invention provides a Gram-negative bacterium which over-expresses, constitutively expresses or inducibly expresses a flippase. The bacterium may be hyper-blebbing. Particularly the Gram-negative bacterium is selected from the group consisting of *Neisseria, Salmonella, Shigella, Haemophilus, Bordetella, Moraxella, Chlamydia* and *Escherichia*. Yet more particularly the Gram-negative bacterium is selected from the group consisting of *Neisseria meningitidis, Neisseria gonorrhoeae, Salmonella typhi, Salmonella typhimurium, Shigella flexneri, Shigella dysenteriae, Shigella boydii, Shigella sonnei, Haemophilus influenzae, Bordetella pertussis, Chlamydia trachomatis* and *Escherichia coli*.

The term "Hyper-blebbing", as used herein, refers to a mutant strain of bacteria that spontaneously releases outer membrane vesicles in greater quantities than a wild-type or parent strain from which it was derived (e.g., per unit of time). In general, hyperblebbing mutants release greater quantities of outer membrane vesicles than the wild-type or parent strain from which it was derived, for example, greater than 10%, greater than 20%, greater than 30% or greater than 40%. The hyper-blebbing Gram-negative bacterium may be a naturally occurring mutant strain or may be genetically modified to exhibit a hyper-blebbing phenotype. The term "wild-type" with reference to bacteria refers to a bacterium that has not been modified either chemically or genetically in any way whatsoever (other than growth in culture medium). Particularly, a "wild-type" bacterium is one that has not been genetically modified to increase release of outer membrane vesicles. In contrast, the term "modified" or "mutant" refers to a bacterium, gene or gene product that displays modifications in sequence and/or properties (i.e., altered characteristics) when compared to the wild-type bacterium, gene or gene product. It is noted that naturally occurring mutants can be isolated; these are identified by the fact that they have altered characteristics (including altered nucleic acid sequences) when compared to the wild-type bacteria, gene or gene product.

The term "constitutively expresses" refers to the continuous expression of a gene of interest without any regulation (transcription is neither suppressed nor induced). In contrast, the term "inducibly expresses" refers to the regulated expression of a gene of interest wherein transcription occurs in response to an inducer. The term "over-expresses" is used to indicate a level of expression that is higher than that typically observed in a control, wild-type and/or non-transgenic bacterium. Particularly, by reference to levels of mRNA that may be measured using any of a number of techniques known to those skilled in the art including, but not limited to Northern blot analysis and/or quantitative real time polymerase chain reaction (qRT-PCR).

Neisserial strains, such as *Neisseria meningitidis* or *Neisseria gonorrhoeae*, may be genetically modified to exhibit a hyper-blebbing phenotype by down-regulating or abolishing expression of, by way of non-limiting example, GNA33. Similar mutations are known in other bacteria, for example, *Haemophilus influenza, Moraxella catarrhalis* and *Escherichia coli* strains may be genetically modified to exhibit a hyper-blebbing phenotype by down-regulating or abolishing expression of one or more genes selected from the group consisting of tolQ, tolR, tolX, tolA and tolB. Strains of *Shigella flexneri, Shigella dysenteriae, Shigella boydii* and *Shigella sonnei* can be genetically modified to exhibit a hyper-blebbing phenotype by down-regulating or abolishing expression of one or more tolR or OmpA. Suitable mutations for down-regulating or abolishing expression include point mutations, gene deletions, gene insertions, and any modification of genomic sequences that results in a change in gene expression, particularly a reduction and more particularly inactivation or silencing. Further suitable mutations are known in the art.

In some embodiments, the hyper-blebbing Gram-negative bacterium is genetically modified by mutation to reduce the pyrogenic potential of the lipopolysaccharide (LPS) of the bacteria. Particular mutations include, by way of non-limiting example, mutations in lpxL1, synX, lgtA, htrA, msbB1, msbB2, virG and homologues thereof. Suitable mutations for down-regulating or abolishing expression include point mutations, gene deletions, gene insertions, and any modification of genomic sequences that results in a change in gene expression, particularly a reduction and yet more particularly inactivation or silencing. Preferably the mutation is a deletion. Further suitable mutations are known in the art.

The hyper-blebbing Gram-negative bacterium may be further genetically engineered by one or more processes selected from the following group: (a) a process of down-regulating expression of immunodominant variable or non-protective antigens, (b) a process of up-regulating expression of protective OMP antigens, (c) a process of down-regulating a gene involved in rendering the lipid A portion of LPS toxic, (d) a process of up-regulating a gene involved in rendering the lipid A portion of LPS less toxic, and (e) a process of genetically modifying the bacterium to express a heterologous antigen.

Particularly the flippase comprises a sequence having 80% sequence identity with, or that is a homologue of, a sequence selected from the group consisting of SEQ ID NO: 1, SEQ ID NO: 2, SEQ ID NO: 3 and SEQ ID NO: 4. Yet more particularly the flippase comprises a sequence having greater than 85%, greater than 90%, greater than 95%, greater than 96%, greater than 97%, greater than 98% or greater than 99% sequence identity with a sequence selected from the group consisting of SEQ ID NO: 1, SEQ ID NO: 2, SEQ ID NO:3 and SEQ ID NO:4. In some embodiments, the flippase comprises a sequence selected from the group consisting of SEQ ID NO: 1, SEQ ID NO: 2, SEQ ID NO: 3 and SEQ ID NO:4.

In a Second Aspect of the invention, there is provided a preparation of outer membrane vesicles obtained from the bacterium of the first aspect. The outer membrane vesicles obtained from such bacteria have a higher level or amount of at least one lipoprotein exposed on the surface, for example, as measured by FACS analysis and when compared to outer membrane vesicles obtained from a wild-type or parent strain. Particularly the outer membrane vesicles are capable of being filtered through a 0.22 μm membrane.

In a Third Aspect of the invention, pharmaceutical compositions comprising the preparation of outer membrane vesicles of the Second Aspect of the invention are provided. Particularly, the pharmaceutical composition comprises a pharmaceutically acceptable diluent or carrier. More particularly the pharmaceutical composition is for use in a method of treatment of the human or animal body. Preferably the pharmaceutical composition is a vaccine composition.

A Fourth Aspect of the invention provides a method of protecting, preventing or treating an individual against a bacterial infection which comprises administering to the individual an effective amount of outer membrane vesicles of the Second Aspect or pharmaceutical composition of the third aspect. Particularly the individual is a mammal, preferably a human. The bacterial infection may correspond to the genus and/or species from which the OMV was obtained (e.g., *Neisseria meningitides*-derived OMV used to protect, prevent or treat infection by *Neisseria meningitidis*). Where present, the one or more heterologous outer membrane protein may or may not correspond to the genus and/or species from which the OMV was obtained. The bacterial infection may correspond to the genus and/or species from which one or more heterologous outer membrane protein was obtained or derived (e.g., *Neisseria meningitides*-derived outer membrane protein used to protect, prevent or treat infection by *Neisseria meningitidis*). The species from which the OMV was obtained may or may not correspond to the bacterial infection. In one embodiment, the species from which the OMV was obtained and the one or more heterologous protein correspond to the bacterial infection.

According to a Fifth Aspect there is provided a process for preparing a pharmaceutical composition comprising a preparation of outer membrane vesicles of the Second Aspect, the process comprising: (a) inoculating a culture vessel containing a nutrient medium suitable for growth of the bacterium of the First Aspect; (b) culturing said bacterium; (c) recovering outer membrane vesicles from the medium; and (d) mixing the outer membrane vesicles with a pharmaceutically acceptable diluent or carrier. In some embodiments the process may further comprise a step, after either step (c) or step (d), comprising sterile-filtering the preparation of outer membrane vesicles. Particularly the filtration step comprises at least one step of tangential flow filtration (TFF). Yet more particularly the process does not utilise centrifugation.

In a Sixth Aspect, there is provided a method for producing a hyper-blebbing bacterium according to the First Aspect which method comprises genetically modifying a Gram-negative bacterial strain by: (a) engineering the strain to down-regulate expression of one or more Tol genes; and (b) engineering the strain to over-express, consitutively express or inducibly express a flippase. Steps (a) and (b) of the method may be performed in any order or may be carried out at substantially the same time.

BRIEF DESCRIPTION OF FIGURES

The patent or application file contains at least one drawing executed in color. Copies of this patent or patent application publication with color drawing(s) will be provided by the Office upon request and payment of the necessary fee.

FIG. 4A-4B: (A) Schematic representation of nmb0313 genomic complementation strategy; (B) Western blot analysis of NMB0313 expression in increasing IPTG concentrations.

FIGS. 6A-6D: A) Schematic representation of plasmids used for *E. coli* transformation; B) Western blot analysis of NMB0313 and fHbp recombinant expression in the presence of increasing IPTG concentrations and FACS analysis of fHbp; C) In the charts are reported the MFI extrapolate from FACS analysis of fHbp at the different IPTG concentrations; D) western blot analysis of NHBA recombinant expression and FACS analysis of NHBA (preliminary results).

FIG. 11: Immunization scheme outline.

FIGS. 12A-12B: Elisa titers using recombinant fHbp as a coating antigen. Statistical analysis was performed using Kruskal-Wallis multiple comparisons test (ns: not significant; p<0.0065; *p<0.0009, ****p<0.0001).

FIGS. 13A-13B: rSBA titers with pooled mice sera.

FIGS. 14A-14B: rSBA with single mice. Statistical analysis was performed using Kruskal-Wallis multiple comparisons test (p<0.0024, **p<0.0001).

FIGS. 15A-15B: Elisa titers using α-NHBA as a coating antigen. Statistical analysis was performed using Kruskal-Wallis multiple comparisons test (ns: not significant; p<0.0060; *p<0.0002,).

FIG. 17A-17B: rSBA with single mice. Statistical analysis was performed using Kruskal-Wallis multiple comparisons test **p<0.0051).

FIG. 19: A) 4 ug of OMVs were loaded on a SDS gel page. B) WB analysis of 1 ug of OMVs stained with α-fHbp policlonal serum and α-NHBA policlonal serum.

FIG. 20: rSBA with pooled mice sera.

FIGS. 21A-21L: Example B raw data.

DETAILED DESCRIPTION OF THE INVENTION

Figure 1A:
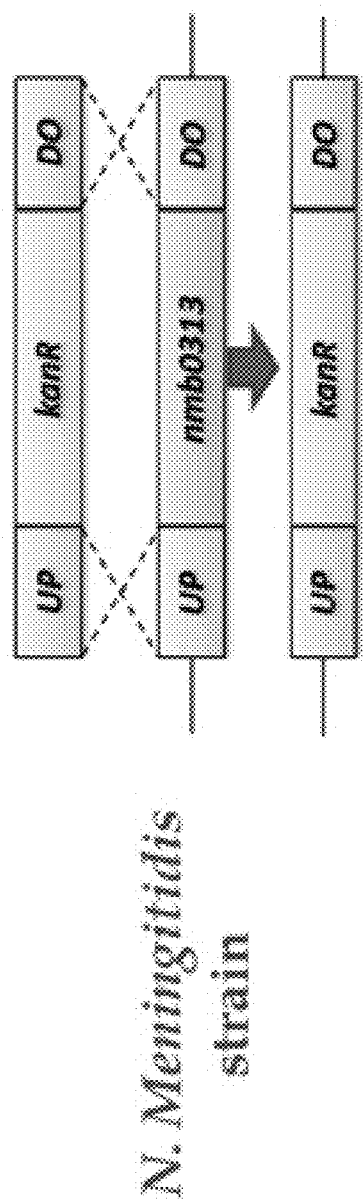
FIGS. 1A-1B: (A) Schematic representation of NMB0313 predicted structural domains (BLASTP 2.3.1): (B) Schematic representation of nmb0313 knock out strategy.

The inventors have discovered that co-expression of a flippase in a bacterial cell with at least one lipoprotein of interest (such as factor H binding protein (fHbp)) strongly influences the total amount of lipoprotein of interest and/or proportion of lipoprotein of interest that is surface exposed. The Inventors have further discovered that Gram-negative bacterial cells co-expressing a flippase and at least one lipoprotein of interest can be used to generate outer membrane vesicles that are enriched in said at least one lipoprotein of interest. Such OMVs (sometimes referred to as Generalised Modules for Membrane Antigens) isolated from such gram-negative bacterial cells are particularly suited to use in immunogenic compositions such as vaccines. For the avoidance of doubt, reference to OMVs or GMMA is intended to refer to native outer membrane vesicles particularly native outer membrane vesicles derived from bacteria that have or display a hyper-blebbing phenotype and does not include detergent extracted outer membrane vesicles.

The outer membranes of gram-negative bacteria are immunologically important structures because of their accessibility to host defense mechanisms. Lipoproteins are proteins characterized by the presence of a lipidated cysteine which allow the anchoring of the molecule to the membrane. Preferably, the at least one lipoprotein of interest is attached to the the extracellular side of the outer membrane. Yet more particularly, the at least one lipoprotein of interest is an immunogenic lipoprotein. Thus the term "surface exposed" is used to mean that the lipoproteins are available for antibody binding (e.g., on the outer membrane outer leaflet of bacterial cells and/or OMVs). Thus, OMVs of the invention comprise more of the at least one lipoprotein of interest and/or an increased proportion and/or amount of the at least one lipoprotein of interest which is surface-exposed.

The term "enriched", refers to a compound or composition that has an increased proportion of a desired property or element. For example, an OMV or GMMA that is "enriched" for lipoprotein means that the OMV or GMMA comprises a higher proportion of lipoprotein (e.g., more than 50%, 55%, 60%, 65%, 70%, 75%, 80%, 85%, 90%, 95% or more up to 100%) and/or a higher fraction (greater than 1.25, 1.5, 2, 2.5, 3, 3.5, 4, 5.5, 5 fold or greater) of total lipoprotein and/or a higher fraction (greater than 1.25, 1.5, 2, 2.5, 3, 3.5, 4, 5.5, 5 fold or greater) of surface exposed lipoprotein than an OMV or GMMA derived from a cell that does not overexpress, constitutively express or been induced to express a flippase.

This is advantageous because lipoproteins are able to activate an immune response in the host ranging from generation of bactericidal antibody to generation of cytotoxic T-cell response. For example, Factor H binding protein (fHbp) is a 28 kD lipoprotein identified as a protective antigen from *Neisseria meningitidis* that is capable of eliciting a broadly cross-reactive PorA-independent bactericidal response. Improving exposure or amount of lipoproteins on the surface of outer membrane vesicles, particularly GMMA, may lead to improvements in the immune response obtained following vaccination. In addition, co-expression of a flippase may also facilitate surface exposure of heterologously expressed lipoproteins. Thus, the invention also has the potential to aid dose sparing, reducing the amount of outer membrane vesicle component needed in a pharmaceutical or vaccine composition to induce a desired immune response thereby reducing the risk of, for example, pyrogenicity.

The Bacterium

The invention can be applied to various Gram negative bacteria, such as species in any of genera *Escherichia, Shigella, Neisseria, Moraxella, Bordetella, Borrelia, Brucella, Chlamydia, Haemophilus, Legionella, Pseudomonas, Yersinia, Helicobacter, Salmonella, Vibrio*, and the like. For example, the bacterium may be *Bordetella pertussis, Borrelia burgdorferi, Brucella melitensis, Brucella ovis, Chlamydia psittaci, Chlamydia trachomatis, Moraxella catarrhalis, Escherichia coli, Haemophilus influenzae* (including non-typeable stains), *Legionella pneumophila, Neisseria gonorrhoeae, Neisseria meningitidis, Neisseria lactamica, Pseudomonas aeruginosa, Yersinia enterocolitica, Helicobacter pylori, Salmonella enterica* (including serovars *typhi* and *typhimurium*, as well as serovars *paratyphi* and *enteritidis*), *Vibrio cholerae*, etc.

The invention is particularly suitable for use with *Neisseria* (such as *Neisseria meningitidis* or *Neisseria gonorrhoeae*), *Salmonella* (such as *Salmonella typhi* or *Salmo-* nella typhimurium), Shigella (such as S. dysenteriae, S. flexneri, S. boydii or S. sonnei) Escherichia coli (including extraintestinal pathogenic strains), Haemophilus influenzae (for example non-typeable Heamophilus influenzae or NtHI) and Bordatella pertussis.

Gram-negative bacteria spontaneously release outer membrane vesicles during bacterial growth and these can be purified from the culture medium. In preferred embodiments, bacteria for use in the invention are, relative to their corresponding wild-type strains, hyperblebbing i.e. they release into their culture medium larger quantities of outer membrane vesicles than the wild-type strain. Naturally occurring hyperblebbing strains for use in the invention are known in the art, for example, N. gonorrhoeae strain WR302. In some embodiments, the bacteria are genetically modified to release greater quantities of outer membrane vesicles or GMMA into the culture medium during bacterial cell growth and replication. Particular genes or proteins known to alter vesiculation include, by way of non-limiting example, GNA33, ompA, degP, degS, nlpl, ompC, ompR, pnp, ponB, rmpM, rseA, tatC, tolA, tolQ, tolR, tolB, pal, wag/rfaG, wzxE, yieM and homologues thereof.

In some embodiments, at least one of the proteins known to alter vesiculation is removed, for example, by deletion or inactivation of the gene. Suitable methods for deleting or inactivating genes are known in the art. In other embodiments, overexpression of particular genes/proteins such as the N-terminal domain of g3p phage protein or Translocation domains of colicins A and E3 may lead to increased vesiculation. Suitable methods for expressing, particularly over-expressing, genes/proteins are known in the art.

Flippases

Flippases are transmembrane lipid transporter proteins located in the cell membrane that are responsible for aiding the movement of phospholipid molecules between or across the cell membrane. Thus, flippases of the present invention are lipid (lipoprotein) transporters with the ability to move or facilitate movement (for example as part of a multifactorial process) of one or more lipoproteins to the extracellular side of the outer membrane.

An exemplary flippase involved in surface exposure of N. meningitidis lipoproteins, has been identified and is encoded by the nmb0313 gene. It is an outer membrane protein characterized by the presence of an N-terminal domain with a Tetratricopepdide Repeat domain (TPR) and a C-terminal transmembrane domain structured as a porin-like domain. The nucleic and amino acid sequences of nbm0313 are provided as SEQ ID NO: 1 and SEQ ID NO: 2 respectively. The amino acid sequence of a further flippase from N. meningitidis, nmb1971, is provided as SEQ ID NO: 3. Flippase homologues from Streptococcus pneumonia and Haemophilus influenzae have also been identified and are provided as SEQ ID NO: 4 and SEQ ID NO: 5, respectively.

In certain embodiments of the invention, the gram negative bacterium is genetically engineered to inducibly express at least one flippase (derived from a strain that does not naturally express a flippase or, alternatively, derived from a strain that does naturally express a flippase [e.g., in replacement of or in addition to the naturally expressed flippase]). In an inducible expression system, expression of the flippase coding sequence occurs in the bacterial cell in response to an applied stimulus, for example, in response to contact with an expression mediator compound such as, by way of non-limiting example, IPTG. Thus, in certain embodiments the gram-negative bacterium is genetically engineered to comprise an inducible expression cassette which is responsive to a transcription modulator configured such that inducible expression of a flippase coding sequence is obtained. In other embodiments of the invention, the gram negative bacterium is genetically engineered to constitutively express at least one flippase such that expression of a flippase coding sequence in a gram-negative bacterial cell is continuous irrespective of the presence or absence of a particular expression mediator component. The term "over-expresses" or "overexpression" refers to expression of a gene product at a level greater than that expressed prior to manipulation of the microorganism or in a comparable microorganism which has not been manipulated. Thus, the microorganism can be genetically designed or engineered to overexpress a level of flippase greater than that expressed in a comparable microorganism which has not been engineered. Genetic engineering can include, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules, for example, to block expression of repressor proteins). Genetic engineering can also include deletion of a gene, for example, to block a pathway or to remove a repressor. The flippase may be a heterologous flippase. The term "heterologous flippase" refers to a flippase gene that is either foreign to a selected host cell, or is otherwise altered (for example, a native gene placed under control of a different promoter). For example, a heterologous nucleic acid may be a nucleic acid that is normally found in the reference organism at a different genomic location or may be a nucleic acid that is not normally found in the reference organism. A gram-negative bacterium comprising a hetereologous flippase may be produced by introducing the flippase polynucleotide or gene sequence into the gram-negative bacterium. In particular examples, the polynucleotide sequence of a heterologous flippase comprises a native coding sequence, or portion thereof, that is reintroduced into a gram-negative bacterium in a form that is different from the corresponding native polynucleotide. For example, a polynucleotide sequence of a heterologous flippase may include a native coding sequence that is a portion of a chimeric gene including non-native regulatory regions that is reintroduced into the native gram-negative bacterium.

Outer Membrane Vesicles or GMMA

The OMVs or GMMA typically have a diameter of 35-120 nm by electron microscopy e.g. 50 nm diameter. OMVs or GMMA released during bacterial growth can be purified from the culture medium. Purification ideally involves separating the GMMA from living and/or intact bacteria, for example, by size-based filtration using a filter, such as a 0.22 µm filter, which allows the GMMA to pass through but which does not allow intact bacteria to pass through, or by using low speed centrifugation to pellet cells while leaving GMMA in suspension. Suitable purification methods are known in the art. A preferred two-step filtration purification process is described in WO2011/036562 herein incorporated by reference. Particularly the two-step filtration process is used to seperate GMMA from cell culture biomass without using centrifugation.

OMV or GMMA containing compositions of the invention will generally be substantially free from whole bacteria, whether living or dead. The size of the GMMA means that they can readily be separated from whole bacteria by filtration e.g. as typically used for filter sterilisation. Although GMMA will pass through a standard 0.22 µm filters, these can rapidly become clogged by other material, and so it may be useful to perform sequential steps of filter sterilisation through a series of filters of decreasing pore size before using a 0.22 µm filter. Examples of preceding filters would be those with pore size of 0.8 µm, 0.45 µm, etc. GMMA are spontaneously-released from bacteria and separation from the culture medium, for example, using filtration, is convenient. Outer membrane vesicles formed by methods which involve deliberate disruption of the outer membrane (e.g. by detergent treatment, such as deoxycholate-extraction, or sonication) to cause outer membrane vesicles to form are excluded from the scope of the invention. Preferably, OMVs or GMMA used in the invention are substantially free from inner membrane and cytoplasmic contamination and contain lipids and proteins.

Alteration of Lipid A Structure

Preferably, the OMV or GMMA are prepared from a Gram negative bacterium having a genetic modification which causes the bacterium to produce a lipopolysaccharide (LPS) that is modified to have reduced toxicity. Preferably, the Gram negative bacterium produces LPS with reduced toxicity wherein the LPS (or its Lipid A moiety (LA)) is modified to have reduced toxicity. An LPS that is modified to have reduced toxicity is herein understood as an LPS that is modified to have less toxicity than the toxicity of a corresponding wild-type LPS. Preferably, the modified LPS has less than about 90, 80, 60, 40, 20, 10, 5, 2, 1, 0.5, or 0.2% of the toxicity of the corresponding wild-type LPS. The toxicities of wild-type and various modified LPS's with reduced toxicity may be determined in any suitable assay known in the art. A preferred assay for determining the toxicity, i.e. the biological activity of the LPS is the WEHI test for TNF-alpha induction in the MM6 macrophage cell line [43, 44].

However, while it is preferred that the LPS of the Gram negative bacterium (or its LA moiety) has reduced toxicity, it is further preferred that the LPS retains at least part of immunostimulatory activity, i.e., adjuvant activity. Thus, the LPS with reduced toxicity of the Gram negative bacterium to be used in the invention preferably has at least about 10, 20, 40, 80, 90 or 100% of the immunostimulatory activity of the corresponding wild-type LPS, whereby the immunostimulatory activity is determined by measuring the production of at least one cytokine or the expression of at least one costimulatory molecule upon co-cultivation of dendritic cells (DC) with the Gram negative bacterium producing the LPS with reduced toxicity as described in Example 3 in WO 2005/107798.

Gram negative LPS's having reduced toxicity of the Lipid A moiety but retaining (part of) the adjuvant activity, may e.g. be obtained from genetically modified Gram negative pathogens and as reviewed in WO02/09746. Genetically modified Gram negative pathogens producing LPS with reduced toxicity of the Lipid A moiety but retaining (part of) their adjuvant activity include e.g. Gram negative bacteria having one or more genetic modifications that decrease or knock-out expression of one or more genes selected from the lpxL1 and lpxL2 genes or homologues thereof (formerly known as htrB and msbB; see e.g. WO00/26384; U.S. Pat. No. 5,997,881) and the lipid A 4'-kinase encoding lpxK gene or a homologues thereof (see also below); and genetic modifications that effect the expression of one or more a heterologous lpxE and pagL genes. Particular genetic modifications are modifications that decrease or knock-out expression of one or more genes selected from the lpxL1 and lpxL2 genes or homologues thereof. A preferred LPS with reduced toxicity of the Lipid A moiety but retaining (part of) its adjuvant activity is an LPS described in WO00/26384.

For example, it is known to modify bacteria so that they do not express a native lipopolysaccharide (LPS), particularly for *E. coli, meningococcus, Shigella*, and the like. Various modifications of native LPS can be made e.g. these may disrupt the native lipid A structure, the oligosaccharide core, or the outer O antigen. Suitable modifications include deletion or inactivation of, by way of non-limiting example, lpxL, lpxL1, lpxL2, lpxM, htr, msbB1, msbB2, pagP, lgtA, synX and the like.

Suitable *Shigella* strains for use in the invention may include one or more further changes relative to a wild-type strain. Particularly, strains for use with the invention include one or more mutations resulting in inactivation of htrB, msbB1 and/or msbB2. By way of non-limiting example, suitable mutations may be selected from the group consisting of ΔhtrB, ΔmsbB1 and ΔmsbB2. For simplicity, double deletions of both msbB1 and msbB2 may also be referred to as ΔDmsbB, Inactivation of htrB or msbB1 and msbB2 reduce acylation in lipid A. In some embodiments, strains for use with the invention lack the O antigen in the LPS, thereby avoiding serotype-specific responses. In *S. sonnei* the O antigen is absent when the virulence plasmid is removed. In other embodiments, strains for use with the invention produce LPS comprising the O antigen. The presence of the O antigen may be beneficial since immunogenic compositions will elicit both serotype specific and additional cross-reactive immune responses. Loss of the virulence plasmid leads to loss of the msbB2 gene, and the chromosomal msbB1 gene can be inactivated, thereby removing myristoyl transferase activity and providing a penta-acylated lipid A in the LPS. Particular *Shigella* strains for use in the invention have penta-acylated LPS. Alternatively, inactivation of htrB results in loss of the lauroyl chain and thus can yield penta-acylated LPS in some strains and/or forms of lipid A that are less toxic than wild type lipid A. For example, in *S. flexneri*, inactivation of htrB may be compensated for by the activity of another enzyme, LpxP that results in hexa-acylated lipid A wherein the lauroyl-chain is replaced by a palmitoleoyl chain Hexy-acylated lipid A comprising palmitoleoyl chains are less toxic than wild type lipid A.

Suitable strains are disclosed in the examples. Other suitable strains are known in the art, by way of non-limiting example in WO2006/046143, EP2279747, WO2011/036564 and WO2014/174043.

Lipoproteins of Particular Interest

Particularly, the Gram-negative bacterial cells will co-express at least one flippase and at least one lipoprotein of interest such that the bacterial cells can be used to generate outer membrane vesicles that are enriched in said at least one lipoprotein of interest.

The at least one lipoprotein of interest may be a heterologous lipoprotein or a native lipoprotein. The term "heterologous lipoprotein" refers to a lipoprotein that is either foreign to a selected host cell, and/or is otherwise altered (for example, a native gene placed under control of a different promoter). For example, the nucleotide sequence of a heterologous lipoprotein may be a nucleotide sequence that is normally found in the reference organism at a different genomic location or may be a nucleic acid that is not normally found in the reference organism. A gram-negative bacterium comprising a heterologous lipoprotein may be produced by introducing the polynucleotide or gene sequence of the heterologous lipoprotein into the gram-negative bacterium. In particular examples, the polynucleotide or gene sequence of the heterologous lipoprotein comprises a native coding sequence, or portion thereof, that is reintroduced into a gram-negative bacterium in a form that is different from the corresponding native polynucleotide. For example, the polynucleotide or gene sequence of the heterologous lipoprotein may include a native coding sequence that is a portion of a chimeric gene including non-native regulatory regions that is reintroduced into the native gram-negative bacterium.

However, the at least one lipoprotein of interest may also be a native lipoprotein which is a lipoprotein endogenously expressed and normally present in the cell. By way of non-limiting example, the following are lipoproteins of particular interest:

fHbp (Factor H Binding Protein)

The fHbp antigen has been characterised in detail. It has also been known as protein '741' (SEQ IDs 2535 & 2536 in ref 29), 'NMB 1870', 'GNA1870' [34-36], 'P2086', 'LP2086' or 'ORF2086' [37-39]. It is naturally a lipoprotein and is expressed across many meningococcal serogroups. The structure of fHbp's C-terminal immunodominant domain ('fHbpC') has been determined by NMR [40]. This part of the protein forms an eight-stranded β-barrel, whose strands are connected by loops of variable lengths. The barrel is preceded by a short a-helix and by a flexible N-terminal tail. The protein was confirmed as a factor H binding protein, and named fHbp, in reference 41.

The fHbp antigen falls into three distinct variants [42] and it has been found that serum raised against a given family is bactericidal within the same family, but is not active against strains which express one of the other two families i.e. there is intra-family cross-protection, but not inter-family cross-protection. The invention can use a single fHbp variant, but to provide broader coverage a composition can usefully include at least two fHbp variants or at least three fHbp variants. The fHbp gene expresses a protein precursor which contains a lipoprotein signal motif, LXXC. The signal sequence is cleaved such that the cysteine (C) becomes the N terminus of the mature fHbp and is cotranslationally modified to a tri-Pam-Cys residue which serves to anchor the protein to the neisserial outer membrane. Mature fHBP is 253 to 266 amino acids in length; most of the variation in size is a result of the variable length of a flexible segment or spacer, composed of 2 to 15 μlycine and serine residues immediately following the N-terminal cysteine. Exemplary sequences of the protein precursor and mature fHbp are provided in SEQ ID NOs: 8 and 9 respectively, other suitable sequences are known in the art.

NHBA (Neisserial Heparin Binding Antigen)

Figure 15A:
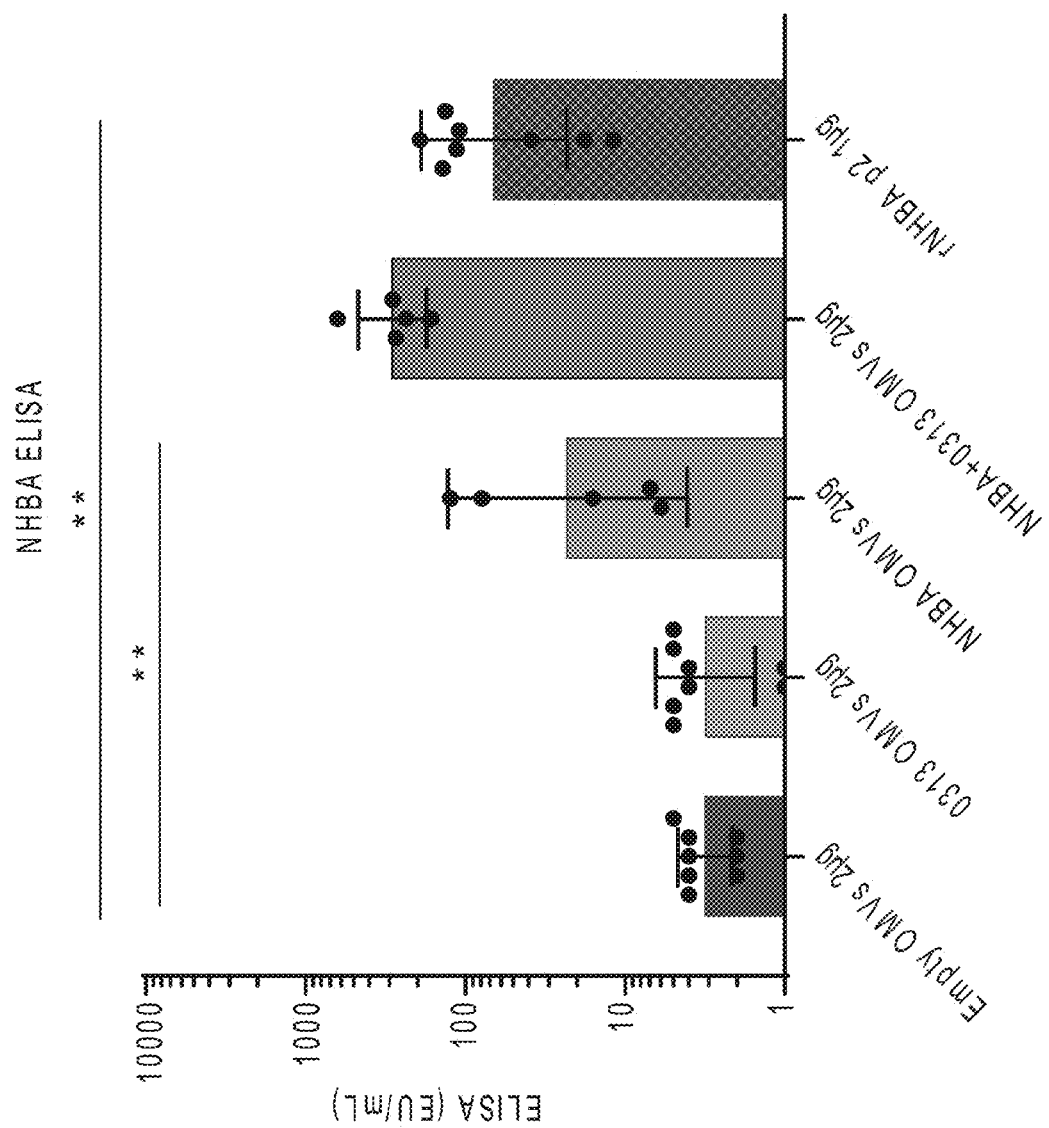
Figure 21J:
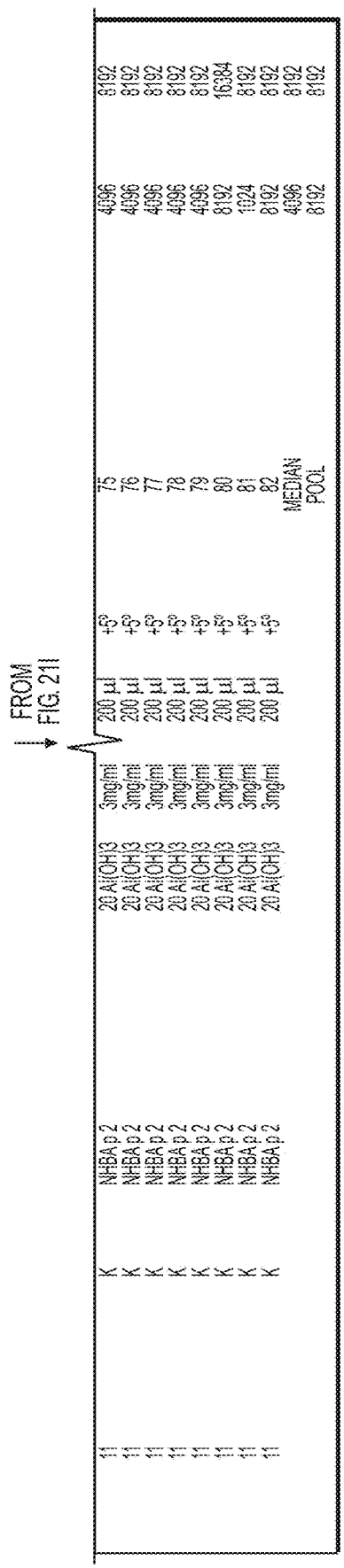

NHBA was included in the published genome sequence for meningococcal serogroup B strain MC58 [30] as gene NMB2132 (GenBank accession number GL7227388; SEQ ID NO: 7 herein). Sequences of NHBA from many strains have been published since then. For example, allelic forms of NHBA (referred to as protein '287') can be seen in FIGS. 5 and 15 of reference 33, and in example 13 and FIG. 21 of reference 29 (SEQ IDs 3179 to 3184 therein). Various immunogenic fragments of NHBA have also been reported.

NadA (Neisserial Adhesin A)

Figure 9:
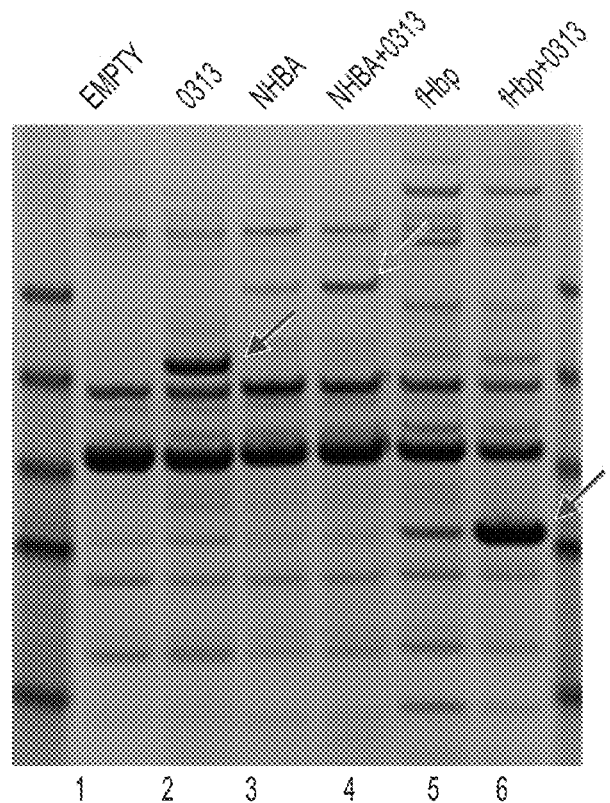
FIG. 9: 4 ug of OMVs were loaded on an SDS gel page and the bands relative to NMB0313 (pink), NHBA (green) and fHBP (red) are highlighted.

'NadA' (Neisserial adhesin A) from serogroup B of *N. meningitidis* is disclosed as protein '961' in reference 29 (SEQ IDs 2943 & 2944) and as 'NMB1994' in reference 30 (see also GenBank accession numbers: 11352904 & 7227256). A detailed description of the protein can be found in reference 31. When used according to the present invention, NadA may take various forms. Preferred forms of NadA comprise a C-terminal membrane anchor (e.g. residues 351-405 for strain 2996), since expression of NadA without its membrane anchor domain results in secretion of the protein into the culture supernatant. Particular NadA sequences have 50% or more identity (e.g. 60%, 70%, 80%, 90%, 95%, 99% or more) to SEQ ID 6. This includes NadA variants (e.g. allelic variants, homologs, orthologs, paralogs, mutants, etc.). Allelic forms of NadA are shown in FIG. 9 of reference 32.

Immunogenic Compositions

The immunogenic compositions may comprise any suitable amount of outer membrane vesicles or GMMA per unit dose. Suitable amounts of the GMMA protein may be from 0.1 to 200 μg per unit dose. Per unit dose, immunogenic compositions of the invention may comprise a total concentration of GMMA protein of less than 200 μg/ml, less than 100 μg/ml or less, 80 μg/ml or less, 50 μg/ml or less, 25 μg/ml or less, 20 μg/ml or less, 15 μg/ml or less, 10 μg/ml or less. Per unit dose, immunogenic compositions of the invention may comprise a total concentration of GMMA protein of from 5 μg/ml to 200 μg/ml, from 5 μg/ml to 100 μg/ml, from 10 μg/ml to 100 μg/ml, from 10 μg/ml to 80 μg/ml, from 10 μg/ml to 50 μg/ml, 25 μg/ml to 50 μg/ml. Per unit dose, immunogenic compositions of the invention may comprise a total concentration of GMMA protein of more than 100 μg/ml, more than 80 μg/ml, more than 50 μg/ml, more than 25 μg/ml, more than 20 μg/ml, more than 15 μg/ml or more than 10 μg/ml.

GMMA protein from each different serotype may be present at an amount from 0.1 to 200 μg, for example from 0.1 to 80 μg, 0.1 to 100 μg and in particular from 5 to 25 μg. Suitable amounts of GMMA from each different serotype may include 0.1, 1, 5, 10, 20, 25, 30, 35, 40, 45, 50, 60, 70, 80, 90 and 100 μg per unit dose.

Briefly, the immunogenic compositions of the invention may be administered in single or multiple doses. A single dose of the immunogenic compositions of the invention may be effective. Alternatively, one unit dose followed by a second unit dose may be effective. Typically, the second (or third, fourth, fifth etc.) unit dose is identical to the first unit dose. The second unit dose may be administered at any suitable time after the first unit dose, in particular after 1, 2 or 3 months. Typically, the immunogenic compositions of the invention will be administered intramuscularly, e.g. by intramuscular administration to the thigh or the upper arm as described below but may also be administered intradermally or intranasally.

Immunogenic compositions of the invention may include one or more adjuvants. Particular adjuvants include aluminium adjuvants, for example, aluminium hydroxide, Alhydrogel, aluminium phosphate, potassium aluminium sulphate and alum. The use of aluminium adjuvants is advantageous since adsorption of GMMA to the adjuvant reduces the pyrogenic response allowing, in rabbits, 100 times higher doses of GMMA to be administered compared to GMMA alone. The use of other adjuvants that also reduce the pyrogenic response is also envisaged and could be identified by the skilled person using the tests exemplified below.

Pharmaceutical Methods and Uses

The immunogenic compositions of the invention may further comprise a pharmaceutically acceptable carrier. Typical 'pharmaceutically acceptable carriers' include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art Immunogenic compositions of the invention may also contain diluents, such as water, saline, glycerol, etc. Additionally, auxiliary substances, such as wetting or emulsifying agents, pH buffering substances, and the like, may be present. Sterile pyrogen-free, Tris-buffered physiologic saline is a preferred carrier particularly when using aluminium adjuvants since the phosphate in phosphate buffered saline may interfere with GMMA binding to aluminium.

Compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a mammal Such kits may comprise one or more antigens in liquid form and one or more lyophilised antigens. Compositions may be presented in vials, or they may be presented in ready-filled syringes. The syringes may be supplied with or without needles. A syringe will include a single dose of the composition, whereas a vial may include a single dose or multiple doses.

Aqueous compositions of the invention are also suitable for reconstituting other vaccines from a lyophilised form. Where a composition of the invention is to be used for such extemporaneous reconstitution, the invention provides a kit, which may comprise two vials, or may comprise one ready-filled syringe and one vial, with the contents of the syringe being used to reactivate the contents of the vial prior to injection.

Compositions of the invention may be packaged in unit dose form or in multiple dose form. For multiple dose forms, vials are preferred to pre-filled syringes. Effective dosage volumes can be routinely established, but a typical human dose of the composition has a volume of 0.5 ml e.g. for intramuscular injection.

The pH of the composition is preferably between 6 and 8, preferably about 7. Stable pH may be maintained by the use of a buffer. The immunogenic compositions of the invention may comprise a Tris [Tris(hydroxymethyl)aminomethane] buffer. The Tris buffer may comprise about 1-20 mM [Tris (hydroxymethyl)aminomethane], e.g. 1.25 mM, 2.5 mM, 5.0 mM or 10.0 mM. The composition will be sterile. Compositions of the invention may be isotonic with respect to humans.

Thus, compositions of the invention may be useful as vaccines. Vaccines according to the invention may either be prophylactic (i.e. to prevent infection) or therapeutic (i.e. to treat infection), but will typically be prophylactic. The term "protected against infection" means that the immune system of a subject has been primed (e.g. by vaccination) to trigger an immune response and repel the infection. It will be clear to those skilled in the art that a vaccinated subject may thus get infected, but is better able to repel the infection than a control subject. The term "treating" includes both therapeutic treatment and prophylactic or preventative treatment, wherein the object is to prevent or lessen infection. For example, treating may include directly affecting or curing, suppressing, inhibiting, preventing, reducing the severity of, delaying the onset of, reducing symptoms associated with, for example, infection, or a combination thereof "Preventing" may refer, inter alia, to delaying the onset of symptoms, preventing relapse to a disease, and the like. Treating may also include "suppressing" or "inhibiting" an infection or illness, for example reducing severity, number, incidence or latency of symptoms, ameliorating symptoms, reducing secondary symptoms, reducing secondary infections, prolonging patient survival, or combinations thereof. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Compositions of the invention may include an antimicrobial, particularly when packaged in multiple dose format. Compositions of the invention may include sodium salts (e.g. sodium chloride) to give tonicity. A concentration of 10±2 mg/ml NaCl is typical. In some embodiments, a concentration of 4 to 10 mg/ml NaCl may be used, e.g. 9.0, 7.0, 6.75 or 4.5 mg/ml. Compositions of the invention will generally include a buffer.

Methods of Treatment

The invention also provides a method for raising an immune response in a suitable mammal, comprising administering a pharmaceutical composition of the invention to the suitable mammal. The immune response is preferably protective and preferably involves antibodies. The method may raise a booster response.

The suitable mammal may be an animal such as a cow, horse, dog, cat and the like but is preferably a human. Where the vaccine is for prophylactic use, the human may be a child (e.g. a toddler or infant) or a teenager; where the vaccine is for therapeutic use, the human may be an adult. A vaccine intended for children may also be administered to adults e.g. to assess safety, dosage, immunogenicity, etc. A preferred class of humans for treatment are females of child-bearing age (e.g. teenagers and above). Another preferred class is pregnant females.

The invention also provides a composition of the invention for use as a medicament. The medicament is preferably able to raise an immune response in a mammal (i.e. it is an immunogenic composition) and is more preferably a vaccine. The invention also provides the use of a composition of the invention in the manufacture of a medicament for raising an immune response in a mammal. These uses and methods are preferably for the prevention and/or treatment of illness and particularly the immune response is a protective immune response.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml. The invention may be used to elicit systemic and/or mucosal immunity. Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

Unless specifically stated, a process comprising a step of mixing two or more components does not require any specific order of mixing. Thus components can be mixed in any order. Where there are three components then two components can be combined with each other, and then the combination may be combined with the third component, etc.

Unless otherwise stated, identity between polypeptide sequences is preferably determined by the Smith-Waterman homology search algorithm as implemented in the MPSRCH program (Oxford Molecular), using an affine gap search with parameters gap open penalty=12 and gap extension penalty=1.

The practice of the present invention will employ, unless otherwise indicated, conventional methods of chemistry, biochemistry, molecular biology, immunology and pharmacology, within the skill of the art. Such techniques are explained fully in the literature.

In some implementations, the term "comprising" refers to the inclusion of the indicated active agent, such as recited polypeptides, as well as inclusion of other active agents, and pharmaceutically acceptable carriers, excipients, emollients, stabilizers, etc., as are known in the pharmaceutical industry. In some implementations, the term "consisting essentially of" refers to a composition, whose only active ingredient is the indicated active ingredient(s), however, other compounds may be included which are for stabilizing, preserving, etc. the formulation, but are not involved directly in the therapeutic effect of the indicated active ingredient. Use of the transitional phrase "consisting essentially" means that the scope of a claim is to be interpreted to encompass the specified materials or steps recited in the claim, and those that do not materially affect the basic and novel characteristic(s) of the claimed invention. See, In re Herz, 537 F.2d 549, 551-52, 190 USPQ 461, 463 (CCPA 1976) (emphasis in the original); see also MPEP § 2111.03. Thus, the term "consisting essentially of" when used in a claim of this invention is not intended to be interpreted to be equivalent to "comprising". The term "consisting of" and variations thereof includes including and limited to unless expressly specified otherwise. The term "about" in relation to a numerical value x means, for example, x+10%, x+5%, x+4%, x+3%, x+2%, x+1%.

MODES FOR CARRYING OUT THE INVENTION

Example A

The Gram-negative outer membrane (OM) is an asymmetric lipid bilayer interspersed with integral OM proteins and peripheral lipoproteins which are often immunogenic and can be exploited as vaccine antigens. Lipoproteins (LPs) are proteins characterized by the presence of a lipidated cysteine which allow the anchoring of this molecule to the membrane (Kovacs-Simon, A., R. W. Titball, and S. L. Michell, Lipoproteins of bacterial pathogens. Infect Immun, 2011. 79(2): p. 548-61).

Two of the main antigens of the multicomponent Bexsero® vaccine against *Meningococcus* group B are lipoproteins, namely Neisserial Heparin Binding Antigen (NHBA) and factor H binding protein (fHbp). In *Neisseria meningitidis*, as well as in other Gram negative bacteria, lipoproteins destined for the OM are synthetized as a precursor in the cytosol and translocated through the Inner Membrane (IM) by the Sec Machinery and then to the Outer Membrane (OM) by the Lol system. The Lol system transports them across the periplasm and secures the proteins to the OM by incorporating the diacylglycerol moiety into the inner leaflet of the OM (Bos, M. P., V. Robert, and J. Tommassen, Biogenesis of the gram-negative bacterial outer membrane. Annu Rev Microbiol, 2007. 61: p. 191-214).

Specific translocation component, SLAM1 (Surface-Lipoprotein Assembly Modulator flippases1), involved in surface exposure of specific *N. meningitidis* lipoproteins, have recently been identified and shown to be sufficient to reconstitute the transport of some meningococcal lipoproteins to *E. coli* surface (fHbp, TbpB and LpbB) (Yogesh Hooda, C. C.-L. L., Andrew Judd, Carolyn M. Buckwalter, Hyejin Esther Shin, Scott D. Gray-Owen and Trevor F. Moraes, Slam is an outer membrane protein that is required for the surface display of lipidated virulence factors in *Neisseria*. Nature microbiology, 2016. 1).

SLAM1 is encoded by nmb0313 gene and it is an outer membrane protein characterized by the presence of an N-terminal domain with a Tetratricopepdide Repeat domain (TPR) and a C-terminal transmembrane domain structured as a porin-like domain (FIG. 1A).

Figure 1B:
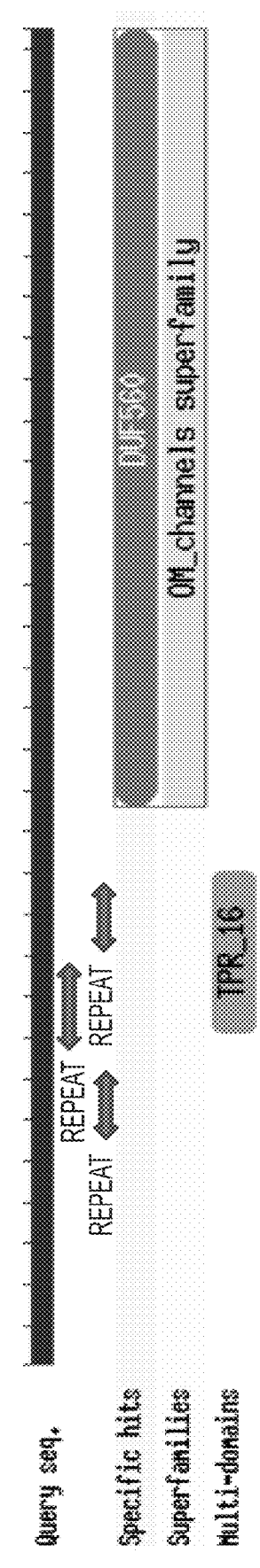
Figure 2:
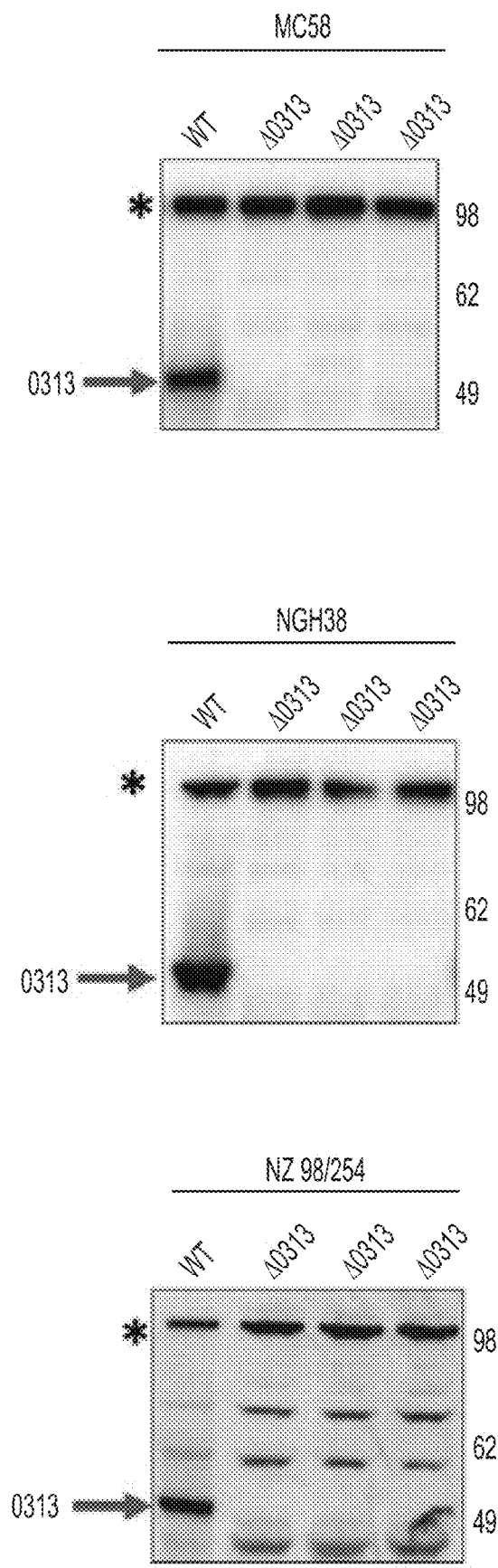
FIG. 2: Western blot analysis of NMB0313 expression in MC58, NGH38 and NZ 98/254 wild type and nmb0313 knockout strains.

In order to better characterize the functionality of this protein, the nmb0313 gene was deleted in different *N. meningitidis* group B representative strains MC58, NGH38 and NZ 98/254 (FIG. 1B). The knockout was obtained by replacing the nmb0313 gene with an antibiotic resistance cassette as follows, results confirmed by Western blotting (FIG. 2).

Bacterial Strains and Culture Conditions

*Neisseria meningitidis* (Nm) serogroup B strains (MC58, NHGH38, NZ 98/254 and its isogenic derivatives) and *Escherichia coli* (Ec) (DH5a and BL21-DE3) strains used in this study are listed in Table 1 below:

| NAME | Description | Antibiotic resistance cassette |
|---|---|---|
| MC58 | Neisseria meningitidis laboratory-adapted reference strain | |
| NGH38 | Neisseria meningitidis | |
| NZ 98/254 | Neisseria meningitidis | |
| MC58 Δ0313 | Neisseria meningitidis MC58 derivative, kanamycin insertion in nmb0313 locus | kanamycin |
| NGH38 Δ0313 | Neisseria meningitidis NGH38 derivative, kanamycin insertion in nmb0313 locus | kanamycin |
| NZΔ0313 | Neisseria meningitidis NZ 98/254 derivative, kanamycin insertion in nmb0313 locus | kanamycin |
| MC58Δ0313 ci0313 | Neisseria meningitidis MC58 derivative, lacking nmb0313 gene with a copy of nmb0313 reintroduced out of locus under the control of an IPTG-inducible PTAC promoter | Chloramphenicol |
| NGH38 Δ0313 ci0313 | Neisseria meningitidis NGH38 derivative, lacking nmb0313 gene with a copy of nmb0313 reintroduced out of locus under the control of an IPTG-inducible PTAC promoter | Chloramphenicol |
| DH5a | E. coli: fhuA2 lac(del)U169 phoA glnV44 Φ80' lacZ(del)M15 gyrA96 recA1 relA1 endA1 thi-1 hsdR17 | |
| BL21 (DE3) | E. coli: | |
| BL21 (DE3) ΔTolR | E. coli: BL21 (DE3) lacking b0738gene | |

*N. meningitidis* strains were grown on Gonococcal (GC) Medium Base (Difco) agar plates or in GC broth at 37° C. in 5% CO2. *E. coli* strains were cultured in LB agar or LB broth at 37° C.

Antibiotics were added when required. Kanamycin and chloramphenicol were added at final concentrations of 150 μg/mL and 5 μg/m for selection of *N. meningitidis* deletion mutants and complementing strains, respectively. Ampicillin, kanamycin, or chloramphenicol was added at final concentrations of 100, 150 or 10 μg/mL for selection *E. coli*.

When required, isopropylβ-D-1-thiogalactopyranoside (IPTG) (1 mM) (Sigma) was added to culture media at the indicated final concentrations.

Construction of Mutant and Complementation Strains

DNA manipulations were carried out using standard laboratory methods (Sambrook J, F. E., Maniatis T, Molecular cloning: a laboratory manual. Cold Spring Harbor Laboratory, 1989. 2nd ed).

To construct the NMB0313 deletion mutant, the nmb0313 gene was replaced with a kanamycin cassette by double crossing over. To do this, plasmid pGEMTUD313Kan was generated as follows. Upstream and downstream flanking regions of nmb0313 were amplified from the MC58 chromosome with restriction enzyme sites and cloned into pGEMT plasmid. Kanamycin cassette was cloned as 1.4 kb XbaI fragment into the XbaI site between the two flanking regions. This plasmid was used to transform *N. meningitidis* strains.

Complementation of nmb0313 was achieved by insertion of a copy of the nmb0313 in the noncoding region between the converging ORF NMB1428 and NMB1429 of Δ0313 strains chromosome. To do this, plasmid pComPIndNMB0313 was generate by amplifying nmb0313 gene and cloned as AseI/NsiI fragment under the control of the inducible promoter Tac and the LacI repressor into pComPInd plasmid (Ieva, R., et al., CrgA is an inducible LysR-type regulator of *Neisseria meningitidis*, acting both as a repressor and as an activator of gene transcription. J Bacteriol, 2005. 187(10): p. 3421-30). Primers and plasmids are listed in Tables 2 and 3 below:

TABLE 2

| NAME | Description | Antibiotic resitance cassette | Reference |
|---|---|---|---|
| pCOLA DUET | The vector encodes two multiple cloning sites. with T7 promoter, COLA replicon from ColA, lacI repressor and KanR | Kanamycin | Novagen |
| pGEM-T | E. coli cloning vector, AmpR | Ampicillin | Promega |
| pComP$_{IND}$ CmR | Plasmid for allelic replacement at a chromosomal location between ORFs NMB1428 and NMB1429 and inducible expression under the control of the PTAC promoter and the lacI repressor. Upstream of the cloning site is a Cm resistance cassette | Ampicillin, Chloramphenicol | Ieva, R., et al. J Bacteriol, 2005. |
| pUD0313Kan | pGEM-T containing the flanking region of nmb0313 with Kan resistance cassette cloned as XmaI fragment between flanking regions | Ampicillin, Kanamycin | this study |
| pIND NHBA-fHbp (pIND N-f fusion) | Plasmid for the complementation of the NHBA-fHbp fusion protein with the N-term of NHBA and the C-term domain in the Com region with an IPTG-inducible Tac promoter. | Ampicillin, Chloramphenicol | this study |
| pIND0313 | Plasmid for the complementation of nmb0313 in the Com region with an IPTG-inducible tac prmoter. Downstream of nmb0313 is cloned a Cm resistance cassette. | Ampicillin, Chloramphenicol | this study |
| pCOLA_0313 | Construct to express recombinant *N. meningitidis* NMB0313 protein in *E. coli* | Kanamycin | this study |

TABLE 2-continued

| NAME | Description | Antibiotic resitance cassette | Reference |
|---|---|---|---|
| pIND NHBA | Construct express recombinant *N. meningitidis* MC58 NHBA variant p3 protein in *E. coli* | Ampicillin, Cloramphenicol | this study |
| pIND fHbp | Construct express recombinant *N. meningitidis* MC58 fhbp variant v1.1 protein in *E. coli* GeneArt construct with N-term NHBA domain fused with the C-term fHbp domain | Ampicillin, Cloramphenicol Ampicillin | this study this study |

TABLE 3

| Primer Name | Application | Sequence |
|---|---|---|
| 0313UP_F | fragment for 0313 KO generation in MenB | GAGATCTAGAGCCGGCATTCGGG CAAAAACC |
| 0313UP_R | fusion primer UP & DO flank of NMB0313 with XmaI restriction site | AACAGCAACCCGGGTATCAATCG GCGGAT |
| NMB0313_FW_DO | fusion primer UP & DO flank of NMB0313 with XmaI restriction site | CCGATTGATACCCGGGTTGCTGT TCCTTTTCG |
| 0313pC_F | cloning NMB0313 gene in pCOM plasmid for complementarion in MENB NM0313KO | GTGTATTAATATGGTTATTTTTT ATTTTTGTG |
| 0313pC_R | cloning NMB0313 in pCOM plasmid for complementarion in MENB NM0313KO | GTGTATGCATTCAGAACGTTTTA TTAAACTC |
| 0313pD_F2 | cloning NMB0313 gene in MCS2 of pCOLA | GTGTATTAATATGGTTATTTTTT ATTTTTGTG |
| 0313pD_R2 | cloning NMB0313 gene in MCS2 of pCOLA | GTGTCTCGAGTCAGAACGTTTTA TTAAACTC |

The correct nucleotide sequence of each plasmid was confirmed by DNA sequencing. Plasmids were linearized and used for the transformation of the *N. meningitidis* strains. All transformants were verified both by PCR analysis and Western blot as follows:

Western Blot Analysis

Strains grown overnight on agar plates were re-suspended in GC broth to an $OD_{600}$ of 0.5. 1 mL of the resuspension was centrifuged for 5 min at 13000 rpm and the pellet was re-suspended in 50 µl of SDS loading buffer (50 mM Tris-HCl [pH 6.8], 2.5% SDS, 0.1% bromophenol blue, 10% glycerol, 5% β-mercaptoethanol, 50 mM DTT) (Oriente, F., V. Scarlato, and I. Delany, Expression of factor H binding protein of meningococcus responds to oxygen limitation through a dedicated FNR-regulated promoter. J Bacteriol, 2010. 192(3): p. 691-701).

Liquid cultures were grown until an $OD_{600}$ of 0.50 was reached and 1 mL of the culture was pelleted and re-suspended in 50 µl of SDS loading buffer. Protein extracts were separated by SDS-PAGE on NuPAGE Novex® 4-12% Bis-Tris Protein Gels in MES 1× (Life Technologies) and then transferred to nitrocellulose membranes. Membranes were blocked overnight at 4° C. with PBS+0.05% Tween 20 (Sigma) and 10% powdered milk (Sigma). Primary antibody were diluted (Table 4) in PBS+0.05% Tween 20 and 3% powdered milk and incubated for 1 h with the membrane.

| Tables of antibodies | WB dilution | FACS dilution |
|---|---|---|
| α-fHbp polyclonal serum mouse | 1:5000 | 1:1000 |
| α-NHBA polyclonal mouse serum | 1:2000 | 1:1000 |
| α-NHBA monoclonal mouse serum |  | 1:1000 |
| α-mouse-FITC |  | 1:1000 |
| α-mouse-HRP | 1:1000 |  |

A horseradish peroxidase (HRP)-conjugated anti-mouse IgG antibody and the Western Lightning ECL (Perkin Elmer) were used according to the manufacturer's instructions for the detection. Results are shown in FIG. 2).

After the generation of the nmb0313KO, mutants were analysed by the presence on the surface of know surface exposed lipoproteins like NHBA and fHbp:

Fluorescence Activated Cell Sorting (FACS) Analysis of fHbp/NHBA Expression

Figure 3:
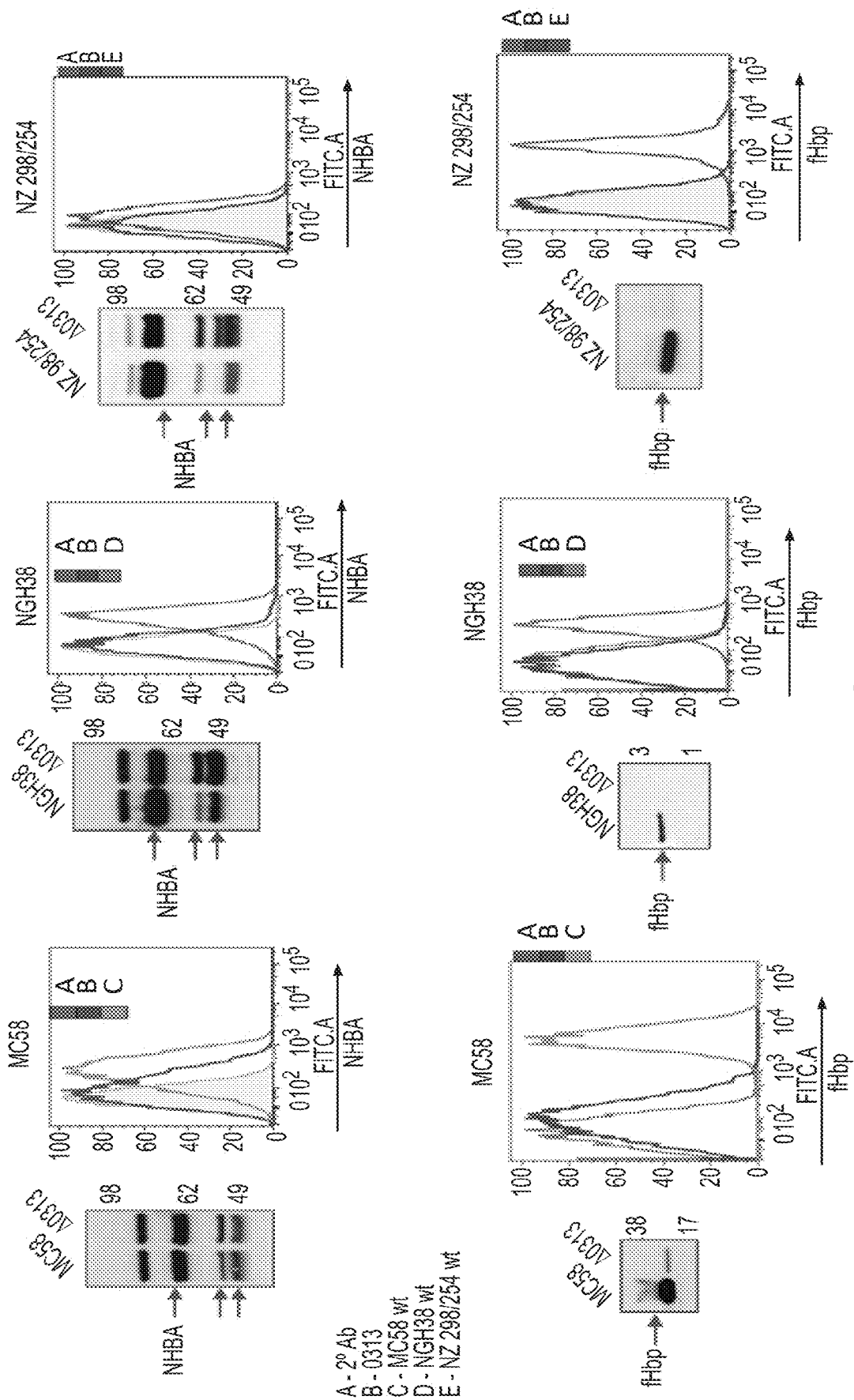
FIG. 3: Analysis of expression and surface exposure of fHbp and NHBA lipoproteins in nmb0313KO strains by western blot and FACS.

*N. meningitidis* strains and isogenic derivatives, were collected after liquid cultures at $OD_{600}$ 0.5, when required IPTG was also added. Bacteria were inactivated by incubation with formaldehyde 0.5% for 1 hour at room temperature. Labelling was performed with primary antibody diluted in PBS-0.5% BSA (Sigma) as reported in Table 4. Primary antibody binding was detected using an anti-mouse (whole-molecule) FITC-conjugated antibody (Sigma) at the properly dilution (FIG. 3).

The deletion of nmb0313 affects the surface exposure of the analysed lipoproteinss in the selected menigococcal strains. In particular, the absence of NMB0313 results in a lack of detectable levels of NHBA on the cell surface with concomitant accumulation of NHBA within the bacteria. In contrast, decreased fHbp levels were detected on the cell surface and these low levels were a consequence of a general reduction of fHbp amount in the nmb0313 KO background as compared to the wild type. Therefore NMB0313 plays a critical role in translocation of NHBA to the surface of the bacterium but its deletion does not affect NHBA expression per se. However, NMB0313 contributes to the stable expression of fHbp and hence its surface expression.

Subsequently the phenotype was restored in NGH38 nmb0313 KO strain by genomic complementation of a functional copy of nmb0313 gene under the control of the IPTG inducible Tac promoter (FIG. 4A). The complemented strain is able to express NMB0313 in an IPTG-dependent manner as demonstrated by western blot and the highest concentrations of IPTG induce an overexpression of the NMB0313 protein with respect to the wild type levels (FIG. 4B).

Figure 5A:
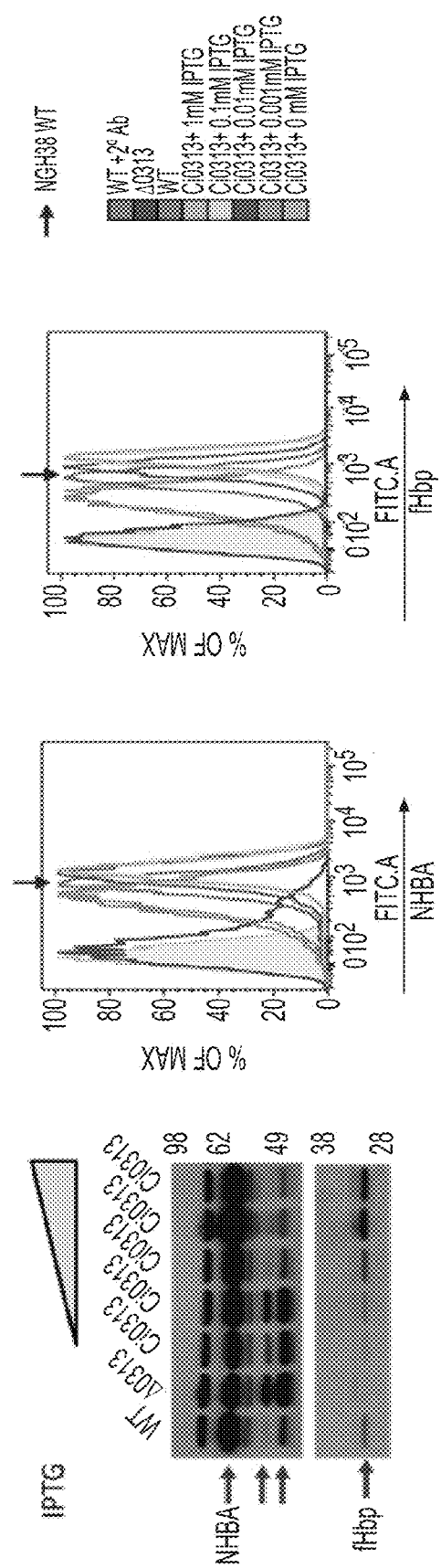
FIGS. 5A-5B: Analysis of fHbp and NHBA lipoproteins expression and surface exposure in nmb0313 complemented NGH38 strain by A) western blot and FACS; B) In the charts are reported the percentage of the mean fluorescence (MFI) extrapolate from FACS analysis of fHbp or NHBA in respect to the wt levels at the different IPTG concentration.
Figure 5B:
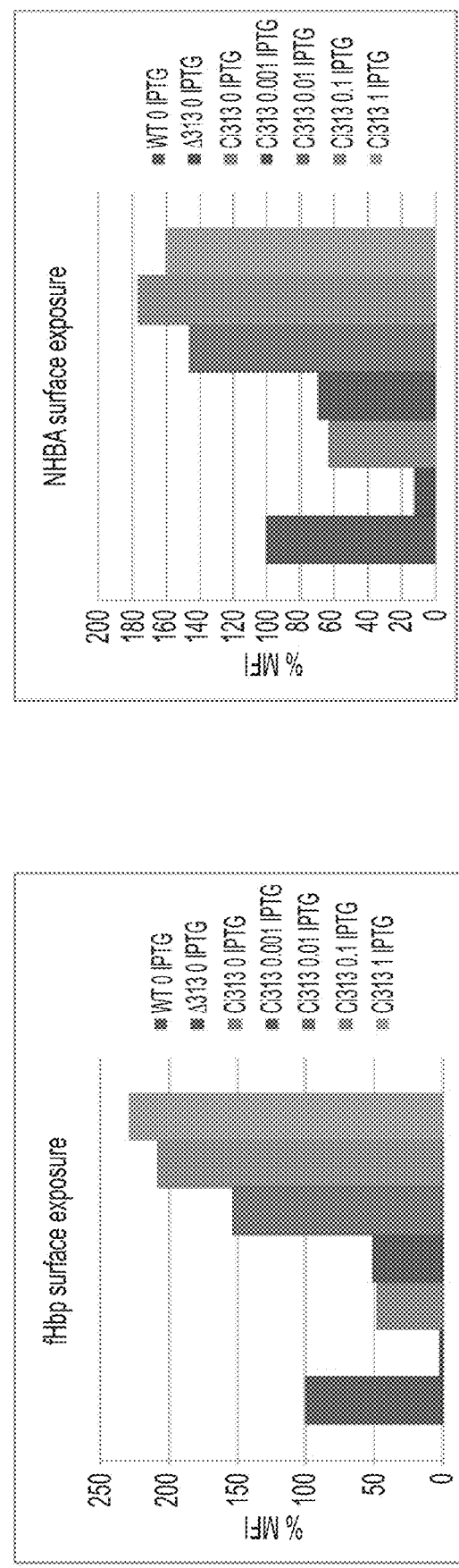

The complemented strain was than analysed for the surface exposure of NHBA and fHbp (FIG. 5A-5B). The surface expression of NHBA and fHbp was restored in the nmb0313 complemented strain. Interestingly, increasing expression levels of NMB0313 resulted in concomitant increase in surface expression of both NHBA and fHbp as seen by FACS analyses and surprisingly, the overexpression of NMB0313, at 0.1 and 1 mM concentration of IPTG, resulted in higher surface levels of NHBA and fHbp than in the wildtype strain. From Western blot this appears to be due to increased expression levels of these lipoproteins in the NMB0313 overexpressing strain.

Co-Expression of Flippase With Lipoproteins in a Heterologous System

The fHbp and NHBA lipoproteins from *N. meningitidis* MC58 were cloned under the control of an IPTG-inducible promoter and expressed in non-pathogenic *Escherichia coli* strain alone or with co-expression of NMB0313. *E. coli* BL21 (DE3) strain was co-transformed with two different comparable plasmids carrying fHbp or NHBA and nmb0313, respectively or as negative control one plasmid carrying fHBP or NHBA and the pCOLA empty plasmid. Expression levels of both proteins responded to IPTG induction and the expression of both proteins were confirmed by WB analysis (FIG. 6A-6D).

In the presence of NMB0313 the amount of fHbp in the total extracts strongly increased compared to the strain expressing fHbp alone. This increased level of fHbp was reflected by higher detectable fHbp on *E. coli* surface.

The expression of fHbp alone is detectable both in Western Blot and by FACS on the surface of *E. coli* only at concentrations of 0.01 and 0.1 mM IPTG, however on concomitant co-expression of NMB0313 expression is detectable also at concentrations of 0.001 mM IPTG and at the higher levels of IPTG the co-expression of NMB0313 results in significantly more expression of fHBP overall and on the surface of *E. coli*. These results indicate that NMB0313 has a positive effect on the stable expression and surface expression of fHBP in *E. coli*.

Preliminary results of NHBA expression in *E. coli* strains evidence the stable expression of NHBA in the samples both in the presence or absence of NMB0313, while FACS analysis reveal that no NHBA is detectable on the *E. coli* cell surface. However, when NHBA is expressed with NMB0313 bacteria also show NHBA on the surface, confirming the key role of NMB0313 in the NHBA translocation across the surface.

Production of OMVs From Strains Expressing Flippases

The NGH38 complemented strain described above, is used to produce outer membrane vesicles. Briefly, to abolish capsule production a fragment of the bacterial chromosome containing synX, ctrA and the promoter controlling their expression, is replaced with a spectinomycin-resistance gene. First, the recombination sites are amplified from genomic DNA with the following primers:

```
ctrAf_Xma:    CCCCCCGGGCAGGAAAGCGCTGCATAG    [SEQ ID NO: 10]

ctrAr_Xba     CGTCTAGAGGTTCAACGGCAAATGTGC;   [SEQ ID NO: 11]

Synf_Kpn      CGGGGTACCCGTGGAATGTTTCTGCTCAA  [SEQ ID NO: 12]

Synr_Spe      GGACTAGTCCATTAGGCCTAAATGCCTG   [SEQ ID NO: 13]
```

The fragments are inserted into plasmid pComPtac (Ieva et al., J Bacteriol, 187 (2005), pp. 3421-3430) upstream and downstream of the chloramphenicol resistance gene. Subsequently the chloramphenicol resistance gene is replaced with a spectinomycin resistance cassette. The lpxL1 gene is deleted by replacement with a kanamycin resistance gene (Koeberling et al., J Infect Dis, 198 (2008), pp. 262-270) and the gna33 gene with an erythromycin resistance cassette (Adu-Bobie et al., Infect Immun, 72 (2004), pp. 1914-1919).

GMMA Preparation

Bacteria are grown at 37° C., 5% CO2 in 50 mL of a meningococcus defined medium at 180 rpm until early stationary phase. Cells were harvested (2200 g, 30 min, 4° C.) and the culture supernatant containing the GMMA is filtered through a 0.22 μm pore-size membrane (Millipore, Billerica, Mass., USA). To collect GMMA, the supernatant is ultracentrifuged (142,000×g, 2 h, 4° C.). The membrane pellet is washed with phosphate buffered saline (PBS), resuspended in PBS and sterile filtered. GMMA concentration is measured according to protein content by Lowry assay (Sigma-Aldrich, St. Louis, Mo., USA). For protein and lipooligosaccharide analysis, GMMA are separated by SDS-PAGE using a 12% gel and MOPS or MES buffer (Invitrogen, Carlsbad, Calif., USA). Total proteins are stained with Coomassie Blue stain. fHbp is detected by Western blot using a polyclonal antibody as described above.

Mouse Immunization

Female CD-1 mice are obtained from Charles River Laboratories (Wilmington, Mass., USA). Eight mice per group are immunised intraperitoneally three times with 2 weeks intervals. Serum samples are obtained 2 weeks after the third dose. OMVs from the flippase over-expressing strain are given at 0.2, 1 and 5 μg doses based on total protein. Control mice are immunised with 5 μg aluminium hydroxide only. All vaccines are adsorbed on 3 mg/mL Aluminium hydroxide in a 100 μL formulation containing 10 mM Histidine and 0.9 mg/mL NaCl. Sera are stored at −80° C. until use. All animal work was approved by the Italian Animal Ethics Committee.

Serological Analysis

Anti-fHbp IgG antibody titres are measured by ELISA as described in Beemink et al. (Clin Vaccine Immunol, 17 (2010), pp. 1074-1078).

While certain embodiments of the present invention have been described and specifically exemplified above, it is not intended that the invention be limited to such embodiments. Various modifications may be made thereto without departing from the scope and spirit of the present invention as set forth in the following claims.

```
Sequences
>SEQ ID NO: 1; gi|77358697:323429-324895 Neisseria
meningitidis MC58
ATGGTTATTTTTTATTTTTGTGGGAAGACATTTATGCCTGCACGAAACAGATGGATGCTG

CTGCTGCCTTTATTGGCAAGCGCGGCATATGCCGAAGAAACACCGCGCGAACCGGATTT

GAGAAGCCGTCCCGAGTTCAGGCTTCATGAAGCGGAGGTCAAACCGATCGACAGGGAG
```

```
AAGGTGCCGGGGCAGGTGCGGGAAAAAGGAAAAGTTTTGCAGATTGACGGCGAAACCC

TGCTGAAAAATCCCGAATTGTTGTCCCGCGCGATGTATTCCGCAGTGGTCTCAAACAAT

ATTGCCGGTATCCGCGTTATTTTGCCGATTTACCTACAACAGGCGCAGCAGGATAAGAT

GTTGGCACTTTATGCACAAGGGATTTTGGCGCAGGCAGACGGTAGGGTGAAGGAGGCG

ATTTCCCATTACCGGGAATTGATTGCCGCCCAACCCGACGCGCCCGCCGTCCGTATGCGT

TTGGCGGCAGCATTGTTTGAAAACAGGCAGAACGAGGCGGCGGCAGACCAGTTCGACC

GCCTGAAGGCGGAAAACCTGCCGCCGCAGCTGATGGAGCAGGTCGAGCTGTACCGCAA

GGCATTGCGCGAACGCGATGCGTGGAAGGTAAATGGCGGCTTCAGCGTCACCCGCGAA

CACAATATCAACCAAGCCCCGAAACGGCAGCAGTACGGCAAATGGACTTTCCCGAAAC

AGGTGGACGGCACGGCGGTCAATTACCGGCTCGGCGCGGAGAAAAAATGGTCGCTGAA

AAACGGCTGGTACACGACGGCGGGCGGCGACGTGTCCGGCAGGGTTTATCCGGGGAAT

AAGAAATTCAACGATATGACGGCAGGCGTTTCCGGCGGCATCGGTTTTGCCGACCGGCG

CAAAGATGCCGGGCTGGCAGTGTTCCACGAACGCCGCACCTACGGCAACGACGCTTATT

CTTACACCAACGGCGCACGCCTTTATTTCAACCGTTGGCAAACCCCGAAATGGCAAACG

TTGTCTTCGGCGGAGTGGGGCGTTTGAAGAATACGCGCCGGGCGCGTTCCGACAATAC

CCATTTGCAAATTTCCAATTCGCTGGTGTTTTACCGGAATGCGCGCCAATATTGGATGGG

CGGTTTGGATTTTTACCGCGAGCGCAACCCCGCCGACCGGGGCGACAATTTCAACCGTT

ACGGCCTGCGCTTTGCCTGGGGGCAGGAATGGGGCGGCAGCGGCCTGTCTTCGCTGTTG

CGCCTCGGCGCGGCGAAACGGCATTATGAAAAACCCGGCTTTTTCAGCGGTTTTAAAGG

GGAAAGGCGCAGGGATAAAGAATTGAACACATCCTTGAGCCTTTGGCACCGGGCATTGC

ATTTCAAAGGCATCACGCCGCGCCTGACGTTGTCGCACCGCGAAACGCGGAGTAACGAT

GTGTTCAACGAATACGAGAAAAATCGGGCGTTTGTCGAGTTTAATAAAACGTTCTGA

>SEQ ID NO: 2 Q9K165|Y0313_NEIMB TPR repeat-containing
protein NMB0313
MVIFYFCGKTFMPARNRWMLLLPLLASAAYAEETPREPDLRSRPEFRLHEAEVKPIDREKVP

GQVREKGKVLQIDGETLLKNPELLSRAMYSAVVSNNIAGIRVILPIYLQQAQQDKMLALYA

QGILAQADGRVKEAISHYRELIAAQPDAPAVRMRLAAALFENRQNEAAADQFDRLKAENLP

PQLMEQVELYRKALRERDAWKVNGGFSVTREHNINQAPKRQQYGKWTFPKQVDGTAVNY

RLGAEKKWSLKNGWYTTAGGDVSGRVYPGNKKFNDMTAGVSGGIGFADRRKDAGLAVFH

ERRTYGNDAYSYTNGARLYFNRWQTPKWQTLSSAEWGRLKNTRRARSDNTHLQISNSLVF

YRNARQYWMGGLDFYRERNPADRGDNFNRYGLRFAWGQEWGGSGLSSLLRLGAAKRHY

EKPGFFSGFKGERRRDKELNTSLSLWHRALHFKGITPRLTLSHRETRSNDVFNEYEKNRAFV

EFNKTF

>SEQ ID NO: 3 tr|Q9JXM5|Q9JXM5_NEIMB Uncharacterized protein
MLYFRYGFLVVWCAAGVSAAYGADAPAILDDKALLQVQRSVSDKWAESDWKVENDAPR

VVDGDFLLAHPKMLEHSLRDALNGNQADLIASLADLYAKLPDYDAVLYGRARALLAKLAG

RPAEAVARYRELHGENAADERILLDLAAAEFDDFRLKSAERHFAEAAKLDLPAPVLENVGR

FRKKTEGLTGWRFSGGISPAVNRNANNAAPQYCRQNGGRQICSVSRAERAAGLNYEIEAEK

LTPLADNHYLLFRSNIGGTSYYFSKKSAYDDGFGRAYLGWQYKNARQTAGILPFYQVQLSG

SDGFDAKTKRVNNRRLPPYMLAHGVGVQLSHTYRPNPGWQFSVALEHYRQRYREQDRAE
```

-continued

```
YNNGRQDGFYVSSAKRLGESATVFGGWQFVRFVPKRETVGGAVNNAAYRRNGVYAGWA

QEWRQLGGLNSRVSASYARRNYKGIAAFSTEAQRNREWNVSLALSHDKLSYKGIVPALNY

RFGRTESNVPYAKRRNSEVFVSADWRF

>SEQ ID NO: 4 tr|A0A0Y0BKC0|A0A0Y0BKC0_STREE TPR repeat-
containing protein NMB0313; Streptococcus pneumoniae
MSIQTKFILFLSSSLFLTPYSVATEKSPQPHDGRLDEQLHLAKPNLPQKPTALLTNNNPSKLSI

TKEELAKHPDLIIRGLIPAVLQNNGEAVQLLLPLYQPLPKKDPFLLEWAEAIDLREKGHFSDS

VKAYRHLFSQKTDLLPLRYQLAQALFLNNDNEAAKDQFQKLRAEQVSPDSVKIIEQYLSAL

NQRDQWKIQGGFSFLNESNINNAPKAGTKIGNWTAWEKESARGFSYFGNAEKKWSLPHNH

FTKLSLEGSGKYYWDNKKYNEFNARAGAGLGYQTARFEVSLMPFTEKRWYVGGSSGGNA

MKQYSKNSGARLDLSNWLNEKWQISTALEYGEQRYETRKHLNGNNYLASATLLYLAKSGQ

YWFGGADYNRENTRDLDNAYQRKNVRLGWGQEWKAGISTRLILNYARRAYKEKDLIGIRQ

KNKEYASVFTIWHRNFHIWGITPKLSWSYQKVTSNHPFYEYDKNRIYVEISKTF

>SEQ ID NO 5: R2846_1315
MKNGVKQLSLLSLIGLSLTNVAWAEVARPKNDTLTNTIQSAELKTSSFSSMPKKEIPNRH

IISLSKSQLAHHPRLVLRGLIPALYQNNTQAVQLLLPLYKQFPQQDNFLLTWAKAIEARE

QGDLTQSIAYYRELFARNASLLPLRYQLAQALFFNYENEAAKIQFEKLRTEVDDEKFLGV

IDQYLLTLNQRNQWIWQVGLNFLNDDNLNNAPKSGTKIGSWTAWEKESGQGVGYSLSVEK

KWPWADHFFSKTMFNGNGKYYWDNKKYNEATVRIGGGLGYQTASVEVSLFPFQEKRWYA

G GSSGTNTMKQYADKLGIRLENVDWLSKTWQISTALEYGESRYKIRKHLDGNYYFISSTLF

YLPKSTQFWFVGMDFHRENTQALDNAYQQKTLRLGWGQDWSHGISSRLTFSYANRVYREK

DLIGIQQKNREYTTTITLWHRNIHFMGLTPKLSWDYQKSTSNHAFYRYDKNRIYLEIGKIF

>SEQ ID NO 6: NadA
ATNDDDVKKAATVAIAAAYNNGQEINGFKAGETIYDIDEDGTITKKDATAADVEADDFKGL

GLKKVVTNLTKTVNENKQNVDAKVKAAESEIEKLTTKLADTDAALADTDAALDATTNALN

KLGENITTFAEETKTNIVKIDEKLEAVADTVDKHAEAFNDIADSLDETNTKADEAVKTANEA

KQTAEETKQNVDAKVKAAETAAGKAEAAAGTANTAADKAEAVAAKVTDIKADIATNKDN

IAKKANSADVYTREESDSKFVRIDGLNATTEKLDTRLASAEKSIADHDTRLNGLDKTVSDLR

KETRQGLAEQAALSGLFQPYNVG

>SEQ ID NO: 7 gi|7227388|gb|AAF42440.1| transferrin-binding
protein-related protein [Neisseria meningitidis MC58]
MFKRSVIAMACIFALSACGGGGGSPDVKSADTLSKPAAPVVSEKETEAKEDAPQAGSQGQ

GAPSAQGSQDMAAVSEENTGNGGAVTADNPKNEDEVAQNDMPQNAAGTDSSTPNHTPDP

NMLAGNMENQATDAGESSQPANQPDMANAADGMQGDDPSAGGQNAGNTAAQGANQAG

NNQAAGSSDPIPASNPAPANGGSNFGRVDLANGVLIDGPSQNITLTHCKGDSCSGNNFLDEE

VQLKSEFEKLSDADKISNYKKDGKNDKFVGLVADSVQMKGINQYIIFYKPKPTSFARFRRSA

RSRRSLPAEMPLIPVNQADTLIVDGEAVSLTGHSGNIFAPEGNYRYLTYGAEKLPGGSYALR

VQGEPAKGEMLAGAAVYNGEVLHFHTENGRPYPTRGRFAAKVDFGSKSVDGIIDSGDDLH

MGTQKFKAAIDGNGFKGTWTENGSGDVSGKFYGPAGEEVAGKYSYRPTDAEKGGFGVFA

GKKEQD

SEQ ID NO: 8
MPSEPPFGRHLIFASLTCLIDAVCKKRYHNQNVYILSILRMTRSKPVNRTAFCCLSLTTALILT

ACSSGGGGVAADIGAGLADALTAPLDHKDKGLQSLTLDQSVRKNEKLKLAAQGAEKTYGN

GDSLNTGKLKNDKVSRFDFIRQIEVDGQLITLESGEFQVYKQSHSALTAFQTEQIQDSEHSGK
```

-continued

MVAKRQFRIGDIAGEHTSFDKLPEGGRATYRGTAFGSDDAGGKLTYTIDFAAKQGNGKIEH

LKSPELNVDLAAADIKPDGKRHAVISGSVLYNQAEKGSYSLGIFGGKAQEVAGSAEVKTVN

GIRHIGLAAKQ

SEQ ID NO: 9
CSSGGGGSGGGGVAADIGAGLADALTAPLDHKDKGLKSLTLEDSISQNGTLTLSAQGAERT

FKAGDKDNSLNTGKLKNDKISRFDFIRQIEVDGQLITLESGEFQIYKQDHSAVVALQIEKINNP

DKIDSLINQRSFRVSGLGGEHTAFNQLPDGKAEYHGKAFSSDDAGGKLTYTIDFAAKQGHG

KIEHLKTPEQNVELAAAELKADEKSHAVILGDTRYGSEEKGTYHLALFGDRAQEIAGSATVK

IGEKVHEIGIAGKQ

REFERENCES

1. A. Kulp, M. J. Kuehn Biological functions and biogenesis of secreted bacterial outer membrane vesicles Annual Review of Microbiology, 64 (2010), pp. 163-184
2. S. F. Berlanda, A. M. Colucci, L. Maggiore, S. Sanzone, O. Rossi, I. Ferlenghi, et al. High yield production process for Shigella outer membrane particles, PLoS One, 7 (2012), p. e35616.
1. Murray C J, Vos T, Lozano R, Naghavi M, Flaxman A D, Michaud C, et al. Disability-adjusted life years (DALYs) for 291 diseases and injuries in 21 regions, 1990-2010: a systematic analysis for the Global Burden of Disease Study 2010. Lancet. 2012; 380: 2197-2223.
2. Lozano R, Naghavi M, Foreman K, Lim S, Shibuya K, Aboyans V, et al. Global and regional mortality from 235 causes of death for 20 age groups in 1990 and 2010: a systematic analysis for the Global Burden of Disease Study 2010. Lancet. 2012; 380: 2095-2128.
3. Kotloff K L, Nataro J P, Blackwelder W C, Nasrin D, Farag T H, Panchalingam S, et al. Burden and aetiology of diarrhoeal disease in infants and young children in developing countries (the Global Enteric Multicenter Study, GEMS): a prospective, case-control study. Lancet. 2013; 382: 209-222.
4. Livio S, Strockbine N A, Panchalingam S, Tennant S M, Barry E M, Marohn M E, et al. *Shigella* isolates from the global enteric multicenter study inform vaccine development. Clin Infect Dis. 2014; 59: 933-941.
5. Levine M M, Kotloff K L, Barry E M, Pasetti M F, Sztein M B. Clinical trials of *Shigella* vaccines: two steps forward and one step back on a long, hard road. Nat Rev Microbiol. 2007; 5: 540-553.
6. Chang Z, Lu S, Chen L, Jin Q, Yang J. Causative species and serotypes of shigellosis in mainland China: systematic review and meta-analysis. PLoS One. 2012; 7: e52515.
7. Vinh H, Nhu N T K, Nga T V T, Duy P T, Campbell J I, Hoang N V M, et al. A changing picture of shigellosis in southern Vietnam: shifting species dominance, antimicrobial susceptibility and clinical presentation. BMC Infect Dis. 2009; 9: 204.
8. Kweon, 2008 Curr Opin Infect Dis. 21(3):313-8.
9. Cohen D, Ashkenazi S, Green M S, Gdalevich M, Robin G, Slepon R, et al. Double-blind vaccine-controlled randomised efficacy trial of an investigational *Shigella* sonnei conjugate vaccine in young adults. Lancet. 1997; 349: 155-159.
10. Passwell J H, Ashkenzi S, Banet-Levi Y, Ramon-Saraf R, Farzam N, Lerner-Geva L, et al. Age-related efficacy of *Shigella* O-specific polysaccharide conjugates in 1-4-year-old Israeli children. Vaccine. 2010; 28: 2231-2235.
11. Susanna Esposito, Roman Prymula, Gian Vincenzo Zuccotti, Fang Xie, Michelangelo Barone, Peter M Dull, Daniela Toneatto, A phase II randomized controlled trial of a multicomponent meningococcal serogroup B vaccine, 4CMenB, in infants (II). Human Vaccines & Immunotherapeutics Vol. 10, Iss. 7, 2014.
12. Erlandson and Mackey (1958) J Bacteriol 75(3): 253-7.
13. U.S. Pat. No. 5,681,736.
14. Uyttendaele et al. (2001) International journal of food microbiology 70(3):255-65.
15. Formal S B, Kent T H, May H C, Palmer A, Falkow S, LaBrec E H. Protection of monkeys against experimental shigellosis with a living attenuated oral polyvalent dysentery vaccine. J Bacteriol. 1966; 92: 17-22.
16. Makino S, Sasakawa C, Kamata K, Kurata T, Yoshikawa M. A genetic determinant required for continuous reinfection of adjacent cells on large plasmid in *S. flexneri* 2a. Cell. 1986; 46: 551-555.
17. Berlanda Scorza F, Colucci A M, Maggiore L, Sanzone S, Rossi O, Ferlenghi I, et al. High yield production process for *Shigella* outer membrane particles. PLoS One. 2012; 7: e35616.
18. Prunier A-L, Schuch R, Fernandez R E, Mumy K L, Kohler H, McCormick B A, et al. nadA and nadB of *Shigella flexneri* 5a are antivirulence loci responsible for the synthesis of quinolinate, a small molecule inhibitor of *Shigella* pathogenicity. Microbiology. 2007; 153: 2363-2372.
19. Clementz T, Bednarski J J, Raetz C R. Function of the htrB high temperature requirement gene of *Escherchia coli* in the acylation of lipid A. J Biol Chem. 1996; 271: 12095-12102.
20. Rossi O, Pesce I, Giannelli C, Aprea S, Caboni M, Citiulo F, et al. Modulation of Endotoxicity of *Shigella* Generalized Modules for Membrane Antigens (GMMA) by Genetic Lipid A Modifications: Relative Activation of TLR4 and TLR2 Pathways in Different Mutants. J Biol Chem. 2014; 289: 24922-24935.
21. Micoli F, Rondini S, Gavini M, Pisoni I, Lanzilao L, Colucci A M, et al. A scalable method for O-antigen purification applied to various *Salmonella serovars*. Anal Biochem. 2013; 434: 136-145.
22. Robbins J B, Kubler-Kielb J, Vinogradov E, Mocca C, Pozsgay V, Shiloach J, et al. Synthesis, characterization, and immunogenicity in mice of *Shigella* sonnei O-specific oligosaccharide-core-protein conjugates. Proc Natl Acad Sci USA. 2009; 106: 7974-7978.

23. Westphal O, Jann K. Bacterial lipopolysaccharides: extraction with phenol-water and further application of the procedure. 1965; 5: 83-91.
24. Stoddard M B, Pinto V, Keiser P B, Zollinger W. Evaluation of a whole-blood cytokine release assay for use in measuring endotoxin activity of group B *Neisseria meningitidis* vaccines made from lipid A acylation mutants. Clin Vaccine Immunol. 2010; 17: 98-107.
25. Pyrogens. In: European Pharmacopoeia. 8th ed. Strasbourg, Cedex: Directorate for the Quality of Medicines & HealthCare of the Council of Europe (EDQM). 2013. chapter 2.6.8.
26. Moscardo E, Maurin A, Dorigatti R, Champeroux P, Richard S. An optimised methodology for the neurobehavioural assessment in rodents. J Pharmacol Toxicol Methods. 2007; 56: 239-255.
27. Jiang Y, Yang F, Zhang X, Yang J, Chen L, Yan Y, et al. The complete sequence and analysis of the large virulence plasmid pSS of *Shigella* sonnei. Plasmid. 2005; 54: 149-159.
28. Rossi O, Maggiore L, Necchi F, Koeberling O, MacLennan C A, Saul A, et al. Comparison of Colorimetric Assays with Quantitative Amino Acid Analysis for Protein Quantification of Generalized Modules for Membrane Antigens (GMMA). Mol Biotechnol. 2014; in press.
29. WO99/57280
30. Tettelin et al. (2000) Science 287:1809-1815.
31. Comanducci et al. (2002) J. Exp. Med. 195:1445-1454.
32. WO03/010194.
33. WO00/66741
34. Masignani et al. (2003) J Exp Med 197:789-799.
35. Welsch et al. (2004) J Immunol 172:5605-15.
36 Hou et al. (2005) J Infect Dis 192(4):580-90.
37. WO03/063766.
38. Fletcher et al. (2004) Infect Immun 72:2088-2100.
39. Zhu et al. (2005) Infect Immun 73(10):6838-45.
40. Cantini et al. (2006) J. Biol. Chem. 281:7220-7227
41. Madico et al. (2006) J Immunol 177:501-10.
42. WO2004/048404
43. Espevik and Niessen, 1986, J. Immunol. Methods 95: 99-105;
44. Ziegler-Heitbrock et al., 1988, Int. J. Cancer 41: 456-461

Example B

In a second strategy the fHbp and NHBA lipoproteins from *N. meningitidis* MC58 were cloned into the pETCOLA plasmid (which has 2 cloning sites for co-expression of genes of interest) under the control of an IPTG-inducible promoter either alone or concomitantly with NMB0313 and expressed in non-pathogenic *Escherichia coli* strain alone, or with co-expression of NMB0313.

Figure 7:
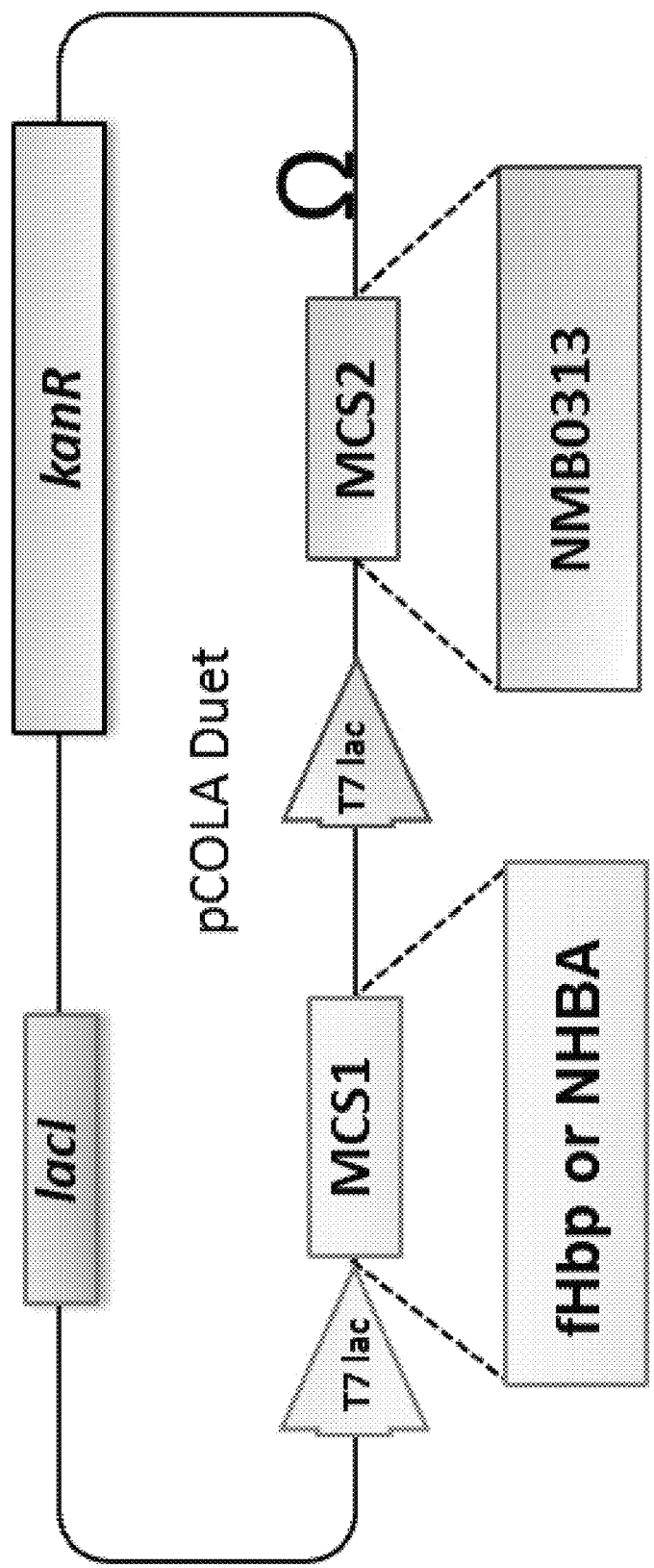
FIG. 7: Schematic representation of the pet Cola DUET plasmids with NMB0313, and fHBP or NHBA, cloned into one of the two multicloning sites.
Figure 8B:
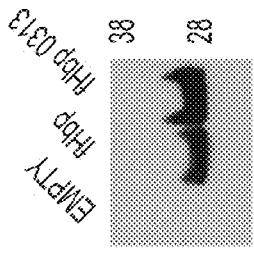
FIG. 8A-8D: Western blot analysis of *E. coli* lysates after culture in 0.1 mM IPTG stained with A) anti-fHbp and B) anti-NHBA polyclonal serum from cultures carrying pET-COLA alone (Empty) or pETCOLA expressing either lipoprotein alone (NHBA or fHbp, respectively) or co-expressing each lipoprotein with NMB0313 (NHBA 0313 or fHbp 0313, respectively). FACS analysis on respective cultures including *E. coli* expressing NMB0313 alone (0313) using (C)α-NHBA and (D)αfHbp antibody.
Figure 8D:
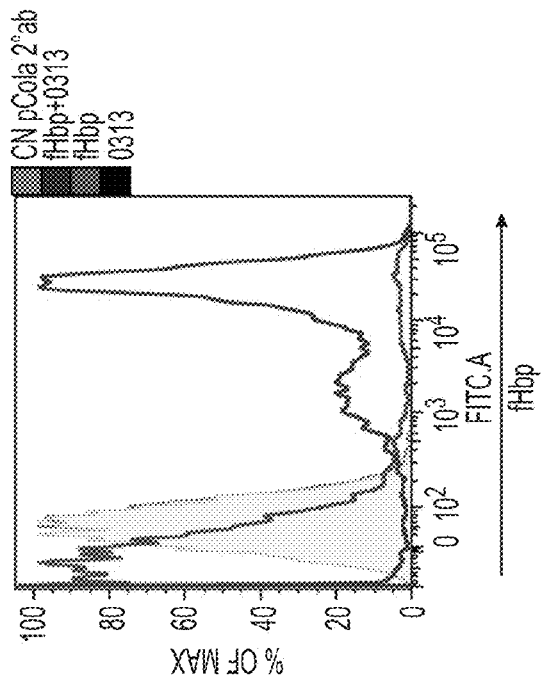
Figure 8A:
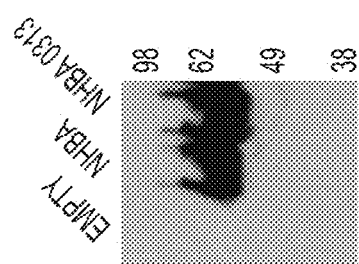
Figure 8C:
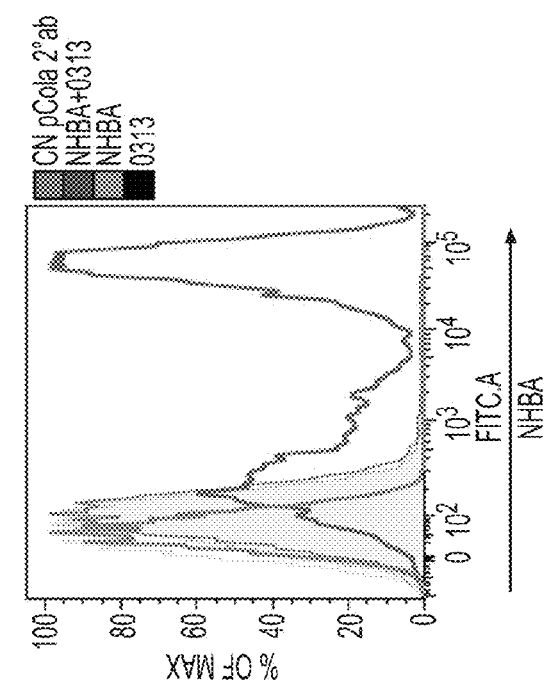

*E. coli* BL21 (DE3) strain was transformed with the empty petCOLA plasmid or petCOLA carrying fHbp, nhba or nmb0313 alone or pETCOLA carrying NHBA and nmb0313 or fHbp and nmb0313, respectively (FIG. 7).

Expression levels of all proteins responded to IPTG induction (data not shown) and the expression of both lipoproteins were confirmed by Western Blot analysis (FIG. 8A-8D). fHbp and NHBA expression in total lysates from *E. coli* coexpressing NMB0313 was higher than in the lysates of *E. coli* expressing the lipoproteins singly (FIG. 8A-8D). This confirms that the presence of NMB0313 has a positive effect on the expression of fHbp and NHBA in the *E. coli* heterologous system. FACS analysis revealed that NMB0313 is necessary for the surface exposure of both NHBA and fHbp (both *N. meningitidis* lipoproteins). While expression in the total lysates was clearly detectable by Western blot, no fHbp or NHBA were detectable on the surface when NMB0313 is not co-expressed.

We generated OMVs from the 6 different *E. coli* strains expressing different *N. meningitidis* lipoproteins, both with and without co-expression of NMB0313, which lead to their differential surface expression. After the purification of the OMVs from *E. coli*, SDS gel page was performed to characterize the preparation. *E. coli* OMVs were enriched with the *N. meningitidis* proteins (NMB0313, fHbp and NHBA) which are visible from the SDS gel page (FIG. 9). In particular, the differences in the amount of fHbp and NHBA in OMVs from cultures when expressed alone or co-expressed with NMB0313 was evident. Both lipoproteins are present in greater amounts in the OMVs from cultures with co-expression of NMB0313 (lanes 4 versus lane 3, and lane 6 versus lane 5).

After the purification of the OMVs from *E. coli*, the yield for all preparations were quantified. Yield evaluation of the preparation reveals an increase in the OMV amount purified from *E. coli* strains expressing *N. meningitidis* proteins, particularly for fHBP and NMB0313. As is show in the table below, OMVs from *E. coli* strain not expressing proteins (Empty) have the lowest OMV recovery. This suggests that overexpression of these outer membrane proteins results in hyperblebbing of the recombinant *E. coli* strains.

|  | Conc ug/uL | yield (mg/L) |
| --- | --- | --- |
| Empty | 0.344 | 1.769 |
| 0313 | 2.694 | 13.085 |
| fHbp | 0.982 | 10.381 |
| fHbp + 0313 | 1.851 | 19.566 |
| NHBA | 0.639 | 4.932 |
| NHBA + 0313 | 0.484 | 3.740 |

Figure 10:
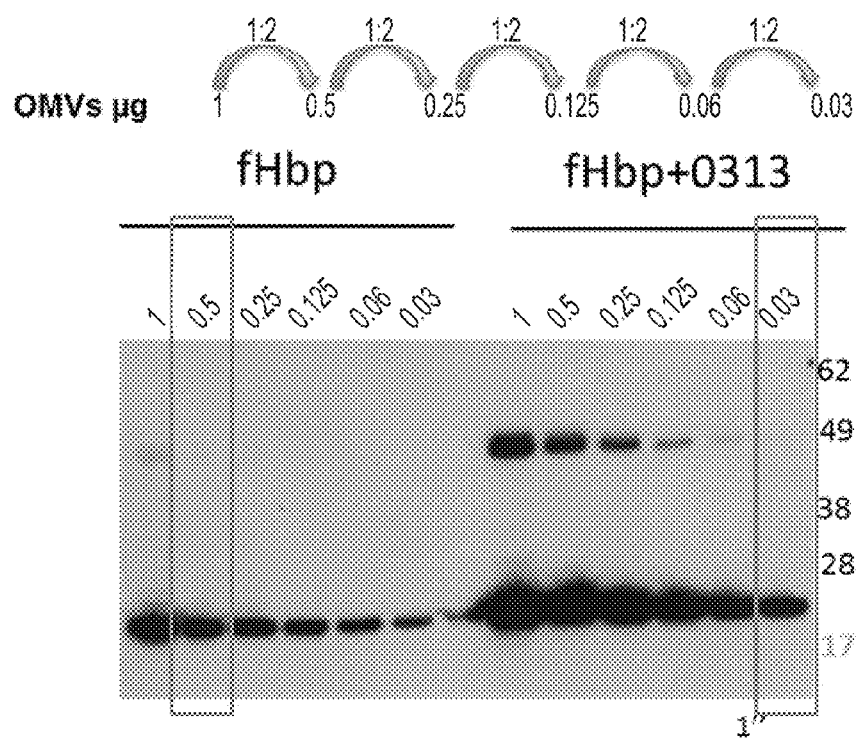
FIG. 10: Western blot using α-fHbp polyclonal antibody of serial dilution of *E. coli* OMVs starting at 1 ug quantities.

OMVs from *E. coli* co-expressing fHbp and NMB0313 contain high amounts of fHbp, where it appears as the most abundant protein in the OMV. In order to better quantify the difference in total amount of fHbp in OMVs prepared from cultures expressing fHbp alone or with NMB0313, WB analysis using a serial dilution of OMVs was performed (FIG. 10). Co-expression of fHbp and NMB0313 resulted in over 10 times more fHbp than fHbp expression alone.

These OMV preparations were included in an immunization scheme (FIG. 11). The study tested whether co-expression of NMB0313 with meningococcal lipoproteins in a heterologous *E. coli* background has an effect on the immunogenicity of the resulting OMVs. CD 1 mice were immunized intraperitoneally with the indicated doses of OMV (either 2 ug or 0.2 ug) two times on day 1 and day 21, and the final bleed was taken on day 35. Recombinant fHbp and NHBA (1 ug) were used as positive controls.

Figure 12A:
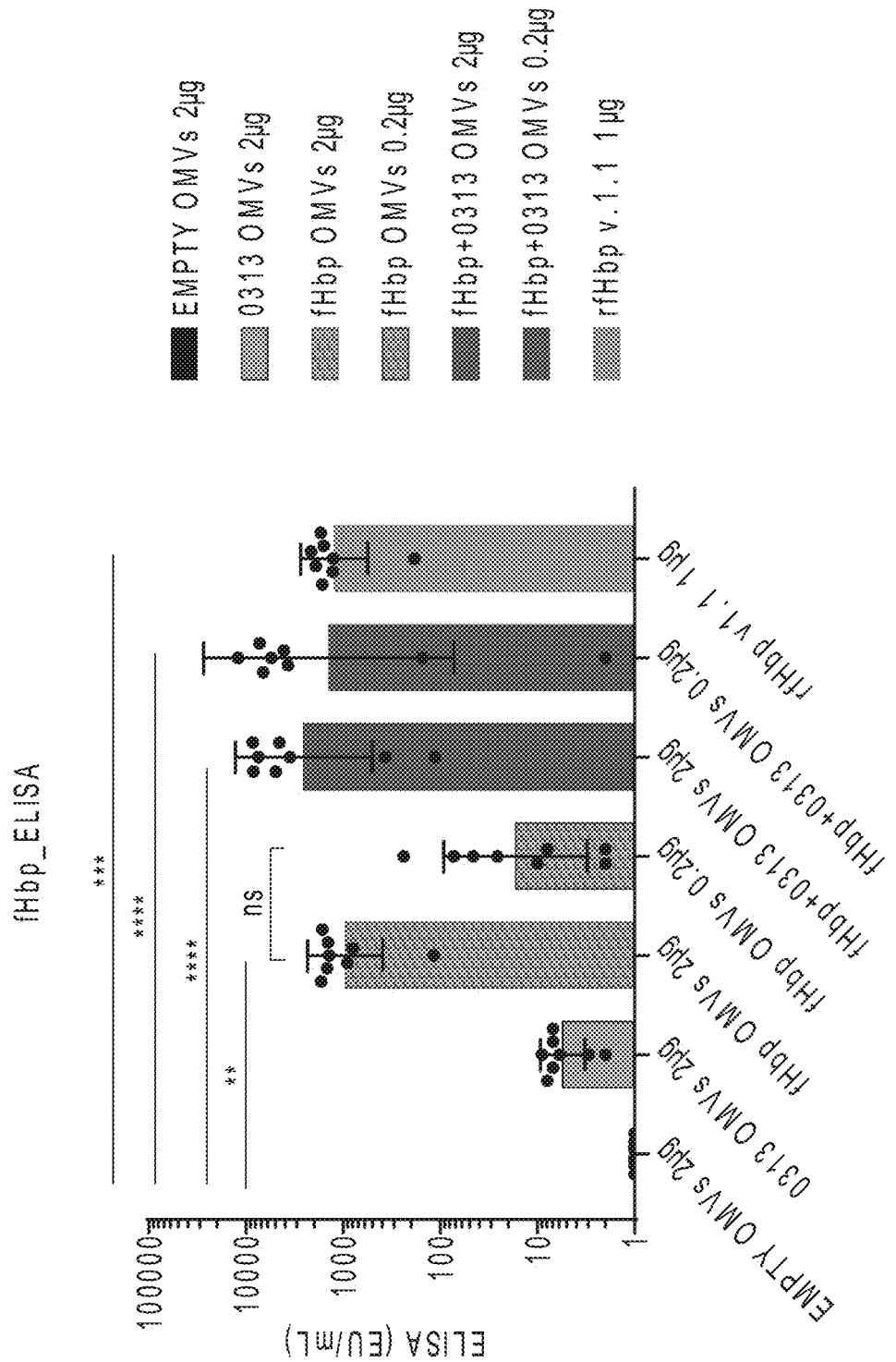

ELISA titers using recombinant fHbp as a coating antigen (FIG. 12A-12B) on the sera from groups 1-7 revealed that formulations of OMV carrying fHbp, with the exception of 0.2 ug of OMVs carrying fHbp alone, elicited antibody titers which were significantly higher than the negative controls (Empty-OMVs and 0313-OMVs). Immunizations with 1 μg of recombinant fHbp resulted in similar IgG titers to immunisations with 2 ug of fHbp OMVs and 0.2 ug of fHbp+0313 OMVs. There is a trend for dose-dependent anti-fHBP titres with the OMVs carrying fHbp alone (FHBP), but no apparent difference between the 2 doses of the OMV with both fHbp and NMB0313 (FHBP+0313).

Figure 13A:
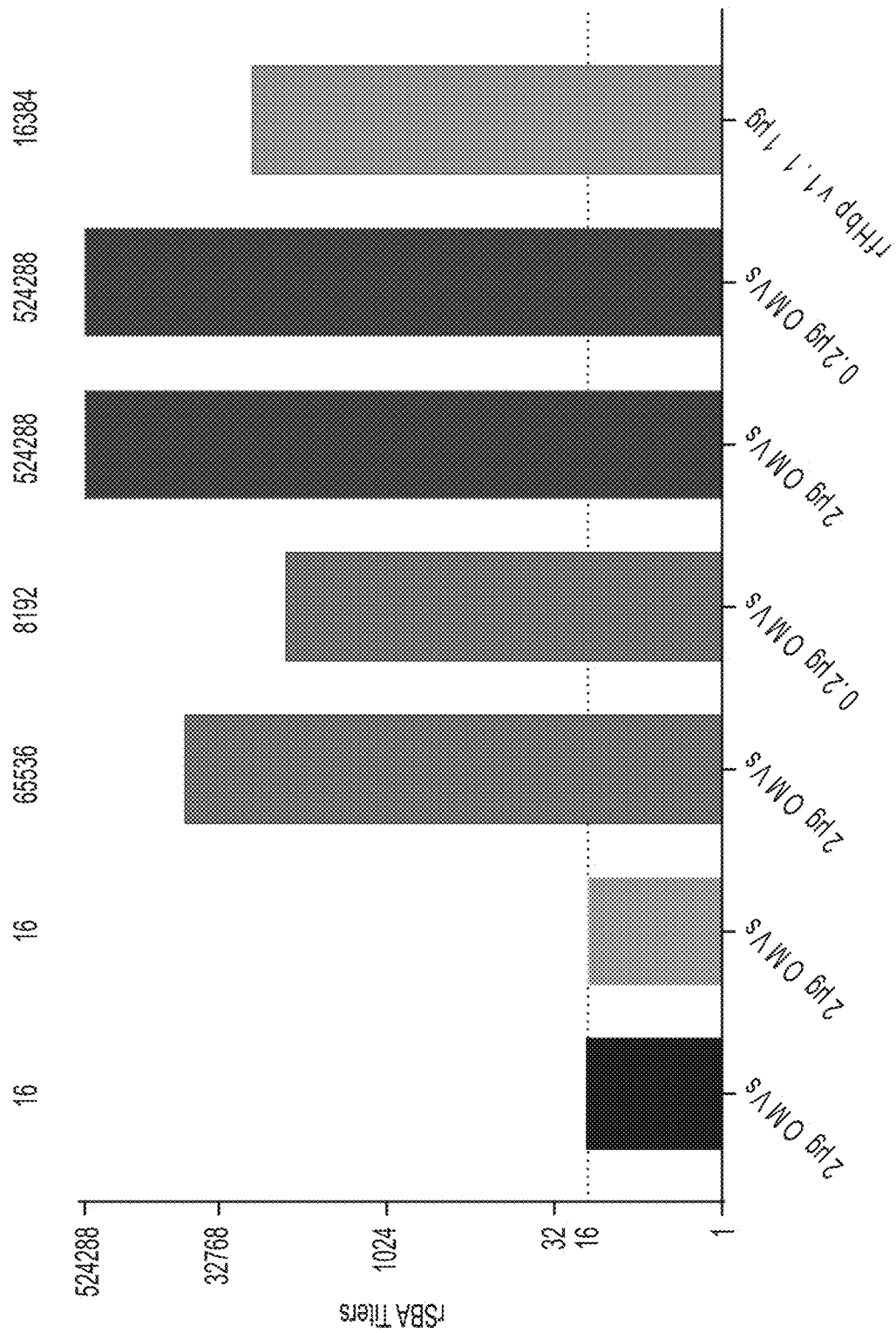

To measure the functional antibody responses we performed serum bactericidal assays with rabbit complement (rSBA) on the pooled sera from groups 1 to 7 on the H44/76 fHbp test strain (FIG. 13A-13B). No killing was achieved by the serum of the controls. Surprisingly, pooled sera derived from all the immunizations including 0.2 μg OMV carrying fHbp alone, show high bactericidal activity. Pooled sera from groups immunized with 2 ug of OMV carrying fHbp alone, and both doses of OMV carrying fHbp and NMB0313 gave higher titres compared to 1 μg rfHbp v1.1.

Figure 14A:
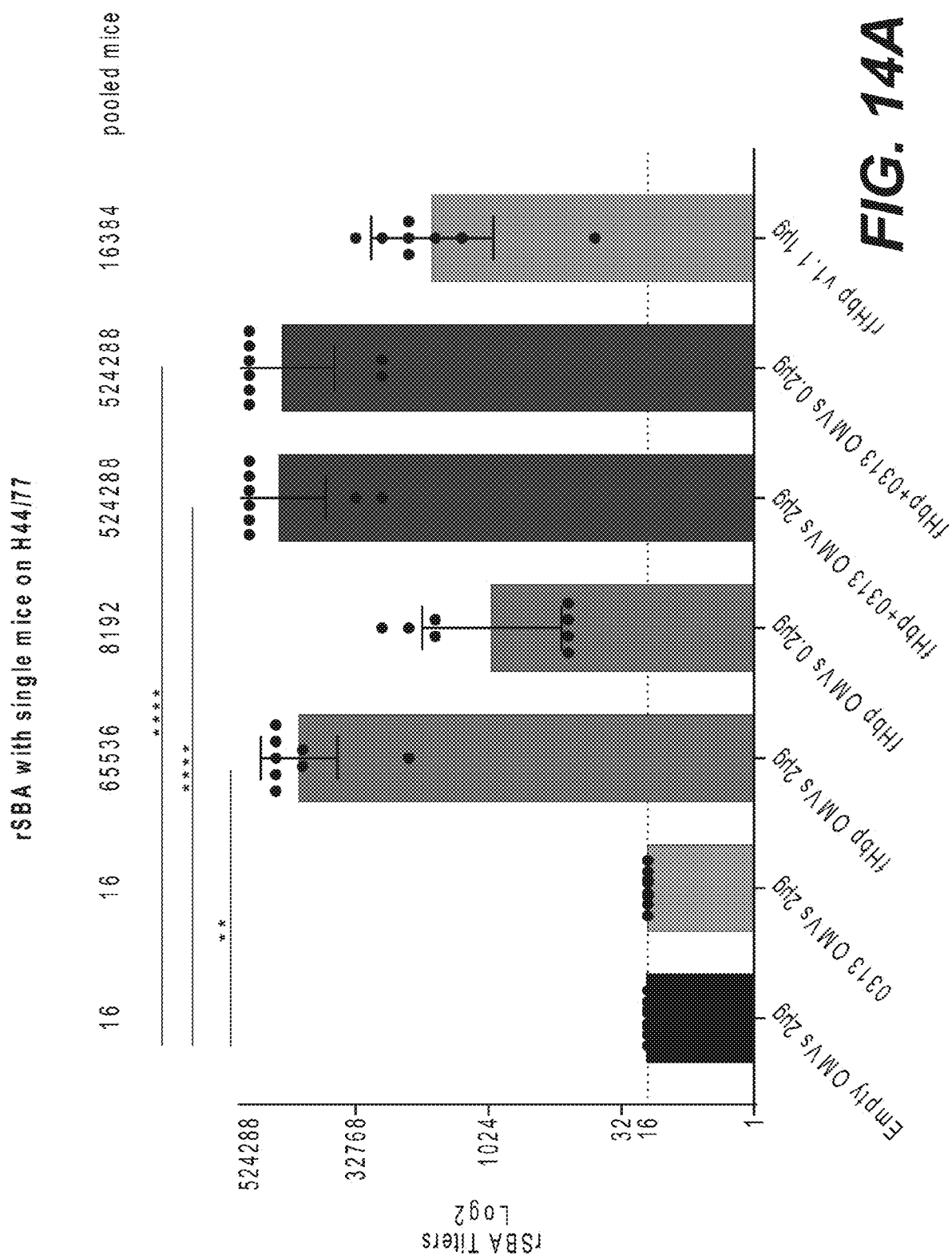

Performing rSBA using single mice (FIG. 14A-14B) sera confirmed the results obtained with pooled sera (FIG. 14A-14B). Interestingly the titres from 6 out of 8 mice from the immunizations (2 ug and 0.2 ug) of the OMVs with fHbp and NMB0313, were above the technical quantifiable limit in these experiments (titres>524288). In general the functional bactericidal responses elicited from the OMV formulations when fHbp is co-expressed with NMB0313 are higher than the responses with recombinant protein, and equivalent doses of OMVs with fHBP expressed alone. To conclude, all the preparations are able to generate antibodies against fHbp including 1 μg of recombinant fHbp. Nevertheless, fHbp expressed on the E. coli OMVs in a native conformation is able to elicitate higher bactericidal titers compared to 1 μg of recombinant fHbp. Those formulations of OMV resulting from the coexpression of NMB0313 with fHbp show the highest bactericidal responses with both high (2 ug) and low (0.2 ug) doses resulting in responses above the quantifiable range of the dilutions performed here. These data confirm that the co-expresssion of NMB0313 with model lipoproteins such as fHbp can significantly improve the immunogenicity of OMV preparations.

ELISA titers using recombinant NHBA as a coating antigen (FIG. 15A-15B 15) from sera from groups 1, 2, 8, 9 and 10 revealed that all preparations including NHBA elicited antibody titers which were significantly higher than the negative controls (Empty-OMVs and 0313-OMVs). Sera from mice immunized with NHBA+0313 OMVs show higher antibodies titers in comparison to sera of mice immunized with OMVs with only NHBA expression, and show a trend to be higher than mice immunized with 1 ug of NHBA.

Figure 16:
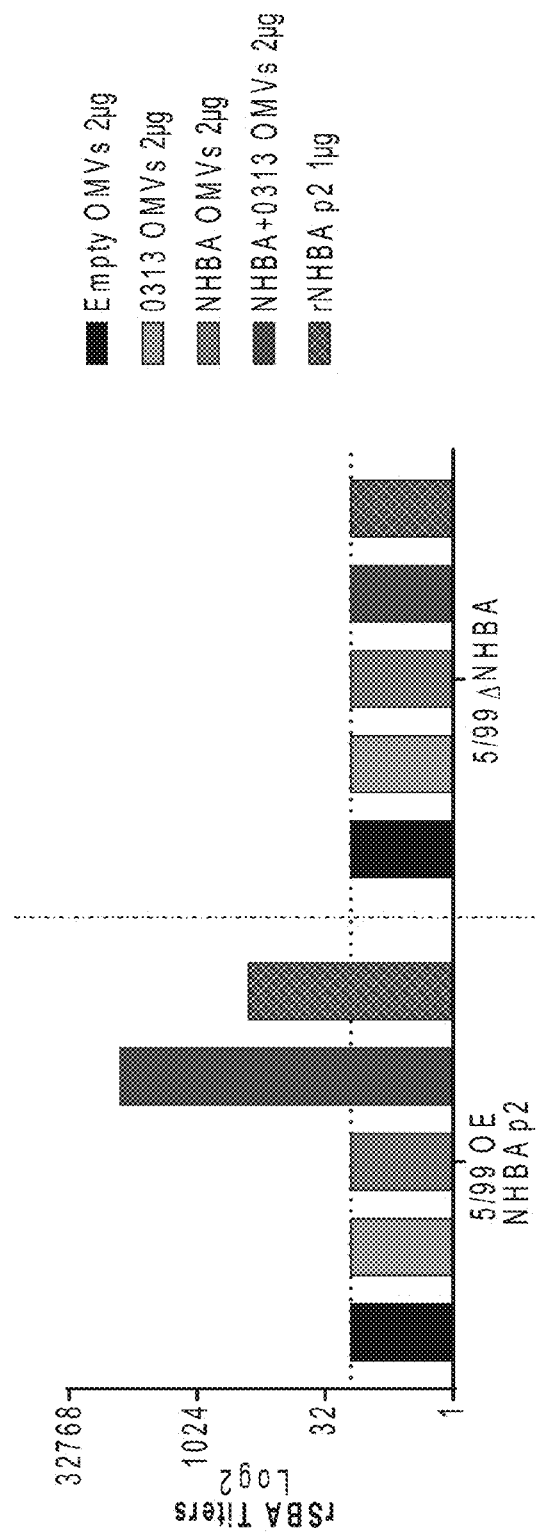
FIG. 16: rSBA titres of pooled sera from the indicated groups 1 (Empty Omvs 2 g), 2 (0313 OMVs 2 ug), 8 (NHBA OMVs 2 ug), 9 (NHBA+0313 OMVs 2 ug, and 10 (rNHBA 1 ug).

Functional responses were measured using rSBA of pooled sera against recombinant meningococcal test strains expressing NHBA (5/99 OE nHBAp2) or lacking the expression of NHBA (5/99ΔnhbA) (FIG. 16). Pooled sera from the group of mice immunized with OMVs from NHBA co-expressed with NM0313 gave high bactericidal titres which were higher than that of the group immunized with 1 ug of recombinant NHBA protein. These bactericidal titres were specific for NHBA as no bactericidal responses were measured against the test strain lacking NHBA expression. While positive IgG titres were measured by ELISA with the OMV expressing NHBA alone, these did not result in a functional response from the pooled sera from this group. Analysis of the bactericidal responses for pooled sera against a further 2 test strains M4407 and NGH38 showed that pooled sera from group 7 (OMV NHBA) failed to exhibit bactericidal titres whereas pooled sera from the OMV expressing Both NHBA and NMB0313 exhibited higher responses than the pooled sera from the group immunized with 1 ug of recombinant protein (FIG. 16).

Figure 17A:
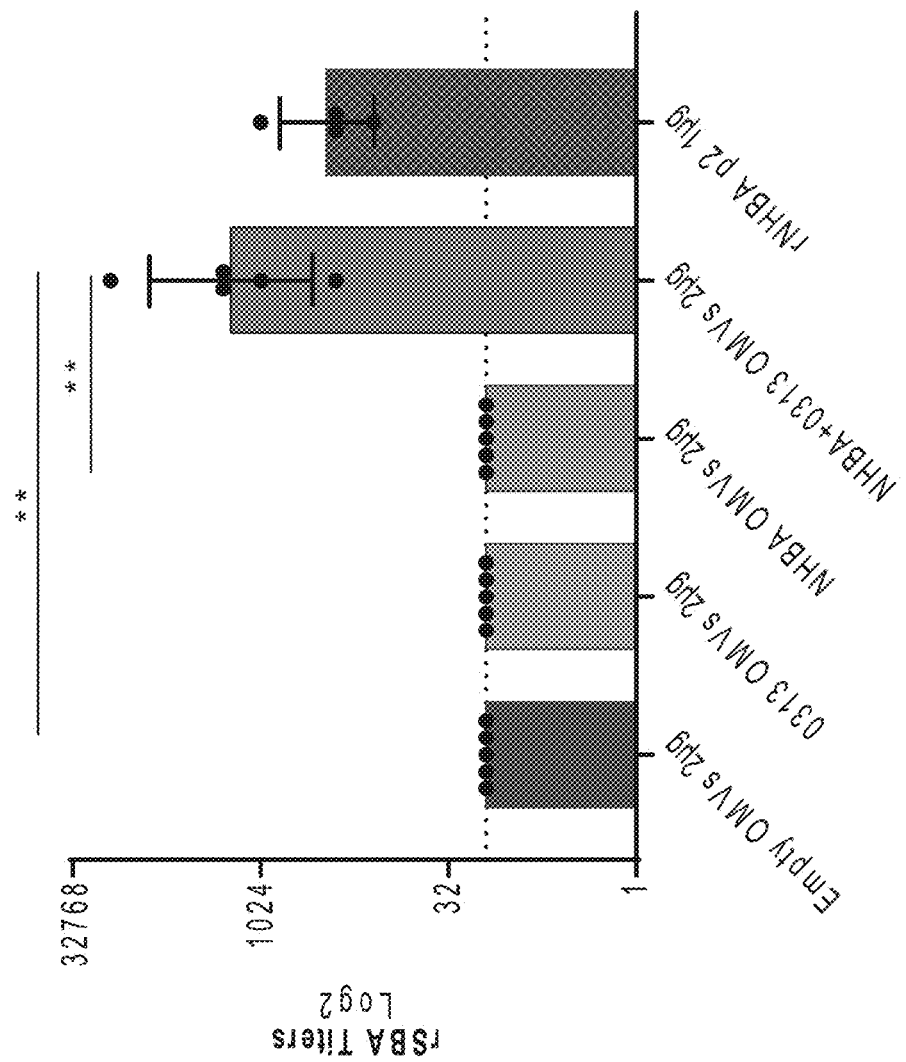
Figure 18B:
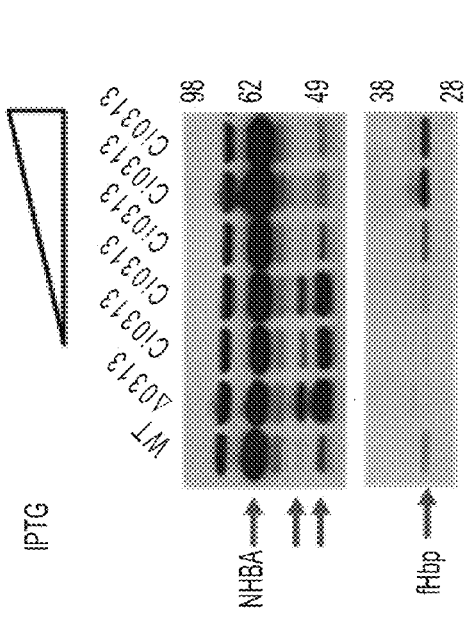
FIGS. 18A-18D: Western blot analysis of *N. meningitis* lysates stained with A) anti-NMB0313 and B) anti fHbp, anti-NHBA polyclonal serum from liquid coulter. NGH38 complemented strain (Ci0313) is growth with different IPTG concentration. C) FACS analysis of fHbp or (D) NHBA on respective cultures are report as a charts with the percentage of the mean fluorescence (MFI) extrapolate from FACS.
Figure 18A:
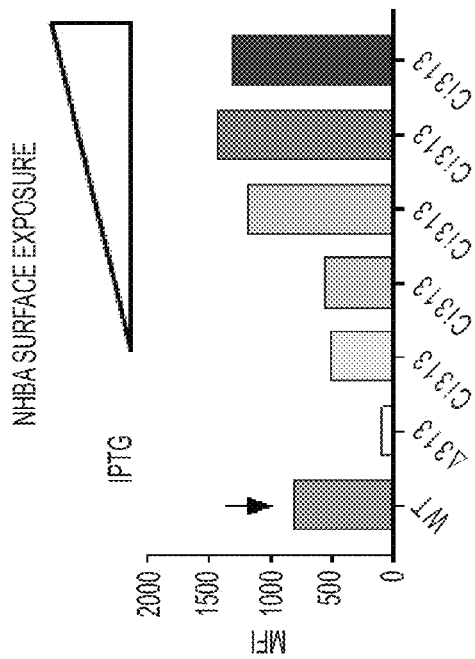
Figure 18D:
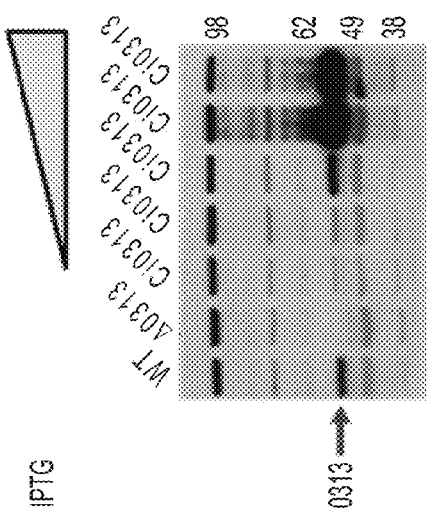
Figure 18C:
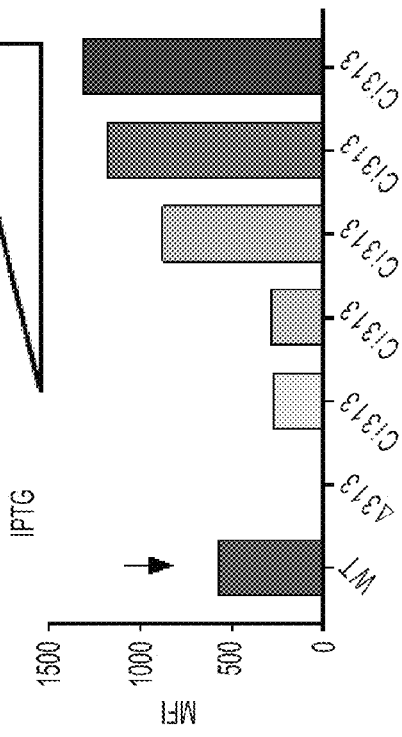

Performing rSBA using single mice sera (FIG. 17A-17B) confirms the results the results obtained with pooled sera. ELISA shows that E. coli OMVs carrying NHBA alone or with NMB0313 are able to generate antibodies against NHBA, while no functional responses are elicited by the OMV with NHBA alone. These data confirm that co-expression of NMB0313 with NHBA significantly increases the immunogenicity of the resultant OMVs when compared to those prepared from the strain expressing NHBA alone.

The deletion of nmb0313 affects the surface exposure of the analysed lipoproteins in NGH38 meningococcal strain. In particular, the absence of NMB0313 results in indetectable levels of NHBA on the surface and, as a consequence, its accumulation within the bacteria. On the other hand, decreased fHbp levels on the surface were detected and these low levels were a consequence of a general reduction of fHbp amount in the nmb0313 KO background as compared to the wild type. Therefore NMB0313 plays a critical role in translocation of NHBA to the surface of the bacterium but its deletion does not affect NHBA expression per se, however, NMB0313 contributes to the stable expression of fHbp and hence its surface expression. Subsequently, the phenotype was restored in NGH38 nmb0313 KO strain by genomic complementation of a functional copy of nmb0313 gene under the control of the IPTG inducible Tac promoter (FIG. 18A-18D). The complemented strain is able to express NMB0313 in an IPTG-dependent manner as demonstrated by western blot, and the highest concentrations of IPTG induce an overexpression of the NMB0313 protein.

To test how differential SLPs exposed on the OMVs delivery system due to the altered amount of NMB0313 is driving differential immune responses to those SLPs, OMVs from NGH38 strains were generated. OMVs from WT, Δ0313 and Ci0313 with 0.1 mM of IPTG were purified and analysed by WB and SDS gel page. The overexpression of NMB0313 is visible in the complemented strain, but there are no other significant differences in the protein SDS-Page profile (FIG. 19). These OMVs were used for mouse immunisation and rSBA analysis was performed on the pooled sera with 3 test strains. The rSBA shows a trend for reduced SBA titres from those meningococcus OMV prepared in the absence of constitutive expression (WT) and inducible expression (Ci0313) and, therefore, killing activity in those groups immunized. This confirms the role of NMB0313 in driving bactericidal activity also in a homolgous system.

Differences in bactericidal titers were decreased in the sera generated from the immunization with NGH38Δ0313 preparation, while the NGH38 Ci0313 titers show comparable bactericidal activity to the WT NGH38 strain (FIG. 20). rSBA using the reference strain 5/99 OE NHBAp2 and the corresponding ΔNHBA strain also show that this immunogenicity is not exclusively driven by NHBA. Probably, other lipoproteins are translocated on the surface in an NMB0313 dependent manner and these SLPs could affect the immunogenicity.

These data confirm a role for NMB0313 in the immunogenicity of meningococcal OMVs in that expression of NMB0313 in a meningococcal vaccine strain leads to OMV preparations with higher immunogenicity.

Materials & Methods

Bacterial Strains and Culture Conditions

Neisseria meningitidis (Nm) serogroup B strains (MC58, NHGH38, NZ 98/254 and its isogenic derivatives) and Escherichia coli (Ec) (DH5a and BL21-DE3) strains used in this study are listed.

N. meningitidis strains were grown on Gonococcal (GC) Medium Base (Difco) agar plates or in GC broth at 37° C. in 5% $CO_2$.

E. coli strains were cultured in LB agar or LB broth at 37° C.

Antibiotics were added when required. Kanamycin and chloramphenicol were added at final concentrations of 150

µg/mL and 5 µg/m for selection of *N. meningitidis* deletion mutants and complementing strains, respectively.

Ampicillin, kanamycin, or chloramphenicol was added at final concentrations of 100, 150 or 10 µg/mL for selection *E. coli*.

When required, isopropylβ-D-1-thiogalactopyranoside (IPTG) (1 mM) (Sigma) was added to culture media at the indicated final concentrations.

Construction of Mutant and Complementation Strains

DNA manipulations were carried out routinely as described for standard laboratory methods. [4]

To construct a NMB0313 deletion mutant, the nmb0313 gene was replaced with a kanamycin cassette by double crossing over. To do this, plasmid pGEMTUD313Kan was generated as follows.

Upstream and downstream flanking regions of nmb0313 were amplified from the MC58 chromosome with restriction enzyme sites and cloned into pGEMT plasmid. Kanamycin cassette was cloned as 1.4 kb XbaI fragment into the XbaI site between the two flanking regions. This plasmid was used to transform *N. meningitidis* strains.

Complementation of nmb0313 was achieved by insertion of a copy of the nmb0313 in the noncoding region between the converging ORF NMB 1428 and NMB 1429 of Δ0313 strains chromosome. To do this, plasmid pComPIn-dNMB0313 was generate by amplifying nmb0313 gene and cloned as AseI/NsiI fragment under the control of the inducible promoter Tac and the LacI repressor into pComPInd plasmid [5]

Primers and plasmids are listed in the attached tables.

The correct nucleotide sequence of each plasmid was confirmed by DNA sequencing.

Plasmids were linearized and used for the transformation of the *N. meningitidis* strains.

All transformants were verified both by PCR analysis and Western blot.

Western Blot Analysis

Grown overnight on agar plates were re-suspended in GC broth to an of 0.5 $OD_{600}$/mL. One milliliter of the resuspension was centrifuged for 5 min at 13000 rpm and the pellet was re-suspended in 100 µl of SDS loading buffer (50 mM Tris-HCl [pH 6.8], 2.5% SDS, 0.1% bromophenol blue, 10% glycerol, 5% f-mercaptoethanol, 50 mM DTT) [6].

In the case of liquid cultures, strains were grown till an of 0.5 $OD_{600}$/mL and one milliliter of the culture was pelleted and re-suspended in 100 µl of SDS loading buffer. Protein extracts were separated by SDS-PAGE on NuPAGE® Novex® 4-12% Bis-Tris Protein Gels in MES 1× (Life Technologies) and then transferred to nitrocellulose membranes. Membranes were blocked overnight at 4° C. with PBS+0.05% Tween 20 (Sigma) and 10% powdered milk (Sigma).

Primary antibody where diluted like reported in the table of antibody in PBS+0.05% Tween 20 and 3% powdered milk and incubated for 1 h with the membrane. A horseradish peroxidase(HRP)-conjugated anti-mouse IgG antibody and the Western Lightning ECL (Perkin Elmer) were used according to the manufacturer's instructions for the detection.

Fluorescence Activate Cell Sorting (FACS) Analysis of fHbp Expression

*N. meningitidis* strains and its isogenic derivatives, were collected after liquid cultures at $OD_{600}$ 0.5, when required IPTG was also added. Bacteria were inactivated by incubation with formaldehyde 0.5% for 1 hour at room temperature.

Labelling was performed with primary antibody diluted in PBS-0.5% BSA (Sigma) like reported in the table.

Primary antibody binding was detected using an anti-mouse (whole-molecule) FITC-conjugated antibody (Sigma) at the properly dilution.

Serum Bactericidal Activity Assay (SBA)

Day 1:

Streak a round chocolate agar plate with bacteria from the frozen stock and incubate 18 hours at 37° C. with 5% CO2

Day 2:

Inoculate 7 ml Mueller Hinton Broth (MHB) with glucose 0.25% (w/v), with bacteria until $OD_{600}$=0.05, blank=MHB Incubate the 7 ml bacteria in a shaker 150 rpm at 37° C. with 5% CO2.

Stop the incubation when $OD_{600}$=0.24-0.26 (about $2\text{-}4 \times 10^8$ CFU/ml), normally after 1.5-2 hours.

Make a working dilution of bacteria in assay buffer of $2\text{-}4 \times 10^4$ CFU/ml (1:10000) diluting the bacteria in two steps (i.e. 10 µL of bacterial culture in 1 mL of buffer, 100 µL of this suspension in 10 mL of buffer) to come to a final dilution of 1:10000.

Sera Dilution:

Fill the wells of the 96-wells sterile round bottom plate from column A to G with 25 ml buffer and the wells of column H with 20 ml.

Column A to F is for serum dilution: add to the first well of each raw 25 ml serum sample and make two fold serial dilution. The final volume in column A to G is now 25 ml/well.

Add 5 ml of sample and 12.5 ml/well of inactivated complement to column H.

Columns G and H represents the negative experimental controls: column G is the complement control, contents buffer, bacteria and active complement, column H is the serum control, contents buffer, bacteria, serum and inactivated complement.

Add 12.5 ml/well bacteria at the working dilution to all wells from column A to H.

Add 12.5 ml/well active complement to each well from column A to G.

Mix by shaking the microtiter plate.

Immediately after the addition of complement, take 10 ml of reaction from negative controls wells of columns G and H and streak on square Mueller-Hinton agar (MH agar) plates using tilt method, this moment represents the time zero (t=0). Incubate the 96-wells plate with the reaction at 37° C. with 5% $CO_2$.

After 60 minutes (t=60) take 10 ml of negative controls wells of columns G and H and streak on agar plates using tilt method. Spot 7 ml of each sample well in duplicate on square Petri dishes with MH agar by using a 12 channel multichannel (1-50 ml). Incubate O/N at 37° C. with 5% $CO^2$.

Day 3:

Count the amount of colonies in the controls at t=0 ant t=60.

Count the amount of colonies in the square plates with spots.

Calculate the number of colonies that represents the 50% of killing.

Bactericidal titer=the serum dilution that kill 50% of the added bacteria at time zero Sera Analysis—ELISA 100 µl antigen 0.01 µM were added to each well of a 96 well Nunc Maxsorp plate and incubated overnight at 4° C.

The wells were then washed three times with (PBT) washing buffer.

250 µl of (PVP) saturation buffer was added to each well and the plates incubated for 2 hours at 37° C.

Wells were washed three times with PBT.

100 µl of diluted sera were added to each well and the plates incubated for 2 hours at 37° C.

Wells were washed three times with PBT.

100 µl of Alkaline phosphatase-conjugated secondary antibodies serum diluted 1:2000 in dilution buffer were added to each well and the plates were incubated for 90 minutes at 37° C.

Wells were washed three times with PBT buffer.

100 µl of substrate p-nitrophenyl phosphate were added to each well and the plates were left at room temperature for 30 minutes.

100 µl 4N NaOH was added to each well and OD 405/620-630 nm was followed.

The antibody titers were quantified via interpolation against a reference standard curve.

Reagents:
1) Plate Nunc Maxisorp Cod. 442404
2) Saturation buffer (PVP) 2.7% polyvinylpyrrolidone 10 in water
3) Washing buffer (PBT) 0.05% Tween-20, in PBS 0.074M
4) Dilution buffer: 1% BSA, 0.05% Tween-20, in PBS 0.074M
5) Alkaline phosphatase-conjugated secondary antibodies Sigma Cod. A3562
6) Substrate p-nitrophenyl phosphate (pNPP) Sigma cod. P 7998
7) Tampone antigene (0.148M)

|        |              |
|--------|--------------|
| Na2HPO4 | 1.15 g      |
| Kcl    | 0.2 g        |
| KH2PO4 | 0.2 g        |
| Nacl   | 8.0 g        |
| pH     | 7.4 ± 0.1    |

Acqua distillata q.b. a 1 litro.

Isolation of Native *Neisseria meningitidis* Outer Membrane Vesicles (OMVs)

Growth of Strains

Inoculate the desired strain the day before the experiment onto a GC agar plate

Inoculate a 250 ml shaker flask containing 50 ml (MCDMI) with the starter culture to an $OD_{600}$ of 0.15 to 0.25

Incubate the flask at 37° C., 0% CO2 and 160 rpm well into stationary phase (approximately overnight)

Evaluate OD/ml (necessary for the yield) and collect samples for Wb and FACS (if is necessary)

Transfer the cultures into 50 ml Falcon tubes

Centrifuge the cultures at 3500 rpm for 30 min at 4° C.

Remove centrifuge buckets and transfer into biosafety cabinet

Transfer the supernatant into 125 ml Stericup filter bottles (0.22 m pore size) and filter it Remove 100 μl of the filtered supernatant and plate it on a GC agar plate as control for removal of *Neisseria*

Store the flask at 4° C. until inactivation/removal of bacteria in the filtered supernatant is confirmed after 24 to 48 h incubation of the control agar plates The filtered supernatants can be considered sterile if the plates plated with the filtered supernatant show no growth AND the plates with the cultures after incubation show growth Growth *E. coli* BL21

Inoculate the desired strain the day before the experiment onto a LB Kan plate

On the day of the experiment, stemperate few colonies on LB+Kan and growth Oday 180 rpm, 37° C.

Inoculate 1/100 in flask containing 50 ml (HTMC) with Kanamycin (50 μg/mL) and IPTG (0.1 mM)

Incubate the flask at 30° C. and 160 rpm well into stationary phase (approximately overnight)

Evaluate OD/ml (necessary for the yield) and collect samples for Wb and FACS (if is necessary)

Transfer the cultures into 50 ml Falcon tubes

Centrifuge the cultures at 3500 rpm for 30 min at 4° C.

Transfer the supernatant into 125 ml Stericup filter bottles (0.22 μm pore size) and filter it Store the flask at 4° C. until further steps Preparation of nOMVs From Filtered Supernatants Transfer the filtered supernatant into 70 ml ultracentrifuge tubes (suitable for rotor 45Ti) and fill up any empty tube space with PBS Centrifuge samples at 35'000 rpm (96'000×g, average) and 4° C. for 2 h PBS washing step Remove supernatant carefully Resuspend the pellet in 200 to 500 μl PBS (Protease inhibitors, can be added to the buffer at this stage)

Optionally, the pellet can be left to soak in the buffer overnight

Store pellets at −20° C. until further analysis

Analysis of nOMV Preparations

Determination of Protein Concentration

Determine the protein concentration using the BioRad DC kit

Use a protein standard curve from 2 to 0.06 mg/ml (three replicates)

Make appropriate dilutions of the OMV samples (up to 1:10, up to 1:100 for high yield isolation; pellet size!)

Measure the absorbance at 750 nm in a plate reader using endpoint measurement

Calculate the protein concentration using both linear, apply best fit

Determination of nOMV Composition

Resuspend specific amount of nOMVs with 2×SDS loading buffer (final volume 10-15 μl)

Run the protein sample on an SDS PAGE gel using MES buffer

Take 1 μg of total nOMV for WB analysis, blot the gel and develop using an specific antybodies Take 5-10 μg of nOMVs for SDS gel page the gel using either SimplyBlu safe stain or a silver protein stain Table of strains

| NAME | Description | Antibiotic resistance cassette | Reference |
|---|---|---|---|
| *N. meningitidis* strain | | | |
| NGH38 | *Neisseria meningitidis* wt strain | | |
| NGH38 Δ0313 | NGH38 derivative, kanamycin insertion in nmb0313 locus | Kanamycin | This study |

| Table of strains | | | |
|---|---|---|---|
| NAME | Description | Antibiotic resistance cassette | Reference |
| NGH38 Δ0313 ci0313 | NGH38 derivative, lacking nmb0313 gene with a copy of nmb0313 reintroduced out of locus under the control of an IPTG-inducible pTAC promoter | Chloramphenicol | This study |
| *E. coli* strains | | | |
| DH5a | fhuA2 lac(del)U169 phoA glnV44 Φ80' lacZ(del)M15 gyrA96 recA1 relA1 endA1 thi-1 hsdR17 | | |
| BL21 (DE3) | | | |

| Table of plasmid | | | |
|---|---|---|---|
| NAME | Description | Antibiotic resitance cassette | Reference |
| pCOLA DUET | The vector encodes two multiple cloning sites. with T7 promoter, COLA replicon from ColA, lacI repressor and KanR | Kanamycin | Novagen |
| pGEM-T | *E. coli* cloning vector, AmpR | Ampicillin | Promega |
| pComP$_{IND}$ CmR | Plasmid for allelic replacement at a chromosomal location between ORFs NMB1428 and NMB1429 and inducible expression under the control of the PTAC promoter and the lacI repressor. Upstream of the cloning site is a Cm resistance cassette | Ampicillin, Cloramphenicol | Ieva, R., et al. J Bacteriol, 2005. |
| pUD0313Kan | pGEM-T containing the flanking region of nmb0313 with Kan resistance cassette cloned as XmaI fragment between flanking regions | Ampicillin, Kanamycin | this study |
| pIND0313 | Plasmid for the complementation of nmb0313 in the Com region with an IPTG-inducible tac prmoter. Downstream of nmb0313 is cloned a Cm resistance cassette. | Ampicillin, Cloramphenicol | this study |
| pCOLA_0313 | Construct to express recombinant *N. meningitidis* NMB0313 protein in *E. coli* | Kanamycin | this study |
| pCOLA_NHBA | Construct to express recombinant *N. meningitidis* NMB2132 protein in *E. coli* | Kanamycin | this study |
| pCOLA_fHbp | Construct to express recombinant *N. meningitidis* NMB1870 protein in *E. coli* | Kanamycin | this study |
| pCOLA_NHBA_0313 | Construct to co-express recombinant *N. meningitidis* NMB0313 and NMB2132 proteins in *E. coli* | Kanamycin | this study |
| pCOLA_fHbp_0313 | Construct to co-express recombinant *N. meningitidis* NMB0313 and NMB1870 proteins in *E. coli* | Kanamycin | this study |

| Table of primer | | |
|---|---|---|
| Primer Name | Application | Sequence |
| 0313UP_F | fragment for 0313 KO generation in MenB with XbaI restriction site | GagatctagaGCCGGcattcgggcaaaaacc SEQ ID NO: 14 |
| 0313UP_R | fusion primer UP & DO flank of NMB0313 with XmaI restriction site | AACAGCAACCCGGGTATCAATCGGCG GAT SEQ ID NO: 15 |

-continued

Table of primer

| Primer Name | Application | Sequence |
|---|---|---|
| NMB0313_FW_DO | fusion primer UP & DO flank of NMB0313 with XmaI restriction site | CCGATTGATACCCGGGTTGCTGTTCC TTTTCG SEQ ID NO: 16 |
| NMB0313_RV_UP | fusion primer UP & DO flank of NMB0313 with XmaI restriction site | AACAGCAACCCGGGTATCAATCGGCG GAT SEQ ID NO: 17 |
| 0313pC_F | cloning NMB0313 gene in pCOM plasmid for complementarion in MENB NM0313KO | Gtgtattaatatggttattttttattttttgtg SEQ ID NO: 18 |
| 0313pC_R | cloning NMB0313 in pCOM plasmid for complementarion in MENB NM0313KO | Gtgtatgcattcagaacgttttattaaactc SEQ ID NO: 19 |
| i313F2 | cloning NMB0313 gene in MCS2 of pCOLA with MfeI restriction site | GCAGATCTCAATTGatggttattttttattttt gtg SEQ ID NO: 20 |
| i313R2 | cloning NMB0313 gene in MCS2 of pCOLA with XhoI restriction site | TTACCAGActcgagtcagaacgttttattaaac tc SEQ ID NO: 21 |
| iPCR_fhbp_MCS1_RV | cloning NMB1870 gene in MCS1 of pCOLA | AGCATTATgcggccgcTTATTGCTTGGC GGCAAG SEQ ID NO: 22 |
| iPCR_fHBP_MCS1_ (ifHbp1_2) | cloning NMB1870 gene in MCS1 of pCOLA | GGAGATATAccatggTGAATCGAACTG CCTTCTG SEQ ID NO: 23 |
| iPCR_NHBA_MCS1_cloning FW (iNHBA1_2) | cloning NMB2132 gene in MCS1 of pCOLA | GGAGATATAccatggTCTTTAAACGCA GCGTAATC SEQ ID NO: 24 |
| iPCR_NHBA_MCS1_cloning RV | cloning NMB2132 gene in MCS1 of pCOLA | AGCATTATgcggccgcTCAATCCTGCTC TTTTTTGC SEQ ID NO: 25 |

| Tables of antibodies | WB dilution | FACS dilution |
|---|---|---|
| α-fHbp polyclonal serum mouse | 1:5000 | 1:1000 |
| α-NHBA polyclonal mouse serum | 1:2000 | 1:800 |
| α-NHBA monoclonal mouse serum | 1:4000 | 1:1000 |
| α-mouse-FITC | | 1:1000 |
| α-mouse-HRP | 1:1000 | |

REFERENCES

1. Schwechheimer, C. and M. J. Kuehn, *Outer-membrane vesicles from Gram-negative bacteria: biogenesis and functions.* Nat Rev Microbiol, 2015. 13(10): p. 605-19.
2. Fantappie, L., et al., *Antibody-mediated immunity induced by engineered Escherichia coli OMVs carrying heterologous antigens in their lumen.* J Extracell Vesicles, 2014. 3.
3. Yogesh Hooda, C. C.-L. L., Andrew Judd, Carolyn M. Buckwalter, Hyejin Esther Shin, Scott D. Gray-Owen and Trevor F. Moraes, *Slam is an outer membrane protein that is required for the surface display of lipidated virulence factors in Neisseria.* Nature microbiology, 2016. 1.
4. Sambrook J, F. E., Maniatis T, *Molecular cloning: a laboratory manual.* Cold Spring Harbor Laboratory, 1989. 2nd ed.
5. Ieva, R., et al., *CrgA is an inducible LysR-type regulator of Neisseria meningitidis, acting both as a repressor and as an activator of gene transcription.* J Bacteriol, 2005. 187(10): p. 3421-30.
6. Oriente, F., V. Scarlato, and I. Delany, *Expression of factor H binding protein of meningococcus responds to oxygen limitation through a dedicated FNR-regulated promoter.* J Bacteriol, 2010. 192(3): p. 691-701.

The invention claimed is:

1. A hyper-blebbing Gram-negative bacterium which over-expresses a flippase wherein said flippase is (a) encoded by a sequence having 80% or greater sequence identity with SEQ ID NO: 1 or SEQ ID NO:3 and/or (b) comprises a sequence having 80% or greater sequence identity with SEQ ID NO: 2 or SEQ ID NO:4; and
   wherein said bacterium is genetically modified to produce a lipopolysaccharide (LPS) that has less toxicity than the toxicity of a corresponding wild-type LPS; and
   said over-expression results in the outer membrane vesicles (OMVs) or Generalised Modules for Membrane Antigens (GMMAs) spontaneously produced by said bacterium to be enriched for one or more lipoproteins when compared to OMVs or GMMAs produced by bacterium not over-expressing said flippase; and
   wherein the one or more enriched lipoprotein comprises lipoprotein selected from the group consisting of fHbp, NHBA, and NadA and variants thereof, and combinations thereof.

2. The hyper-blebbing Gram-negative bacterium of claim 1 which is selected from the group consisting of *Neisseria, Salmonella, Shigella, Haemophilus, Bordetella, Moraxella* and *Escherichia*.

3. The hyper-blebbing Gram-negative bacterium of claim 2 which is selected from the group consisting of *Neisseria meningitidis, Neisseria gonorrhoeae, Salmonella typhi, Salmonella typhimurium, Shigella flexneri, Shigella dysenteriae, Shigella boydii, Shigella sonnei, Haemophilus influenzae, Bordetella pertussis* and *Escherichia coli*.

4. The hyper-blebbing Gram-negative bacterium of claim 3 which is a *Neisseria meningitidis* or *Neisseria gonorrhoeae* strain which has been genetically modified by down-regulating expression of GNA33.

5. The hyper-blebbing Gram-negative bacterium of claim 4 which has been genetically modified by mutation of at least one gene selected from the group consisting of lpxL1, synX and lgtA.

6. The hyper-blebbing Gram-negative bacterium of claim 3 which is a *Haemophilus influenza, Moraxella catarrhalis* or *Escherichia coli* strain which has been genetically modified by down-regulating expression of one or more genes selected from the group consisting of tolQ, tolR, tolX, tolA and tolB.

7. The hyper-blebbing Gram-negative bacterium of claim 3 which is a *Shigella flexneri, Shigella dysenteriae, Shigella boydii* or *Shigella sonnei* strain which has been genetically modified by down-regulating expression of tolR or OmpA.

8. The hyper-blebbing Gram-negative bacterium of claim 7 which has been genetically modified by mutation of at least one gene selected from the group consisting of htrA, msbB1, msbB2 and virG.

9. The hyper-blebbing Gram-negative bacterium of claim 1 which has been genetically engineered by one or more processes selected from the following group: (a) a process of down-regulating expression of immunodominant variable or non-protective antigens, (b) a process of up-regulating expression of protective outer membrane protein (OMP) antigens, (c) a process of down-regulating a gene involved in rendering the lipid A portion of LPS toxic, (d) a process of up-regulating a gene involved in rendering the lipid A portion of LPS less toxic, and (e) a process of genetically modifying the bacterium to express a heterologous antigen.

10. A preparation of outer membrane vesicles obtained from the bacterium as defined in claim 1.

11. The preparation of membrane vesicles of claim 10 which is capable of being filtered through a 0.22 μm membrane.

12. A pharmaceutical composition comprising the preparation of outer membrane vesicles of claim 11 together with a pharmaceutically acceptable diluent or carrier.

13. A method of protecting, preventing, or treating a human or animal body comprising administering to the human or animal body an effective amount of the pharmaceutical composition according to claim 12.

14. A method of protecting an individual against a bacterial infection which comprises administering to the individual an effective amount of the preparation as defined in claim 10.

15. A process for preparing a pharmaceutical composition comprising a preparation of outer membrane vesicles, the process comprising: (a) inoculating a culture vessel containing a nutrient medium suitable for growth of the bacterium of claim 1; (b) culturing said bacterium; (c) recovering outer membrane vesicles from the medium; and (d) mixing the outer membrane vesicles with a pharmaceutically acceptable diluent or carrier.

16. The process of claim 15 which further comprises a step after either step (c) or step (d), comprising sterile-filtering the preparation of outer membrane vesicles.

17. A method for producing a hyper-blebbing bacterium according to claim 1 which method comprises genetically modifying
   a hyper-blebbing Gram-negative bacterium to over-express a flippase wherein said flippase is (a) encoded by a sequence having 80% or greater sequence identity with SEQ ID NO: 1 or SEQ ID NO:3 and/or (b) comprises a sequence having 80% or greater sequence identity with SEQ ID NO: 2 or SEQ ID NO:4; and
   further genetically modifying said bacterium to produce a lipopolysaccharide (LPS) that has less toxicity than the toxicity of a corresponding wild-type LPS; wherein
   said over-expression results in the outer membrane vesicles (OMVs) or Generalised Modules for Membrane Antigens (GMMAs) spontaneously produced by said bacterium to be enriched for one or more lipoproteins when compared to OMVs or GMMAs produced by bacterium not over-expressing said flippase; and
   wherein the one or more enriched lipoprotein comprises lipoprotein selected from the group consisting of fHbp, NHBA, and NadA and variants thereof, and combinations thereof.

* * * * *